US005807893A

United States Patent [19]
Voelker et al.

[11] Patent Number: 5,807,893
[45] Date of Patent: *Sep. 15, 1998

[54] PLANT THIOESTERASES AND USE FOR MODIFICATION OF FATTY ACID COMPOSITION IN PLANT SEED OILS

[76] Inventors: Toni Alois Voelker, 1206 Covell Pl.; Huw Maelor Davies, 307 Grande Ave., both of Davis, Calif. 95616

[*] Notice: The term of this patent shall not extend beyond the expiration date of Pat. No. 5,639,790.

[21] Appl. No.: 469,203

[22] Filed: Jun. 6, 1995

Related U.S. Application Data

[63] Continuation of Ser. No. 142,473, Nov. 18, 1993, Pat. No. 5,639,790.
[51] Int. Cl.$^6$ .......................... A61K 31/23; A61K 31/20; A61K 35/78
[52] U.S. Cl. ........................ 514/552; 514/558; 424/195.1
[58] Field of Search .................................. 514/552, 558; 424/195.1

[56] References Cited

U.S. PATENT DOCUMENTS

| | | | |
|---|---|---|---|
| 4,386,111 | 5/1983 | Heteren et al. | 426/603 |
| 4,410,557 | 10/1983 | Miller | 426/607 |
| 4,614,663 | 9/1986 | Rule | 426/601 |
| 4,721,626 | 1/1988 | Rule | 426/601 |

FOREIGN PATENT DOCUMENTS

| | | |
|---|---|---|
| 0 255 378 | 2/1988 | European Pat. Off. . |
| 0 323 753 | 7/1989 | European Pat. Off. . |
| 91911522 | 5/1992 | European Pat. Off. . |
| 92913220 | 7/1993 | European Pat. Off. . |
| WO 91/16421 | 10/1991 | WIPO . |
| PCT/US92/ 04332 | 8/1992 | WIPO . |
| WO 95/06740 | 3/1995 | WIPO . |

OTHER PUBLICATIONS

Daulatabad, C., et al., "Studies on Verbenaceae Seed Oils," *Chem Abstracts* (1990) 112:345 No. 232551q.

Poulose, et al., "Cloning and Sequencing of the cDNA for S–Acyl Fatty Acid Synthase Thioesterase from the Uropygial Gland of Mallard Duck," *J. of Bio. Chem.* (1985) 260(29):15953–15958 Davies, et al., Developmental Induction, Purification, and Further Characterization of 12:0–ACP Thioesterase from Immature Cotyledons of *Umbellularia californica, Archives of Biochem. and Biophy.* (1991) 290(1) : 37–45.

Naggert, et al., "Cloning and Sequencing of the Medium–Chain S–acyl Fatty Acid Synthetase Thioester Hydrolase cDNA From Rat Mammary Gland," *Biochem. J.* 243:597–601.

Pollard, et al., "Fatty Acid Synthesis in Developing Oilseeds," *Plant Lipids* (1987) 455–463.

Cao, et al., "Acyl Coenzyme A Preference of Diacylglycerol Acyltransferase from the Maturing Seeds of Cuphea, Maize, Rapeseed and Canola," *Plant Physiol.* (1987)84:762–765.

Knauf, Vic C., "Genetic Engineering of Oil Composition in Rapeseed," *Cell Biochem. Suppl 16F.* (1992) p. 201 Abstract Y012.

Voelker, et al., "Production of Medium–Chain Fatty Acids in Transgenic Oilseeds," *Plant Physiology, Supp.* (1992) vol. 99, No. 1, p. 76, Abstract 455.

Voelker, et al., "Engineering Laurate Production in Oilseeds," Advances in Gene Technology: Feeding the World in the 21st Century, Biotechnology, vol. 10, No. 1 (1992), p. 59 and Miami Short Reports (1992) Miami Winter Symp. Jan. 19–24, vol. 2, p. 102.

Bayley, et al., "Metabolic Consequences of Expression of the Medium Chain Hydrolase Gene of The Rat In Mouse NIH 3T3 Cells," *Bio/Tech* (1988) 6:1219–1221.

Downey, et al., "Genetic Control of Fatty Acid Composition In Oilseed Crops," *Proceedings of the Flax Institure USA* (1971) 41(3):1–3.

Knauf, et al., "Reprogramming Levels of Fatty Acid Synthesis Enzymes In Developing Embryos of Rapeseed, " *J. Cell Biochem. Suppl.* (1990) 14E:266.

Bafor, et al., "Properties of the Glycerol Acylating Enzymes in Microsomal Preparations from the Developing Seeds of Safflower *(Carthamus tinctorius)* and Turnip Rape *(Brassica campestris)* and their Ability to Assemble Cocoa–Butter Type Fats," JAOCS (1990) 67(4) :217–225.

Battey, et al., "Genetic engineering for plant oils: potential and limitation," TIBTECH (1989) 7:122–126.

Knauf, V., "The application of genetic engineering to oilseed crops," TIBTECH (1987) 5:40–47.

McKeon, et al., "Purification and Characterization of the Stearoyl–acyl Carrier Protein Desaturase and the Acyl–acyl Carrier Protein Thioesterase from Maturing Seeds of Safflower," *J. of Biol. Chem.* (1982) 257(20) :12141–12147.

Pollard, et al., "A Specific Acyl–ACP Thioesterase Implicated in Medium–Chain Fatty Acid Production In Immature Cotyledons of *Umbellularia californica, "Arch. of Biochem. and Biophys.* (1991) 284(2):306–312.

Pollard, Figures 1 through 5 representing information presented as slides at the Seventh International symposium on Plant Lipids, held Jul. 27 –Aug 1, 1986 at the University of California, Davis, California.

Davies, et al., "Developmental Induction, Purification and Further Characterization of 12:0–ACP Thioesterase from Immature Cotyledons of *Umbellularia californica, "Arch. of Biochem. and Biophys.* (1991) 290(1) : 37–45.

*Primary Examiner*—John W. Rollins
*Attorney, Agent, or Firm*—Donna E. Scherer; Carl J. Schwedler

[57] ABSTRACT

By this invention, further properties and uses of plant medium chain thioesterases are provided. In particular, it is now seen that plant seed which would not normally contain medium-chain fatty acid, either as free fatty acids or incorporated into triglyceride molecules, can be found to contain such medium-chain fatty acids. By seed which would not normally contain medium-chain fatty acid is meant seed which contains less than 0.1 mole percent of a given medium-chain fatty acid in total fatty acids. Thus, any plant seed containing a minimum of 1.0 mole percent of a given medium-chain fatty acid in total fatty acids is significantly modified. In one embodiment, this invention relates to plant seed and oil derived from that seed, which normally do not contain laurate, but now are found to contain laurate.

15 Claims, 42 Drawing Sheets

```
AGAGAGAGAG AGAGAGAGAG AGCTAAATTA AAAAAAAAAC CCAGAAGTGG GAAATCTTCC    60
CCATGAAATA ACGGATCCTC TTGCTACTGC TACTACTACT ACTACAAACT GTAGCCATTT   120
ATATAATTCT ATATAATTTT CAACATGGCC ACCACCTCTT TAGCTTCCGC TTTCTGCTCG   180
ATGAAAGCTG TAATGTTGGC TCGTGATGGC CGGGGCATGA AACCCAGGAG CAGTGATTTG   240
CAGCTGAGGG CGGGAAATGC GCCAACCTCT TTGAAGATGA TCAATGGGAC CAAGTTCAGT   300
TACACGGAGA GCTTGAAAAG GTTGCCTGAC TGGAGCATGC TCTTTGCAGT GATCACAACC   360
ATCTTTTCGG CTGCTGAGAA GCAGTGGACC AATCTAGAGT GGAAGCCGAA GCCGAAGCTA   420
CCCCAGTTGC TTGATGACCA TTTTGGACTG CATGGGTTAG TTTTCAGGCG CACCTTTGCC   480
ATCAGATCTT ATGAGGTGGG ACCTGACCGC TCCACATCTA TACTGGCTGT TATGAATCAC   540
ATGCAGGAGG CTACACTTAA TCATGCGAAG AGTGTGGGAA TTCTAGGAGA TGGATTCGGG   600
ACGACGCTAG AGATGAGTAA GAGAGATCTG ATGTGGGTTG TGAGACGCAC GCATGTTGCT   660
GTGGAACGGT ACCCTACTTG GGGTGATACT GTAGAAGTAG AGTGCTGGAT TGGTGCATCT   720
GGAAATAATG GCATGCGACG TGATTTCCTT GTCCGGGACT GCAAAACAGG CGAAATTCTT   780
```

FIGURE 1A -1

```
ACAAGATGTA  CCAGCCTTTC  GGTGCTGATG  AATACAAGGA  CAAGGAGGTT  GTCCACAATC   840
CCTGACGAAG  TTAGAGGGGA  GATAGGGCCT  GCATTCATTG  ATAATGTGGC  TGTCAAGGAC   900
GATGAAATTA  AGAAACTACA  GAAGCTCAAT  GACAGCACTG  CAGATTACAT  CCAAGGAGGT   960
TTGACTCCTC  GATGGAATGA  TTTGGATGTC  AATCAGCATG  TGAACAACCT  CAAATACGTT  1020
GCCTGGGTTT  TTGAGACCGT  CCCAGACTCC  ATCTTTGAGA  GTCATCATAT  TTCCAGCTTC  1080
ACTCTTGAAT  ACAGGAGAGA  GTGCACGAGG  GATAGCGTGC  TGCGGTCCCT  GACCACTGTC  1140
TCTGGTGGCT  CGTCGGAGGC  TGGGTTAGTG  TGCGATCACT  TGCTCCAGCT  TGAAGGTGGG  1200
TCTGAGGTAT  TGAGGGCAAG  AACAGAGTGG  AGGCCTAAGC  TTACCGATAG  TTTCAGAGGG  1260
ATTAGTGTGA  TACCCGCAGA  ACCGAGGGTG  TAACTAATGA  AAGAAGCATC  TGTTGAAGTT  1320
TCTCCCATGC  TGTTCGTGAG  GATACTTTTT  AGAAGCTGCA  GTTTGCATTG  CTTGTGCAGA  1380
ATCATGGTCT  GTGGTTTTAG  ATGTATATAA  AAAATAGTCC  TGTAGTCATG  AAACTTAATA  1440
TCAGAAAAAT  AACTCAATGG  GTCAAGGTTA  TCGAAGTAGT  CATTTAAGCT  TTGAAATATG  1500
TTTTGTATTC  CTCGGCTTAA  TCTGTAAGCT  CTTTCTCTTG  CAATAAAGTT  CGCCTTTCAA  1560
T                                                                      1561
```

FIGURE 1A-2

```
Met Ala Thr Thr Ser Leu Ala Ser Ala Phe Cys Ser Met Lys Ala Val
  1               5                  10                 15

Met Leu Ala Arg Asp Gly Arg Gly Met Lys Pro Arg Ser Ser Asp Leu
                 20                 25                 30

Gln Leu Arg Ala Gly Asn Ala Pro Thr Ser Leu Lys Met Ile Asn Gly
                 35                 40                 45

Thr Lys Phe Ser Tyr Thr Glu Ser Leu Lys Arg Leu Pro Asp Trp Ser
 50                 55                 60

Met Leu Phe Ala Val Ile Thr Thr Ile Phe Ser Ala Ala Glu Lys Gln
 65                 70                 75                 80

Trp Thr Asn Leu Glu Trp Lys Pro Lys Pro Lys Leu Pro Gln Leu Leu
                 85                 90                 95

Asp Asp His Phe Gly Leu His Gly Leu Val Phe Arg Arg Thr Phe Ala
                100                105                110
```

FIGURE 1B-1

Ile Arg Ser Tyr Glu Val Gly Pro Asp Arg Ser Thr Ser Ile Leu Ala
115                 120                 125

Val Met Asn His Met Gln Glu Ala Thr Leu Asn His Ala Lys Ser Val
130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
165                 170                 175

Pro Thr Trp Gly Asp Thr Val Glu Val Cys Trp Ile Gly Ala Ser
180                 185                 190

Gly Asn Asn Gly Met Arg Arg Asp Phe Leu Val Arg Asp Cys Lys Thr
195                 200                 205

Gly Glu Ile Leu Thr Arg Cys Thr Ser Leu Ser Val Leu Met Asn Thr
210                 215                 220

FIGURE 1B-2

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

FIGURE 1B-3

Ser Glu Ala Gly Leu Val Cys Asp His Leu Leu Gln Leu Glu Gly Gly
                340                 345                 350

Ser Glu Val Leu Arg Ala Arg Thr Glu Trp Arg Pro Lys Leu Thr Asp
                355                 360                 365

Ser Phe Arg Gly Ile Ser Val Ile Pro Ala Glu Pro Arg Val
                370                 375                 380

FIGURE 1B-4

```
AAAAAAGTAC AAACTGTATG GTAGCCATTT ACATATAACT ACTCTATAAT TTTCAAC ATG    60
                                                              Met
                                                                1

GTC ACC ACC TCT TTA GCT TCC GCT TTC TTC TCG ATG AAA GCT GTA ATG   108
Val Thr Thr Ser Leu Ala Ser Ala Phe Phe Ser Met Lys Ala Val Met
          5              10              15

TTG GCT CCT GAT GGC AGT GGC ATA AAA CCC AGG AGC AGT GGT TTG CAG   156
Leu Ala Pro Asp Gly Ser Gly Ile Lys Pro Arg Ser Ser Gly Leu Gln
         20              25              30

GTG AGG GCG GGA AAG GAA CAA AAC TCT TGC AAG ATG ATC AAT GGG ACC   204
Val Arg Ala Gly Lys Glu Gln Asn Ser Cys Lys Met Ile Asn Gly Thr
     35              40              45

AAG GTC AAA GAC ACG GAG GGC TTG AAA GGG CGC AGC ACA TTG CAT GGC   252
Lys Val Lys Asp Thr Glu Gly Leu Lys Gly Arg Ser Thr Leu His Gly
 50              55              60              65
```

```
TGG AGC ATG CCC CTT GAA TTG ATC ACA ACC ATC TTT TCG GCT GCT GAG    300
Trp Ser Met Pro Leu Glu Leu Ile Thr Thr Ile Phe Ser Ala Ala Glu
                70                  75                  80

AAG CAG TGG ACC AAT CTA GTT AGT AAG CCA CCG CAG TTG CTT GAT GAC    348
Lys Gln Trp Thr Asn Leu Val Ser Lys Pro Pro Gln Leu Leu Asp Asp
            85                  90                  95

CAT TTA GGT CTG CAT GGG CTA GTT TTC AGG CGC ACC TTT GCA ATC AGA    396
His Leu Gly Leu His Gly Leu Val Phe Arg Arg Thr Phe Ala Ile Arg
        100                 105                 110

TGC AGT GAG GTT GGA CCT GAC CGC TCC ACA TCC ATA GTG GCT GTT ATG    444
Cys Ser Glu Val Gly Pro Asp Arg Ser Thr Ser Ile Val Ala Val Met
    115                 120                 125

AAT TAC TTG CAG GAA GCT GCA TGT AAT CAT GCG GAG AGT CTG GGA CTT    492
Asn Tyr Leu Gln Glu Ala Ala Cys Asn His Ala Glu Ser Leu Gly Leu
130                 135                 140                 145
```

FIGURE 3 - B

```
CTA GGA GAT GGA TTC GGT GAG ACA CTA GAG ATG AGT AGG AGA GAT CTG    540
Leu Gly Asp Gly Phe Gly Glu Thr Leu Glu Met Ser Arg Arg Asp Leu
            150                 155                 160

ATA TGG GTT GTG AGA CGC ACG CAT GTT GTG GGA ACG TAC CCT GCT         588
Ile Trp Val Val Arg Arg Thr His Val Val Gly Thr Tyr Pro Ala
        165                 170                 175

TGG GGC GAT ACT GTT GAA GTC GAG GCC TGG ATC GGT GCA GCT GGA AAC    636
Trp Gly Asp Thr Val Glu Val Glu Ala Trp Ile Gly Ala Ala Gly Asn
            180                 185                 190

ATT GGC ATG CGC CGC CAT TTT CTT GTC CGC GAC TGC AAA ACT GGC CAC    684
Ile Gly Met Arg Arg His Phe Leu Val Arg Asp Cys Lys Thr Gly His
            195                 200                 205

ATT CTT GCA AGA TGT ACC AGT GTT TCA GTG ATG ATG AAT ATG AGG ACA    732
Ile Leu Ala Arg Cys Thr Ser Val Ser Val Met Met Asn Met Arg Thr
210             215                 220                 225
```

FIGURE 3 - C

```
AGG AGA TTG TCC AAA ATT CCC CAA GAA GTT AGA GGG GAG ATT GAC CCT    780
Arg Arg Leu Ser Lys Ile Pro Gln Glu Val Arg Gly Glu Ile Asp Pro
        230                 235                 240

CTT TTC ATC GAA AAG TTT GCT GTC AAG GAA GGG GAA ATT AAG AAA TTA    828
Leu Phe Ile Glu Lys Phe Ala Val Lys Glu Gly Glu Ile Lys Lys Leu
        245                 250                 255

CAG AAG TTC AAT GAT AGC ACT GCA GAT TAC ATT CAA GGG GGT TGG ACT    876
Gln Lys Phe Asn Asp Ser Thr Ala Asp Tyr Ile Gln Gly Gly Trp Thr
        260                 265                 270

CCG CGA TGG AAT GAT TTG GAT GTC AAT CAG CAC GTG AAC AAT ATC AAA    924
Pro Arg Trp Asn Asp Leu Asp Val Asn Gln His Val Asn Asn Ile Lys
        275                 280                 285

TAC GTT GGC TGG ATT TTT AAG AGC GTC CCA GAC TCT ATC TAT GAG AAT    972
Tyr Val Gly Trp Ile Phe Lys Ser Val Pro Asp Ser Ile Tyr Glu Asn
        290                 295                 300                 305
```

FIGURE 3 - D

```
CAT CAT CTT TCT AGC ATC ACT CTC GAA TAC AGG AGA GAG TGC ACA AGG   1020
His His Leu Ser Ser Ile Thr Leu Glu Tyr Arg Arg Glu Cys Thr Arg
            310                 315                 320

GGC AGA GCA CTG CAG TCC CTG ACC ACT GTT TGT GGT GGC TCG TCC GAA   1068
Gly Arg Ala Leu Gln Ser Leu Thr Thr Val Cys Gly Gly Ser Ser Glu
            325                 330                 335

GCT GGG ATC ATA TGT GAG CAC CTA CTC CAG CTT GAG GAT GGG TCT GAG   1116
Ala Gly Ile Ile Cys Glu His Leu Leu Gln Leu Glu Asp Gly Ser Glu
            340                 345                 350

GTT TTG AGG GGA AGA ACA GAT TGG AGG CCC AAG CGC ACC GAT AGT TTC   1164
Val Leu Arg Gly Arg Thr Asp Trp Arg Pro Lys Arg Thr Asp Ser Phe
            355                 360                 365

GAA GGC ATT AGT GAG AGA TTC CCG CAG CAA GAA CCG CAT AAT TAAT      1210
Glu Gly Ile Ser Glu Arg Phe Pro Gln Gln Glu Pro His Asn
            370                 375                 380
```

FIGURE 3 - E

```
GACAGAAGCA TCAGATATAG TTTCTCCTGT GCTGTTCCTG AGAATGCATC TTACAAGTCG  1270

TGGTTTGGAT TGCTTGTGCA GAATCATGGT TTGTGCTTTC AGAAGTATAT CTAAATTAGT  1330

CCAAGTTATA TGACTCCATA TTGGAAAATA ACTCAATGAG TCGTGCTCTT GAAATGGTCT  1390

TTTAAGCTTT GAAATAAAGT TCCACTTAAT CCATGTAAAA AAAAA                 1435
```

FIGURE 3 - F

```
GGGTAACATG GCATAAACGT GAATAACTGC AACTCCAGTG TCACTTTCCC TTTCCTTTCC     60

ACCACCATCT CCTCCCTCGG TCCCATCGAC GGCAAACTCC ATAAAACCAC CACCACCTCT    120

TCAAATCAAC ACCTCTTCCG AACCACCACC ACCACCACCG CCGCCGGCAA CT ATG CTA    178
                                                          Met Leu
                                                            1

TCA CGA CCT CTT CCG ACC ACC GCC GCG GCG ACC ACG ACG AAT              226
Ser Arg Pro Leu Pro Thr Thr Ala Ala Ala Thr Thr Thr Asn
          5                  10                  15

AAT TGC AAT GGC GTC AAC TCC CGC GGC GCC TTA CCT CAT TCC CGA TCC      274
Asn Cys Asn Gly Val Asn Ser Arg Gly Ala Leu Pro His Ser Arg Ser
 20                  25                  30

GTT GGA TTC GCC TCG ATT CGG AAA CGA AGC ACC GGT TCC TTA TGC AAT      322
Val Gly Phe Ala Ser Ile Arg Lys Arg Ser Thr Gly Ser Leu Cys Asn
 35                  40                  45                  50

FIGURE 4A-1
```

```
TCG CCG CGG ACG GTG GCG CCG GTG ATG GCG GTG AGG ACC GGT GAG    370
Ser Pro Arg Thr Val Ala Pro Val Met Ala Val Arg Thr Gly Glu
        55                  60                  65

CAA CCG ACC GGC GTT GCC GTC GGA TTG AAG GAG GCG GAG GCG GTG    418
Gln Pro Thr Gly Val Ala Val Gly Leu Lys Glu Ala Glu Ala Val
        70                  75                  80

GAG AAG AGC CTG GCG GAT CGG CTT CGG ATG GGG AGC TTG ACG GAA GAT 466
Glu Lys Ser Leu Ala Asp Arg Leu Arg Met Gly Ser Leu Thr Glu Asp
        85                  90                  95

GGA TTG TCG TAT AAG GAG AGG TTC ATC ATA AGG TGT TAT GAA GTC GGG 514
Gly Leu Ser Tyr Lys Glu Arg Phe Ile Ile Arg Cys Tyr Glu Val Gly
        100                 105                 110

ATT AAT AAG ACT GCA ACT GTT GAA ACC ATT GCT AAT CTA TTG CAG GAG 562
Ile Asn Lys Thr Ala Thr Val Glu Thr Ile Ala Asn Leu Leu Gln Glu
        115                 120                 125             130
```

FIGURE 4A-2

```
GTT GGA GGT AAT CAT GCT CAG AGT GTT GGA TTT TCA ACA GAC GGA TTT    610
Val Gly Gly Asn His Ala Gln Ser Val Gly Phe Ser Thr Asp Gly Phe
                135             140             145

GCC ACC ACG ACC ACT ATG CGA AAA TTG CAT CTC ATA TGG GTG ACT TCG    658
Ala Thr Thr Thr Thr Met Arg Lys Leu His Leu Ile Trp Val Thr Ser
                150             155             160

CGA ATG CAC ATT GAA ATT TAC AGA TAC CCC GCT TGG AGT GAT GTG GTT    706
Arg Met His Ile Glu Ile Tyr Arg Tyr Pro Ala Trp Ser Asp Val Val
                165             170             175

GAA ATC GAG ACT TGG TGT CAA AGT GAA GGA AGG ATT GGG ACT AGA CGT    754
Glu Ile Glu Thr Trp Cys Gln Ser Glu Gly Arg Ile Gly Thr Arg Arg
                180             185             190

GAT TGG ATT ATG AAA GAC CAT GCG AGT GGT GAA GTC ATT GGA AGG GCT    802
Asp Trp Ile Met Lys Asp His Ala Ser Gly Glu Val Ile Gly Arg Ala
195             200             205             210
```

FIGURE 4A-3

```
ACA AGC AAA TGG GTG ATG ATG AAC GAG GAT ACT AGA AGA CTC CAG AAA    850
Thr Ser Lys Trp Val Met Met Asn Glu Asp Thr Arg Arg Leu Gln Lys
        215                 220                 225

GTC AAC GAT GAC GTC AGA GAC GAA TAT CTC GTT TTT TGT CCC AAG ACA    898
Val Asn Asp Asp Val Arg Asp Glu Tyr Leu Val Phe Cys Pro Lys Thr
        230                 235                 240

CCA AGA TTA GCA TTT CCT GAA AAG AAC ACT AGC AGC CTG AAG AAA ATA    946
Pro Arg Leu Ala Phe Pro Glu Lys Asn Thr Ser Ser Leu Lys Lys Ile
        245                 250                 255

GCA AAA CTA GAA GAC CCC GCC GAA TAT TCG ACG CTA GGG CTT GTG CCA    994
Ala Lys Leu Glu Asp Pro Ala Glu Tyr Ser Thr Leu Gly Leu Val Pro
        260                 265                 270

AGA AGA GCC GAT CTC GAT ATG AAC AAG CAT GTT AAC AAT GTT ACC TAC    1042
Arg Arg Ala Asp Leu Asp Met Asn Lys His Val Asn Asn Val Thr Tyr
        275                 280                 285                 290
```

FIGURE 4A -4

```
ATT GGA TGG GTT CTT GAG AGC ATC CCA CAA GAA GTC ATC GAC ACT CAT   1090
Ile Gly Trp Val Leu Glu Ser Ile Pro Gln Glu Val Ile Asp Thr His
            295             300             305

GAA CTA CAA ACG ATT ACC CTA GAC TAC CGG GAA TGC CAG CAT GAC       1138
Glu Leu Gln Thr Ile Thr Leu Asp Tyr Arg Glu Cys Gln His Asp
310             315             320

GAC ATA GTC GAT TCC CTC ACG AGT TCC GAG TCA CTA CTC GAC GAT GCC   1186
Asp Ile Val Asp Ser Leu Thr Ser Ser Glu Ser Leu Leu Asp Asp Ala
        325             330             335

GCC ATC TCG AAA CTC GAA GGA ACC AAC GGA TCT GTT CCC AAA AAA       1234
Ala Ile Ser Lys Leu Glu Gly Thr Asn Gly Ser Val Pro Lys Lys
340             345             350                 Lys

GAC GAA ACG GAT TTG AGC CGG TTT CAT TTA CTA CGA TCA TCG GGC       1282
Asp Glu Thr Asp Leu Ser Arg Phe His Leu Leu Arg Ser Ser Gly
355             360             365             370
```

FIGURE 4A -5

```
GAT GGT CTC GAA CTA AAT AGG GGT CGC ACC GAG TGG AGA AAG AAA CCC     1330
Asp Gly Leu Glu Leu Asn Arg Gly Arg Thr Glu Trp Arg Lys Lys Pro
                375                         380                 385

GCG AAA AAA TGAGCAACAC CCTTCGGTTT GTTTAGCGTA CCCTTTTTG              1379
Ala Lys Lys

CGTGTTTTCA ATCCATTTTT CATAATTCGC CTTTTAGGGN NNNGCCGTTT TTATGTAGCG   1439

TATTTGTTGT AGATGGACTA GGTTTTCGGA TTCTCGAACC GGATAGGTGC TATCTTTATC   1499

TTCCTATGTT TTGCTTGTAG AATGGTATGA ATAAACTAGT TTCGAAGTAA TGTTTTTGGT   1559

```
GCACAAACCA GGAAAAAAAA AACCCTCTCT CCCTAACCTA ACTCGCCATC GGAGAAATCT       60

CTGTCGACGG TGACGTTCGA GATCGTAACA ATC ATG CTA TCG AAA GGT GCT CCG      114
                                 Met Leu Ser Lys Gly Ala Pro
                                  1               5

GCG GCA CCG GCG GTG GCG GCG ATG TAC AAT GCC TCC GCC AAA GAC ACT       162
Ala Ala Pro Ala Val Ala Ala Met Tyr Asn Ala Ser Ala Lys Asp Thr
          10                  15                  20

ACT TTT GCC CTA ACT CAC TCC CGA TCG ATT GGT TCC GTC TCA ATT CGC       210
Thr Phe Ala Leu Thr His Ser Arg Ser Ile Gly Ser Val Ser Ile Arg
         25                  30                  35

AGA CGA TAC AAC GTG TTT TGC AAT TCT TCG TCG TCG AGA AAG                258
Arg Arg Tyr Asn Val Phe Cys Asn Ser Ser Ser Ser Arg Lys
 40                  45                  50             55

GTT TCT CCG TTG CTA GCG GTG GCG ACC GGA GAG CAG CCG AGC GGT GTT       306
Val Ser Pro Leu Leu Ala Val Ala Thr Gly Glu Gln Pro Ser Gly Val
         60                  65                  70
```

```
GCT AGT TTA CGT GAG GCG GAT AAG GAG AAG AGC TTG GGG AAC CGG CTA   354
Ala Ser Leu Arg Glu Ala Asp Lys Glu Lys Ser Leu Gly Asn Arg Leu
         75                  80                  85

CGG TTG GGG AGC TTG ACG GAG GAT GGA TTA TCG TAT AAG GAG AAG TTC   402
Arg Leu Gly Ser Leu Thr Glu Asp Gly Leu Ser Tyr Lys Glu Lys Phe
         90                  95                 100

GTT ATA AGG TGT TAT GAA GTC GGA ATT AAC AAA ACT GCT ACG ATT GAA   450
Val Ile Arg Cys Tyr Glu Val Gly Ile Asn Lys Thr Ala Thr Ile Glu
        105                 110                 115

ACG ATT GCA AAT CTG TTG CAG GAG GTT GGA GGT AAT CAT GCT CAG GGT   498
Thr Ile Ala Asn Leu Leu Gln Glu Val Gly Gly Asn His Ala Gln Gly
        120                 125                 130                 135

GTT GGA TTT TCT ACT GAT GGG TTT GCC ACA ACG ACC ACT ATG AGG AAA   546
Val Gly Phe Ser Thr Asp Gly Phe Ala Thr Thr Thr Thr Met Arg Lys
        140                 145                 150
```

```
TTG CAT CTC ATA TGG GTT ACT GCA CGA ATG CAT ATT GAA ATA TAT AGA    594
Leu His Leu Ile Trp Val Thr Ala Arg Met His Ile Glu Ile Tyr Arg
        155                 160                 165

TAC CCT GCT TGG AGT GAT GTG ATT GAA ATT GAG ACT TGG GTT CAG GGT    642
Tyr Pro Ala Trp Ser Asp Val Ile Glu Ile Glu Thr Trp Val Gln Gly
    170                 175                 180

GAG GGG AAG GTC GGG ACC AGG CGT GAT TGG ATC CTC AAA GAC TAT GCC    690
Glu Gly Lys Val Gly Thr Arg Arg Asp Trp Ile Leu Lys Asp Tyr Ala
185                 190                 195

AAT GGT GAG GTT ATT GGA AGG GCC ACA AGC AAA TGG GTG ATG ATG AAC    738
Asn Gly Glu Val Ile Gly Arg Ala Thr Ser Lys Trp Val Met Met Asn
200                 205                 210                 215

GAG GAT ACT AGA AGA TTG CAG AAA GTC AGT GAT GAT GTC AGA GAG GAG    786
Glu Asp Thr Arg Arg Leu Gln Lys Val Ser Asp Asp Val Arg Glu Glu
        220                 225                 230
```

FIGURE 4B -3

```
TAT TTA GTG TTT TGC CCC AGG ACA TTG AGA TTA GCA TTT CCT GAA GAG    834
Tyr Leu Val Phe Cys Pro Arg Thr Leu Arg Leu Ala Phe Pro Glu Glu
        235                 240                 245

AAC AAT AGC ATG AAG AAA ATA CCA AAA CTG GAA GAT CCA GCT GAA        882
Asn Asn Ser Met Lys Lys Ile Pro Lys Leu Glu Asp Pro Ala Glu
    250                 255                 260

TAT TCC AGG CTT GGA CTT GTG CCA AGG AGA TCC GAT TTG GAT ATG AAC    930
Tyr Ser Arg Leu Gly Leu Val Pro Arg Arg Ser Asp Leu Asp Met Asn
265                 270                 275

AAA CAC GTT AAC AAT GTT ACC TAC ATC GGG TGG GCT CTA GAG AGC ATC    978
Lys His Val Asn Asn Val Thr Tyr Ile Gly Trp Ala Leu Glu Ser Ile
280                 285                 290                 295

CCA CCA GAA ATC ATC GAC ACC CAT GAA CTG CAA GCT ATT ACC TTA GAC    1026
Pro Pro Glu Ile Ile Asp Thr His Glu Leu Gln Ala Ile Thr Leu Asp
                300                 305                 310
```

FIGURE 4B-4

| | | | | | | | | | | | | | | | | |
|---|---|---|---|---|---|---|---|---|---|---|---|---|---|---|---|---|
| TAC | AGA | CGT | GAA | TGC | CAA | CGG | GAT | GAC | ATA | GTT | GAT | TCA | CTC | ACT | AGC | 1074 |
| Tyr | Arg | Arg | Glu | Cys | Gln | Arg | Asp | Asp | Ile | Val | Asp | Ser | Leu | Thr | Ser | |
| | | | 315 | | | | | 320 | | | | | 325 | | | |
| CGT | GAA | CCA | CTC | GGA | AAT | GCT | GCA | GGT | GTC | AAG | TTT | AAA | GAA | ATC | AAT | 1122 |
| Arg | Glu | Pro | Leu | Gly | Asn | Ala | Ala | Gly | Val | Lys | Phe | Lys | Glu | Ile | Asn | |
| | 330 | | | | | 335 | | | | | 340 | | | | | |
| GGA | TCT | GTT | TCC | CCC | AAA | AAG | GAC | GAA | CAA | GAT | CTA | AGC | CGA | TTT | ATG | 1170 |
| Gly | Ser | Val | Ser | Pro | Lys | Lys | Asp | Glu | Gln | Asp | Leu | Ser | Arg | Phe | Met | |
| 345 | | | | | 350 | | | | | 355 | | | | | | |
| CAT | CTA | CTG | AGA | TCA | GCT | GGC | AGT | GGT | CTT | GAA | ATC | AAC | AGG | TGT | CGC | 1218 |
| His | Leu | Leu | Arg | Ser | Ala | Gly | Ser | Gly | Leu | Glu | Ile | Asn | Arg | Cys | Arg | |
| 360 | | | | | 365 | | | | | 370 | | | | | 375 | |
| ACC | GAA | TGG | AGA | AAG | AAG | CCA | GCA | AAA | AGA | TAAGCATATC | | | TGATCCCTCG | | | 1268 |
| Thr | Glu | Trp | Arg | Lys | Lys | Pro | Ala | Lys | Arg | | | | | | | |
| | | | 380 | | | | | 385 | | | | | | | | |

ATTGTACCGT TTTACCGTTC CTGTTCAAAG TCTAGTTTCT TTTT    1312

FIGURE 4B -5

```
GGATCCATTA GCAGGTAGGA GGTCGGACCT GACCGCTCCA CATCTATAGT GGCTGTTATG  60

AATCACTTGC AGGAGGCTGC ACTTAATCAT GCGAAGAGTG TGGGAATTCT AGGAGATGA  120

TTCGGTACGA CGCTAGAGAT GAGTAAGAGA GATCTGATAT GGGTTGTGAA ACGCACGCAT 180

GTTGCTGTGG AACGGTACCC TGCTTGGGGT GATACTGTTG AAGTAGAGTG CTGGGTTGGT 240

GCATCGGGAA ATAATGGCAG GCGCCATGAT TTCCTTGTCC GGGACTGCAA AACAGGCGAA 300

ATTCTTACAA GATGTACCAG TCTTTCGGTG ATGATGAATA CAAGGACAAG GAGGTTGTCC 360

AAAATCCCTG AAGAAGTTAG AGGGGAGATA GGGCCTGCAT TCATTGATAA TGTGGCTGTC 420

AAGGACGAGG AAATTAAGAA ACCACAGAAG CTCAATGACA GCACTGCAGA TTACATCCAA 480

GGAGGATTGA CTCCCTCGATG GAATGATTTG GATATCAATA AGCATGTCAA CAACCTCGAG 540
```

FIGURE 5A

```
TCAAC ATG GCC ACC ACC TCT TTA GCT TCT GCT TTC TGC TCG ATG AAA GCT       50
      Met Ala Thr Thr Ser Leu Ala Ser Ala Phe Cys Ser Met Lys Ala
       1                   5                  10                  15

GTA ATG TTG GCT CGT GAT GGC AGG GGC ATG AAA CCC AGG AGC AGT GAT         98
Val Met Leu Ala Arg Asp Gly Arg Gly Met Lys Pro Arg Ser Ser Asp
                 20                  25                  30

TTG CAG CTG AGG GCG GGA AAT GCA CAA ACC TCT TTG AAG ATG ATC AAT        146
Leu Gln Leu Arg Ala Gly Asn Ala Gln Thr Ser Leu Lys Met Ile Asn
             35                  40                  45

GGG ACC AAG TTC AGT TAC ACA GAG AGC TTG AAA AAG TTG CCT GAC TGG        194
Gly Thr Lys Phe Ser Tyr Thr Glu Ser Leu Lys Lys Leu Pro Asp Trp
         50                  55                  60

AGC ATG CTC TTT GCA GTG ATC ACC ATC TTT TCG GCT GCT GAG AAG            242
Ser Met Leu Phe Ala Val Ile Thr Ile Phe Ser Ala Ala Glu Lys
     65                  70                  75

CAG TGG ACC AAT CTA GAG TGG AAG CCG AAT CCA CCC CAG TTG                290
Gln Trp Thr Asn Leu Glu Trp Lys Pro Lys Pro Asn Pro Pro Gln Leu
 80                  85                  90                  95
```

FIGURE 5B-1

```
CTT GAT GAC CAT TTT GGG CCG CAT GGG TTA GTT TTC AGG CGC ACC TTT    338
Leu Asp Asp His Phe Gly Pro His Gly Leu Val Phe Arg Arg Thr Phe
            100                 105                 110

GCC ATC AGA TCG TAT GAG GTG GGA CCT GAC CGC TCC ACA TCT ATA GTG    386
Ala Ile Arg Ser Tyr Glu Val Gly Pro Asp Arg Ser Thr Ser Ile Val
            115                 120                 125

GCT GTT ATG AAT CAC TTG CAG GAG GCT GCA CTT AAT CAT GCG AAG AGT    434
Ala Val Met Asn His Leu Gln Glu Ala Ala Leu Asn His Ala Lys Ser
            130                 135                 140

GTG GGA ATT CTA GGA GAT GGA TTC GGT ACG ACG CTA GAG ATG AGT AAG    482
Val Gly Ile Leu Gly Asp Gly Phe Gly Thr Thr Leu Glu Met Ser Lys
            145                 150                 155

AGA GAT CTG ATA TGG GTT GTG AAA CGC ACG CAT GTT GCT GTG GAA CGG    530
Arg Asp Leu Ile Trp Val Val Lys Arg Thr His Val Ala Val Glu Arg
            160                 165                 170                 175
```

FIGURE 5B-2

| | | | | | | | | | | | | | | | |
|---|---|---|---|---|---|---|---|---|---|---|---|---|---|---|---|
| TAC | CCT | GCT | TGG | GGT | GAT | ACT | GTT | GAA | GTA | GAG | TGC | TGG | GTT | GGT | GCA |
| Tyr | Pro | Ala | Trp | Gly | Asp | Thr | Val | Glu | Val | Glu | Cys | Trp | Val | Gly | Ala |
| | | | 180 | | | | | 185 | | | | | | 190 | |

578

| | | | | | | | | | | | | | | | |
|---|---|---|---|---|---|---|---|---|---|---|---|---|---|---|---|
| TCG | GGA | AAT | AAT | GGC | AGG | CGC | CAT | GAT | TTC | CTT | GTC | CGG | GAC | TGC | AAA |
| Ser | Gly | Asn | Asn | Gly | Arg | Arg | His | Asp | Phe | Leu | Val | Arg | Asp | Cys | Lys |
| | | | 195 | | | | | 200 | | | | | | 205 | |

626

| | | | | | | | | | | | | | | | |
|---|---|---|---|---|---|---|---|---|---|---|---|---|---|---|---|
| ACA | GGC | GAA | ATT | CTT | ACA | AGA | TGT | ACC | AGT | CTT | TCG | GTG | ATG | ATG | AAT |
| Thr | Gly | Glu | Ile | Leu | Thr | Arg | Cys | Thr | Ser | Leu | Ser | Val | Met | Met | Asn |
| | | | 210 | | | | | 215 | | | | | | 220 | |

674

| | | | | | | | | | | | | | | | |
|---|---|---|---|---|---|---|---|---|---|---|---|---|---|---|---|
| ACA | AGG | ACA | AGG | AGG | TTG | TCC | AAA | ATC | CCT | GAA | GAA | GTT | AGA | GGG | GAG |
| Thr | Arg | Thr | Arg | Arg | Leu | Ser | Lys | Ile | Pro | Glu | Glu | Val | Arg | Gly | Glu |
| | | | 225 | | | | | 230 | | | | | | 235 | |

722

| | | | | | | | | | | | | | | | |
|---|---|---|---|---|---|---|---|---|---|---|---|---|---|---|---|
| ATA | GGG | CCT | GCA | TTC | ATT | GAT | AAT | GTG | GCT | GTC | AAG | GAC | GAG | GAA | ATT |
| Ile | Gly | Pro | Ala | Phe | Ile | Asp | Asn | Val | Ala | Val | Lys | Asp | Glu | Glu | Ile |
| | | | 240 | | | | | 245 | | | | | | 250 | 255 |

```
AAG AAA CCA CAG AAG CTC AAT GAC AGC ACT GCA GAT TAC ATC CAA GGA         818
Lys Lys Pro Gln Lys Leu Asn Asp Ser Thr Ala Asp Tyr Ile Gln Gly
            260                 265                 270

GGA TTG ACT CCT CGA TGG AAT GAT TTG GAT ATC AAT CAG CAC GTT AAC         866
Gly Leu Thr Pro Arg Trp Asn Asp Leu Asp Ile Asn Gln His Val Asn
            275                 280                 285

AAC ATC AAA TAC GTT GAC TGG ATT CTT GAG ACT GTC CCA GAC TCA ATC         914
Asn Ile Lys Tyr Val Asp Trp Ile Leu Glu Thr Val Pro Asp Ser Ile
            290                 295                 300

TTT GAG AGT CAT CAT ATT TCC AGC TTC ACT ATT GAA TAC AGG AGA GAG         962
Phe Glu Ser His His Ile Ser Ser Phe Thr Ile Glu Tyr Arg Arg Glu
            305                 310                 315

TGC ACG ATG GAT AGC GTG CTG CAG TCC CTG ACC ACT GTC TCC GGT GGC        1010
Cys Thr Met Asp Ser Val Leu Gln Ser Leu Thr Thr Val Ser Gly Gly
            320                 325                 330             335
```

FIGURE 5B-4

```
TCG TCG GAA GCT GGG TTA GTG TGC GAG CAC TTG CTC CAG CTT GAA GGT    1058
Ser Ser Glu Ala Gly Leu Val Cys Glu His Leu Leu Gln Leu Glu Gly
            340                 345                 350

GGG TCT GAG GTA TTG AGG GCA AAA ACA GAG TGG AGG CCT AAG CTT ACC    1106
Gly Ser Glu Val Leu Arg Ala Lys Thr Glu Trp Arg Pro Lys Leu Thr
        355                 360                 365

GAT AGT TTC AGA GGG ATT AGT GTG ATA CCC GCA GAA TCG AGT GTC        1151
Asp Ser Phe Arg Gly Ile Ser Val Ile Pro Ala Glu Ser Ser Val
        370                 375                 380

TAACTAACGA AAGAAGCATC TGATGAAGTT TCTCCCTGTGC TGTTGTTCGT GAGGATGCTT  1211

TTTAGAAGCT GCAGTTTGCA TTGCTTGTGC AGAATCATGG CCTGTGGTTT TAGATATATA  1271

TCCAAAATTG TCCTATAGTC AAGAAACTTA ATATCAGAAA AATAACTCAA TGAGTCAAGG  1331
```

FIGURE 5B-5

```
TTATCGAAGT AGTCATGTAA GCTTTGAAAT ATGTTGTGTA TTCCTCGGCT TTATGTAATC  1391

TGTAAGCTCT TTCTCTTGCA ATAAATTTCG CCTTTCAATA ATAAAAAAAA AAAAAAAAGG  1451

TCGACTCGAG  1461
```

FIGURE 5B -6

```
GCTCGCCTCC CACATTTTCT TCTTCGATCC CGAAAAG ATG TTG AAG CTC TCG TGT       55
                                         Met Leu Lys Leu Ser Cys
                                          1               5

AAT GCG ACT GAT AAG TTA CAG ACC CTC TTC TCG CAT TCT CAT CAA CCG       103
Asn Ala Thr Asp Lys Leu Gln Thr Leu Phe Ser His Ser His Gln Pro
             10                  15                  20

GAT CCG GCA CAC CGG AGA ACC GTC TCC TCC GTG TCG TGC TCT CAT CTG       151
Asp Pro Ala His Arg Arg Thr Val Ser Ser Val Ser Cys Ser His Leu
         25                  30                  35

AGG AAA CCG GTT CTC GAT CCT TTG CGA GCG ATC GTA TCT GCT GAT CAA       199
Arg Lys Pro Val Leu Asp Pro Leu Arg Ala Ile Val Ser Ala Asp Gln
     40                  45                  50

GGA AGT GTG ATT CGA GCA GAA CAA GGT TTG GGC TCA CTC GCG GAT CAG       247
Gly Ser Val Ile Arg Ala Glu Gln Gly Leu Gly Ser Leu Ala Asp Gln
 55                  60                  65                  70

CTC CGA TTG GGT AGC GAG GAT TTG ACG TTG TCG TAT AAG GAG AAG           295
Leu Arg Leu Gly Ser Asp Glu Asp Leu Thr Leu Ser Tyr Lys Glu Lys
             75                  80                  85

TTC ATC GTC AGA TCC TAC GAA GTG GGG AGT AAC AAG ACC GCC ACT GTC       343
Phe Ile Val Arg Ser Tyr Glu Val Gly Ser Asn Lys Thr Ala Thr Val
         90                  95                 100
```

```
GAA ACC GTC GCT AAT CTT TTG CAG GAG GTG GGA TGT AAT CAT GCG CAG    391
Glu Thr Val Ala Asn Leu Leu Gln Glu Val Gly Cys Asn His Ala Gln
        105             110             115

AGC GTT GGA TTC TCG ACT GAT GGG TTT GCG ACA ACA CCG ACC ATG AGG    439
Ser Val Gly Phe Ser Thr Asp Gly Phe Ala Thr Thr Pro Thr Met Arg
        120             125             130

AAA CTG CAT CTC ATT TGG GTC ACT GCG AGA ATG CAT ATA GAG ATC TAC    487
Lys Leu His Leu Ile Trp Val Thr Ala Arg Met His Ile Glu Ile Tyr
        135             140             145             150

AAG TAC CCT GCT TGG GGT GAT GTG GTT GAG ATA GAG ACA TGG TGT CAG    535
Lys Tyr Pro Ala Trp Gly Asp Val Val Glu Ile Glu Thr Trp Cys Gln
        155             160             165

AGT GAA GGA AGG ATC GGG ACT AGG CGT GAT TGG ATT CTT AAG GAT GTT    583
Ser Glu Gly Arg Ile Gly Thr Arg Arg Asp Trp Ile Leu Lys Asp Val
        170             175             180

GCT ACG GGT GAA GTC ACT GCT CGT ACA AGC AAG TGG GTG ATG ATG        631
Ala Thr Gly Glu Val Thr Ala Arg Thr Ser Lys Trp Val Met Met
        185             190             195

AAC CAA GAC ACA AGA CGG CTT CAG AAA GTT TCT GAT GAT GTT CGG GAC    679
Asn Gln Asp Thr Arg Arg Leu Gln Lys Val Ser Asp Asp Val Arg Asp
        200             205             210
```

```
GAG TAC TTG GTC TTC TGT CCT AAA GAA CTC AGA TTA GCA TTT CCT GAG      727
Glu Tyr Leu Val Phe Cys Pro Lys Glu Leu Arg Leu Ala Phe Pro Glu
215                 220                 225                 230

GAG AAT AAC AGA AGC TTG AAG AAA ATT CCG AAA CTC GAA GAT CCA GCT      775
Glu Asn Asn Arg Ser Leu Lys Lys Ile Pro Lys Leu Glu Asp Pro Ala
        235                 240                 245

CAG TAT TCG ATG ATT GGG CTT AAG CCT AAG AGA CGA GCT GAT CTC ATG      823
Gln Tyr Ser Met Ile Gly Leu Lys Pro Lys Arg Arg Ala Asp Leu Met
            250                 255                 260

AAC CAG CAT GTC AAT AAT GTC ACC TAT ATT GGA TGG GTT CTT GAG AGC      871
Asn Gln His Val Asn Asn Val Thr Tyr Ile Gly Trp Val Leu Glu Ser
                265                 270                 275

ATA CCT CAA GAG ATT GTA GAC ACG CAC GAA CTT CAG GTC ATA ACT CTG      919
Ile Pro Gln Glu Ile Val Asp Thr His Glu Leu Gln Val Ile Thr Leu
        280                 285                 290

GAT TAC AGA AGA GAA TGT CAA CAA GAC GAT GTG GTG GAT TCA CTC ACC      967
Asp Tyr Arg Arg Glu Cys Gln Gln Asp Asp Val Val Asp Ser Leu Thr
            295                 300                 305         310

ACT ACC ACC TCA GAG ATT GGT GGG ACC AAT GGC TCT GCA TCA TCA GGC     1015
Thr Thr Thr Ser Glu Ile Gly Gly Thr Asn Gly Ser Ala Ser Ser Gly
                315                 320                 325
```

FIGURE 6C

```
ACA CAG GGG CAA AAC GAT AGC CAG TTC TTA CAT CTC TTA AGG CTG TCT    1063
Thr Gln Gly Gln Asn Asp Ser Gln Phe Leu His Leu Leu Arg Leu Ser
            330                     335                     340

GGA GAC GGT CAG GAG ATC AAC CGC GGG ACA ACC CTG TGG AGA AAG AAG    1111
Gly Asp Gly Gln Glu Ile Asn Arg Gly Thr Thr Leu Trp Arg Lys Lys
            345                     350                     355

CCC TCC AAT CTC TAAGCCATTT CGTTCTTAAG TTTCCTCTAT CTGTGTCGCT        1163
Pro Ser Asn Leu
        360

CGATGCTTCA CGAGTCTAGT CAGGTCTCAT TTTTTTCAAT CTAAAATTGG GTTAGACTAG  1223

AGAACTGGAA TTATTGGAAT TTATGAGTTT TCGTTCTTGT TTCTGTACAA ATCTTGAGGA  1283

TTGAAGCCAA ACCCATTTCA TCTT                                        1307
```

FIGURE 6D

```
SAFFLOWER   61 avatgeqpsgvasLreadKeKsLgnrLrlgsltedGLsykekFvIRcYEVGinktatIeti
                            |    | | |   |        ||     | || ||||      |
BAY         84              LewkpKpK L pqLlddhfglhGLvfrrtFaIRsYEVGpdrstsIlav SAFFLOWER  122 aNllQEvggNHAqgVGfstDGFaTTttMrKlhLiWVtaRmHieiyRYPaWsDviEiEtWvq
                |  ||   |||  ||   ||| ||  | |  | ||  | |    ||| | |  | | |
BAY        130 mNhmQEatlNHAksVGilgDGFgTTleMsKrdLmWVvrRtHvaveRYPtWgDtvEvEcWig SAFFLOWER  183 geGkvGtRRDwilkDyanGEvigRaTSkwVmMNedTRRLqkvsDdVReEylvfcPrtlrla
                 |  | |||    |   ||   | ||  | ||  ||||    | || |     |
BAY        191 asGnnGmRRDflvrDcktGEiltRcTSlsVlMNtrTRRLstipDeVRgE   igP afidn SAFFLOWER  244 fpeennnsmKkipkledpAeYsrlGLvPRrsDLDmNkHVNNvtYigWalEsiPpeIidtHe
                        |        | |   || ||  ||| | ||||  |  |  |  |  |   |
BAY        248 vavkddeikKlqklndstAdYiqgGLtPRwnDLDvNqHVNNlkYvaWvfEtvPdsIfesHh SAFFLOWER  305 lqaiTLdYRRECqRDdivdSLTsreplgnaAGvkfkeingsvspkkdEqdLsRfmhllRsa
                   || ||||| ||    |||        ||               |  | |     |
BAY        309 issfTLeYRRECtRDsvlrSLTtvsggsseAG  lvcdhllqleggsE vL RartewR SAFFLOWER  366 gsgleinRcrtewrkkPakr
                      |        |
BAY        364 pkltdsfRgisvipaePrv
```

```
TGGATCC AAT CAA CAT GTC AAC AAT GTG AAA TAC ATT GGG TGG ATT CTC    49
        Asn Gln His Val Asn Asn Val Lys Tyr Ile Gly Trp Ile Leu
         1               5                  10

AAG AGT GTT CCA ACA AAA GTT TTC GAG ACC CAG GAG TTA TGT GGC GTC    97
Lys Ser Val Pro Thr Lys Val Phe Glu Thr Gln Glu Leu Cys Gly Val
 15              20                  25                  30

ACC CTC GAG TAC CGG CGG GAA TGC TCGAG                             126
Thr Leu Glu Tyr Arg Arg Glu Cys
             35
```

PLANT THIOESTERASES AND USE FOR MODIFICATION OF FATTY ACID COMPOSITION IN PLANT SEED OILS

This application is a continuation of application Ser. No. 08/142,473 filed Nov. 18, 1993, now U.S. Pat. No. 5,639,790.

BACKGROUND

Members of several plant familes synthesize large amount of predominantly medium-chain (C8–C14) triacylglycerols in specialized storage tissues, some of which are harvested for production of important dietary or industrial medium-chain fatty acids (F. D. Gunstone, *The Lipid Handbook* (Chapman & Hall, New York, 1986) pp. 55–112). Laurate (C12:0), for example, is currently extracted from seeds of tropical trees at a rate approaching one million tons annually (Battey, et al., *Tibtech* (1989) 71:122–125).

The mechanism by which the ubiquitous long-chain fatty acid synthesis is switched to specialized medium-chain production has been the subject of speculation for many years (Harwood, *Ann. Rev. Plant Physiol. Plant Mol. Biology* (1988) 39:101–138). Recently, Pollard, et al., (*Arch. of Biochem. and Biophys.* (1991) 284:1–7) identified a medium-chain acyl-ACP thioesterase activity in developing oilseeds of California bay, *Umbellularia californica*. This activity appears only when the developing cotyledons become committed to the near-exclusive production of triglycerides with lauroyl (12:0) and caproyl (10:0) fatty acids. This work presented the first evidence for a mechanism for medium-chain fatty acid synthesis in plants: During elongation the fatty acids remain esterified to acyl-carrier protein (ACP). If the thioester is hydrolized prematurely, elongation is terminated by release of the medium-chain fatty acid. The Bay thioesterase was subsequently purified by Davies et al., (*Arch. Biochem. Biophys.* (1991) 290:37–45) which allowed the cloning of a corresponding cDNA and described it use to obtain related clones and to modify the triglyceride composition of plants (WO 91/16421).

SUMMARY OF THE INVENTION

By this invention, further properties and uses of plant medium-chain thioesterases are provided.

In a first embodiment, this invention relates to plant seed and oil derived from that seed, which normally do not contain laurate, but now are found to contain laurate. Seed having as little as 1.0 percent mole laurate are significantly different from wild-type plant species which do not naturally store laurate in seed triglyceride oils. Seed having a minimum of about 15 percent mole laurate, 33 percent laurate or 50 percent laurate are contemplated hereunder. Triglyceride oils in seed or derived from seed with at least two lauroyl fatty acyl groups is likewise contemplated. Brassica seed and oil derived from such seed containing greater than 1.0 percent mole laurate is especially preferred.

In yet a different embodiment, this invention relates to a particular medium-chain thioesterase sequence, the Bay medium-chain thioesterase DNA sequence and to DNA constructs for the expression of this enzyme in a host cell. In particular, a start site for the structural gene sequence upstream to the start site previously reported for this sequence is described.

Other aspects of this invention relate to methods for using a plant medium-chain thioesterase. Expression of a plant medium-chain thioesterase in a bacterial cell to produce medium-chain fatty acids is provided. By this method, quantities of such fatty acids may be harvested in crystalline form from bacteria. Exemplified in the application is the use of *E. coli* and Bay thioesterase; the fad D *E. coli* mutant is particularly preferred. In addition, temperature ranges for improved laurate production are described.

Methods to produce an unsaturated medium-chain thioesterase by the use of a plant medium-chain thioesterase are also described herein. It is now found that, even in plants which exclusively produce and incorporate quantities of saturated medium-chain acyl-ACP fatty acids into triglycerides, the thioesterase may have activity against unstaturated fatty acids of the same length.

DESCRIPTION OF THE FIGURES

FIGS. 1A–1B. The full length of a bay thioesterase (pCGN3822) having an ATG codon at nucleotides 145–147 is given. In 1A the nucleic acid sequence (SEQ ID NO: 1) is given. In 1B, the translated amino acid sequence (SEQ ID NO: 2) beginning at the ATG codon at nucleotides 145–147 is given.

FIGS. 3A–3F. Nucleic acid and translated amino acid sequence of a bay thioesterase clone, Bay D (SEQ ID NO: 3) which represents a second class of bay thioesterase genes, is presented.

FIGS. 4A–4B. Nucleic acid and translated amino acid sequences of two safflower thioesterase clones, pCGN3264 (4A) (SEQ ID NO: 4) and pCGN3265 (4B) (SEQ ID NO: 5), is presented.

FIGS. 5A–B. Nucleic acid sequence of a camphor thioesterase PCR fragment is presented in FIG. 5A (SEQ ID NO. 6). Nucleic acid and translated amino acid sequences of a camphor PCR-generated thioesterase encoding sequence is presented in FIG. 5B (SEQ ID NO: 7). FIGS. 6A–6D. Nucleic acid sequence of a *Brassica campestris* thioesterase clone (SEQ ID NO: 8) is presented in FIGS. 6A–6D. Translated amino acid sequence from the proposed MET initiation codon is also shown.

FIG. 8. Comparison of safflower and bay thioesterase amino acid sequence is presented. The top line represents amino acids 61–385 of the safflower thioesterase amino acid sequence (SEQ ID NO: 9) in FIG. 4B. The bottom line represents amino acids 84–382 of the bay thioesterase amino acid sequence (SEQ ID NO: 10) in FIG. 1B.

In Figure 10B, the content of C18:3, C18:2 and C16:0 fatty acids in these plants are shown.

FIG. 12. DNA sequence of a PCR fragment of a Cuphea thioesterase gene (SEQ ID NO: 11) is presented. Translated amino acid sequence in the region corresponding to the Cuphea thioesterase gene is also shown.

DETAILED DESCRIPTION OF THE INVENTION

Figure 2:
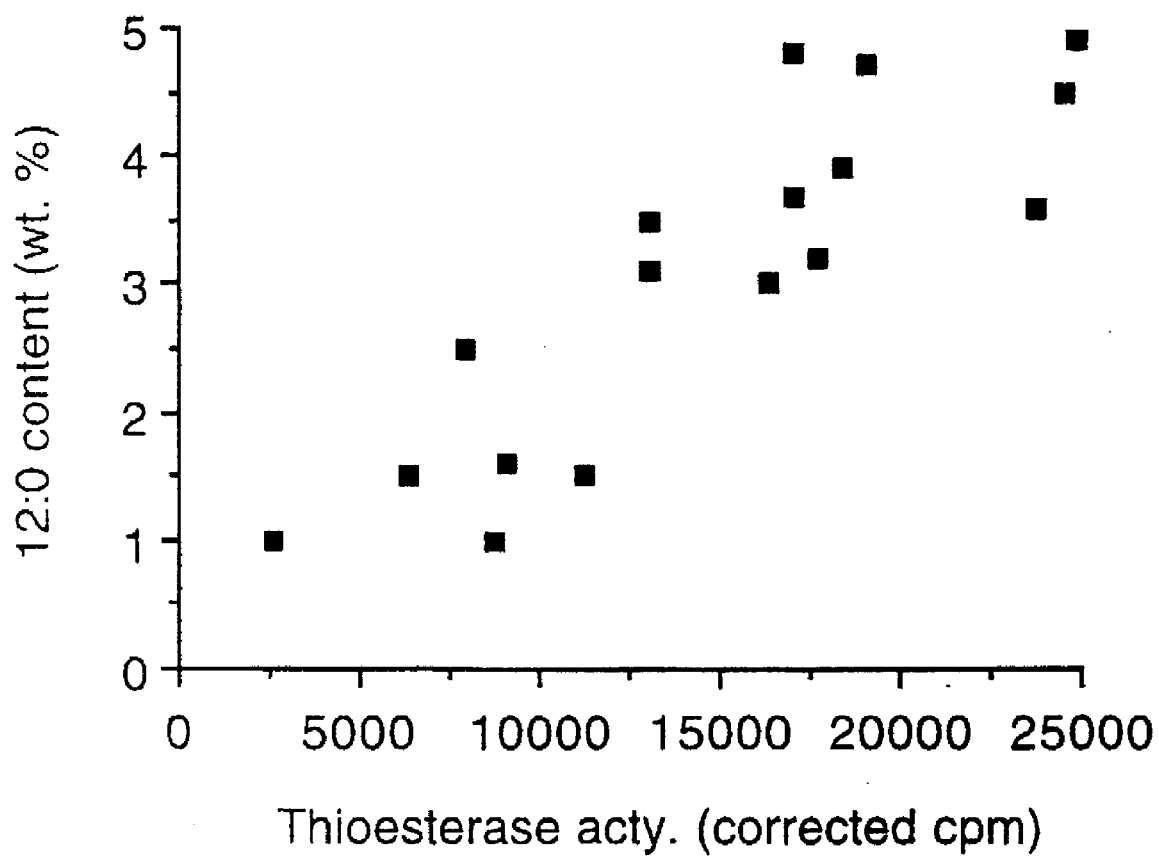
FIG. 2. Correlation of lauroyl thioesterase activity with the accumulation of acyl 12:0 in seeds of A thaliana is provided. Thioesterase activity is measured in developing seeds of different independent transgenic plants. The % 12:0 value reflects the percent lauroyl acyl group in total fatty acid extracts, as measured by quantitative gas chromatography.

Plant thioesterases, including medium-chain plant thioesterases are described in WO 91/16421 (PCT/US91/02960) and U.S. Pat. No. 5,512,482 which are hereby incorporated by reference in their entirety.

A plant medium-chain thioesterase of this invention includes any sequence of amino acids, peptide, polypeptide or protein obtainable from a plant source which demonstrates the ability to catalyze the production of free fatty acid(s) from C8–C14 fatty acyl-ACP substrates under plant enzyme reactive conditions. By "enzyme reactive conditions" is meant that any necessary conditions are available in an environment (i.e., such factors as temperature, pH, lack of inhibiting substances) which will permit the enzyme to function.

Plant thioesterases are obtainable from the specific exemplified sequences provided herein and from related sources. For example, several species in the genus Cuphea accumulate triglycerides containing medium-chain fatty acids in their seeds, e.g., procumbens, lutea, hookeriana, hyssopifolia, wrightii and inflata. Another natural plant source of medium-chain fatty acids are seeds of the Lauraceae family: e.g., Pisa (*Actinodophne hookeri*) and Sweet Bay (*Laurus nobilis*). Other plant sources include Ulmaceae (elm), Myristicaceae, Simarubaceae, Vochysiaceae, and Salvadoraceae, and rainforest species of Erisma, Picramnia and Virola, which have been reported to accumulate C14 fatty acids.

As noted above, plants having significant presence of medium-chain fatty acids therein are preferred candidates to obtain naturally-derived medium-chain preferring plant thioesterases. However, it should also be recognized that other plant sources which do not have a significant presence of medium-chain fatty acids may be readily screened as other enzyme sources. In addition, a comparison between endogenous medium-chain preferring plant thioesterases and between longer and/or shorter chain preferring plant thioesterases may yield insights for protein modeling or other modifications to create synthetic medium-chain preferring plant thioesterases as well as discussed above.

One skilled in the art will readily recognize that antibody preparations, nucleic acid probes (DNA and RNA) and the like may be prepared and used to screen and recover "homologous" or "related" thioesterases from a variety of plant sources. For immunological screening methods, antibody preparations either monoclonal or polyclonal are utilized. For detection, the antibody is labeled using radioactivity or any one of a variety of second antibody/enzyme conjugate systems that are commercially available. Examples of some of the available antibody detection systems are described by Oberfilder (*Focus* (1989) BRL Life Technologies, Inc., 11:1–5).

Homologous sequences are found when there is an identity of sequence, which may be determined upon comparison of sequence information, nucleic acid or amino acid, or through hybridization reactions between a known thioesterase and a candidate source. Conservative changes, such as Glu/Asp, Val/Ile, Ser/Thr, Arg/Lys and Gln/Asn may also be considered in determining amino acid sequence homology. Amino acid sequences are considered homologous by as little as 25% sequence identity between the two complete mature proteins. (See generally, Doolittle, R. F., OF URFS and ORFS (University Science Books, Calif., 1986.) Typically, a lengthy nucleic acid sequence may show as little as 50–60% sequence identity, and more preferably at least about 70% sequence identity, between the target sequence and the given plant thioesterase of interest excluding any deletions which may be present, and still be considered related.

A genomic or other appropriate library prepared from the candidate plant source of interest may be probed with conserved sequences from plant thioesterase to identify homologously related sequences. Shorter probes are often particularly useful for polymerase chain reactions (PCR), especially when highly conserved sequences can be identified.

When longer nucleic acid fragments are employed (>100 bp) as probes, especially when using complete or large cDNA sequences, one would screen with low stringencies (for example 40°–50° C. below the melting temperature of the probe) in order to obtain signal from the target sample with 20–50% deviation, i.e., homologous sequences. (See, Beltz, et al. *Methods in Enzymology* (1983) 100:266–285.).

Using methods known to those of ordinary skill in the art, a DNA sequence encoding a plant medium-chain thioesterase can be inserted into constructs which can be introduced into a host cell of choice for expression of the enzyme, including plant cells for the production of transgenic plants. Thus, potential host cells include both prokaryotic and eukaryotic cells. A host cell may be unicellular or found in a multicellar differentiated or undifferentiated organism depending upon the intended use. Cells of this invention may be distinguished by having a plant thioesterase foreign to the wild-type cell present therein, for example, by having a recombinant nucleic acid construct encoding a plant thioesterase therein.

Also, depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Among transcriptional initiation regions which have been described are regions from bacterial and yeast hosts, such as *E. coli, B. subtilis, Sacchromyces cerevisiae*, including genes such as beta-galactosidase, T7 polymerase, tryptophan E and the like.

For the most part, when expression in a plant host cell is desired, the constructs will involve regulatory regions (promoters and termination regions) functional in plants. The open reading frame, coding for the plant thioesterase or functional fragment thereof will be joined at its 5' end to a transcription initiation regulatory region such as the wild-type sequence naturally found 5' upstream to the thioesterase structural gene. Numerous other transcription initiation regions are available which provide for a wide variety of constitutive or regulatable, e.g., inducible, transcription of the structural gene functions. Among transcriptional initiation regions used for plants are such regions associated with the structural genes such as for CaMV 35S and nopaline and mannopine synthases, or with napin, ACP promoters and the like. The transcription/translation initiation regions corresponding to such structural genes are found immediately 5' upstream to the respective start codons. If a particular promoter is desired, such as a promoter native to the plant host of interest or a modified promoter, i.e., having transcription initiation regions derived from one gene source and translation initiation regions derived from a different gene source, including the sequence encoding the plant thioesterase of interest, or enhanced promoters, such as double 35S CaMV promoters, the sequences may be joined together using standard techniques. For most applications desiring the expression of medium-chain thioesterases in plants, the use of seed specific promoters are preferred. It is now observed that such a plant medium-chain thioesterase is biologically active when expressed in bacteria and heterologous plant cells.

In particular, it is now seen that plant seed which would not normally contain medium-chain fatty acid, either as free fatty acids or incorporated into triglyceride molecules, can be found to contain such medium-chain fatty acids. By seed which would not normally contain medium-chain fatty acid is meant seed which contains less than 0.1 mole percent of a given medium-chain fatty acid in total fatty acids. Thus, any plant seed containing a minimum of 1.0 mole percent of a given medium-chain fatty acid in total fatty acids is significantly modified. The use of a "mole percent in total fatty acids" is used to describe the relative ratio of medium-chain fatty acids out of the total fatty acid content. These figures can be converted to weight percent if desired.

Medium chain fatty acid contents from a minimum of 1.0 mole percent laurate in total fatty acids to a minimum of 50.0 mole percent laurate in total fatty acids have been measured. The total fatty acids of a plant seed include the embryo, endosperm and seed coat lipids. Additionally, it is noted that in medium-chain fatty acid containing seed, the content of laurate in total fatty acids directly corresponded with the laurate contents of the triacylglyceride. Thus, it is appropriate to consider the total fatty acid content as the "total extractable oils" as well.

As to triacylglycerides which incorporate the medium-chain fatty acids, it is not clear which positions of the glycerol backbone are involved. Based upon the high levels of medium-chain fatty acids measured, however, it is apparent that at least two positions of the triacylglyceride are involved.

Medium chain containing seed of Arabidopsis and Brassica are exemplified herein. In particular, seed of transgenic Arabidposis and Brassica plants containing novel fatty acid compositions as the result of expression of a heterologous medium-chain thioestesterase structural gene under the regulatory control of seed specific promoters are described. By the expression of the DNA sequence encoding the medium-chain thioesterase obtained from *Umbullaria californica* (Bay), laurate is now found in the extractible oil of these respective seeds. As the presence of laurate increases, a corresponding decrease in oleic acid (18:1) is observed. Other fatty acid compositional changes with increased laurate include the increase of myristate (14:0) and to a lesser degree, declines in the amounts of linolate (18:2), linolenate (18:3) and palmitate (16:0).

In Arabidopsis, analysis of 100 seed pools led to identification of transformed plants whose seeds contain up to 23.5 mole percent laurate, as compared to the approximately 0% laurate measured in control seeds. As the T2 seeds, that is mature seeds from T1 plants (original transformant) represent a segregating population, even higher levels of laurate would be expected in seeds from second generation plants (T2) grown from the T2 seed.

Analysis of transgenic Brassica seed expressing a bay thioesterase gene (25–30 seed pools) results in identification of transformants whose seeds contain up to 37 mole percent laurate Single and half-seed TAG analyses of these plants demonstrate that the levels of laurate in the segregating seed population are at least as high as 50 mole percent. Half-seed TAG analysis allows for identification of the highest laurate producing T2 seeds, and subsequent germination of the remaining seed portion to produce second generation plants with desirable high laurate seeds.

Correlations between the mole percent medium-chain fatty acid in total fatty acid and gene copy number have been observed. Therefore, although the minimum mole percent medium-chain fatty acid in total fatty acid measured is approximately 50.0 mole percent, it is possible to increase medium-chain fatty acid levels further by the insertion of more genes. Such techniques may involve genetic engineering or plant breeding methods.

Some genetic engineering approaches to increase medium-chain fatty acids would include insertion of additional DNA sequence encoding plant thioesterase structural genes into cells, use of transriptional initiation regions evidencing higher mRNA copy numbers or an improved timing specificity profile which corresponds better to the availability of substrate, for example. For example, analysis of the time course of laurate production, under regulatory control of a napin promoter, in seeds of a Brassica plant demonstrates that the appearance of medium-chain tri-oesterase activity lags behind the onset of storage oil synthesis by approximately 5–7 days. Calculations show that about 20% of the total fatty acids are already synthesized before the medium-chain thioesterase makes significant impact. Thus, substantially higher laurate levels (10–20%) might be obtained if the thioesterase gene is expressed at an earlier stage of embryo development Additionally, means to increase the efficiency of translation may include the use of the complete structural coding sequence of the medium-chain thioesterase gene. Thus, use of the complete 5'-region of the bay thioesterase coding sequence, shown in FIG. 1B, may improve laurate production. Alternatively, if a medium-chain thioesterase has an unusual transit peptide sequence, i.e., one showing similarities with plastid thylakoid targeting, such as found with the bay thioesterase, then use of a more typical plant transit, such as found in safflower (FIG. 4), acyl carrier protein, or ssu may be substituted.

The present invention also provides the opportunuity for production of unsaturated fatty acids in a host cell, including plant cells. Plant medium-chain thioesterases, even from plants which do not have any unsaturated medium-chain fatty acids, may be active against such substrate. Hence, a plant medium-chain fatty acid may be used to provide unsaturated medium-chain fatty acids.

For example, expression of the bay thioesterase in *E. coli* results in the production of laurate (C12:0), myristate. (C14:0) and also unsaturated species of medium-chain fatty acids (C12:1 and C14:1). The production of unsaturated fatty acids in *E. coli* is catalyzed by the action of β-hydroxydecanoyl thioester dehydrase. Sequence of the dehydrase is published (Cronan, et al., *J. Biol. Chem.* (1988)263:4641–4646) and thus can be inserted into a host cell of interest, including a plant cell, for use in conjunction with a medium-chain thioesterase.

When a plant medium-chain thioesterase is expressed in a bacterial cell, particularly in a bacterial cell which is not capable of efficiently degrading fatty acids, an abundance of medium-chain fatty acids can be produced and harvested from the cell. In some instances, medium-chain fatty acid salts form crystals which can be readily separated from the bacterial cells. Bacterial mutants which are deficient in acyl-CoA synthase, such as the E. coli fadD and fadE mutants, may be employed. In studies with fadD mutants, growth of fadD bay thioesterase transformants relative to the vector transformed control was severely retarded at 37° C., and less so at 25°–30° C. Liquid cultures growing at the lower temperatures accumulated a precipitate and colonies formed on petri dishes at 25° C. deposit large quantities of laurate crystals, especially at the surgace. These deposits, as idenfified by FAB-mass spectrometry were identified as laurate. After separation and quantitation by gas chromatography, it is estimated that the laurate crystals deposited by the fadD-bay thioesterase transformants on petri dises represented about 30–100% of the total dry weight of the producing bacteria.

When expression of the medium-chain thioesterase is desired in plant cells, various plants of interest include, but are not limited to, rapeseed (Canola and High Erucic Acid varieties), sunflower, safflower, cotton, Cuphea, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

In any event, the method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. In addition, techniques of microinjection, DNA particle bombardment, electroporation have been developed which allow for the transformation of various monocot and dicot plant species.

The following examples are provided by way of illustration and not by limitation.

EXAMPLES

Example 1
Acyl-ACP Thioesterase cDNA Sequences

Sequence of a full length bay medium-chain thioesterase cDNA clone, pCGN3822, (3A–17), is presented in FIG. 1A.

The translated amino acid sequence of the bay thioesterase beginning at the ATG codon at positions 145–147 is shown in FIG. 1B. This ATG is surrounded by a sequence which matches the rules for plant initiation of translation and is therefore likely to be the initiation codon utilized in vivo. Using the ATG at bp 145 for initiation, a 382 amino acid polypeptide can be translated from the bay thioesterase mRNA. DNA sequence of second class of bay thioesterase genes i provided in FIG. 3.

The N-terminal sequence of the mature bay thioesterase, isolated from the developing seeds, starts at amino acid residue 84 of the derived protein sequence. The N-terminal 83 amino acids therefore represent sequence of a transit peptide. This sequence has features common to plastid transit peptides, which are usually between 40 and 100 amino acids long (Keegstra et al., *Ann. Rev. Plant Physiol. and Plant Mol. Biol.* (1989) 40:471–501). A hydropathy plot of this transit peptide region reveals a hydrophobic domain at each end of the transit sequence. Other transit peptide sequences have been shown to contain similar hydrophobic N-terminal domains. The significance of this N-terminal domain is not known, but certain experiments suggest that lipid-mediated binding may be important for plastid import of some proteins (Friedman and Keegstra, *Plant Physiol.* (1989) 89:993–999). As to the C-terminal domain, comparison of hydropathy plots of known imported chloroplastic stromal protein transit peptides (Reegstra et al, supra) indicates that these transit peptides do not have a hydrophobic domain at the C-terminus. However, preproteins destined to the thylakoid lumen of the chloroplast have an alanine-rich hydrophobic domain at the C-terminal end of their transit peptides (Smeekens et al., *TIBS* (1990) 15:73–76). The existence of such a domain in the transit sequence of the bay thioesterase suggests that it has a double-domain transit peptide targeting this enzyme to the lumen of the thylakoid equivalent or to the intermembrane space. This is unexpected, since the substrate, acyl-ACP, has been detected in the stroma (Ohlrogge et al., *Proc. Nat. Acad. Sci.* (1979) 76: 1194–1198). An alternative explanation for the existence of such a domain in the bay thioesterase preprotein is that it may represent a membrane anchor of the mature protein that is cleaved upon purification, leading to a sequence determination of an artificial N-terminus. The in vivo N-terminus of the mature thioesterase protein would then lie at a location further upstream than indicated by amino acid sequence analysis.

Gene bank searches with the derived amino acid sequence do not reveal significant matches with any entry, including the vertebrate medium-chain acyl-ACP thioesterase II (Naggert et al., *Biochem. J.* (1987) 243:597–601). Also, the bay thioesterase does not contain a sequence resembling the fatty acid synthetase thioesterase active-site motif (Aitken, 1990 in *Identification of Protein Concensus Sequences, Active Site Motifs, Phosphorylation and other Post-translational Modifications* (Ellis Horwood, Chichester, West Sussex, England, pp. 40–147).

For comparison, isolation and sequence of a long-chain acyl-ACP thioesterase is provided. Sequence information from cyanogen bromide peptide sequences of safflower 34 and 40 kD thioesterase proteins is analyzed to obtain a peptide map of the safflower thioesterase. Homology comparisons of these peptides to the amino acid sequence of the bay thioesterase confirm the safflower thioesterase peptide map.

Degenerate oligonucleotide primers are designed from amino acid sequences of safflower thioesterase peptide sequences and used as primers in polymerase chain reactions (PCR) to obtain a fragment of a safflower thioesterase gene.

The thioesterase PCR gene product of the reaction is gel-purified and used as a probe to screen a safflower embryo cDNA library. Six clones are isolated; restriction mapping indicates that they fall into two gene classes. The nucleotide and translated amino acid sequences of a representative from each class, pCGN3264 (2-1) and pCGN3265 (5-2) are presented in FIG. 4A and 4B. Based on N-terminal amino acid sequence information, the amino terminal of the mature safflower thioesterases is assigned to the alanine residue at amino acid 61 of the translated amino acid sequences in FIG. 4A and 4B.

Comparison of the deduced amino acid sequences of the two acyl-ACP thioesterase CDNA clones indicates that the mature proteins are 82% identical while the corresponding DNA sequences share 80% identity. Computer estimates of the isoelectric point of the two proteins differ considerably. The estimated pI for the mature protein encoded by 2-1 is 5.8, while that of the protein encoded by 5-2 is 8.1.

The results of safflower thioesterase purification indicated that there are potentially several forms of the safflower thioesterase. Two distinct molecular mass classes, as well as two separate peak fractions from chromatofocusing were observed. Both molecular mass species are represented in each activity peak. However, protein sequence analysis of each form indicates that these isoforms, are likely products of a single protein. The N-terminal sequence of each species is identical, and no differences in protein sequence of any of the internal CNBr fragments were observed. The different molecular weight species may be the result of a C-terminal peptide being removed either by processing in vivo or by degradation during the extraction and purification, perhaps during the acid precipitation step While peptide sequence evidence indicates that all of the isoforms observed in purification of the safflower thioesterase may be derived from the same protein, two highly homologous but distinct classes of cDNAs were isolated from a safflower embryo cDNA library. Both classes encode an acyl-ACP thioesterase having preferential activity towards C18:1 substrates based on expression in E. coli. However, the peptide sequences data matches only the translated amino acid sequence from the 2-1 encoded protein (with allowance for minor discrepancies due to amino acid sequencing), and no peptides were found that uniquely correspond to the thioesterase encoded by the 5-2 gene. Possibly, the protein encoded by 5-2 is lower in abundance and is not a sufficiently prominent band to be considered for sequencing. Alternatively, the protein encoded by 5-2 may have been a minor component of the digested sample, with the result that the CNBr fragments were not. sufficiently abundant to detect after SDS-PAGE and electroblotting. As examination of the predicted pI's of the two protein products indicates that 5-2 encodes a much more basic protein than does 2-1, the protein corresponding to 5-2 may have been eliminated during the acid precipitation step in purification.

Example 2
Expression of Acyl-ACP Thioesterases In E. coli

Example 2A

Expression of bay thioesterase proteins in E. coli is described.

A truncated Bay (1200 bp) cDNA is expressed as a 30 kD protein in an E. coli host cell and data is provided demonstrating that the cDNA fragment confers upon the transformant an increased C12 acyl-ACP thioesterase activity.

A pET3a vector (Rosenberg, et al., Gene (1987) 56:125–135) is used in an E. coli strain BL21 (PE3) (Studier and Moffat, J. Mol. Biol. (1986) 189:113–130) host for this study. The pET3a vector contains a promoter and 33 bp of the 5' reading frame of bacteriophase T7. T7 polymerase is under the regulatory control of an isopropyl-b-D-thiogalactopyranoside (IPTG)-inducible lac UV5 promoter found in the E. coli BL21 (DE3) strain. Thus, by the addition of IPTG to E. coli BL21 (DE3) transformed with pET3a, the T7 promoter will be activated.

Constructs are prepared containing the truncated cDNA of FIG. 1 fused in reading frame by deletion of the BamHI/EcoRI fragment and replacement of the thioesterase sequence. E. coli are transformed with pET3a constructs containing the thioesterase (pET3a-THI0) and unmodified pET3a as a control. The E. coli are grown at 37° C. in liquid medium and expression is induced by the addition of 1 mM IPTG. After 1 hour induction, cells are harvested by centrifugation, resuspended in assay buffer and lysed by sonication. Cell debris is removed by further centrifugation and the supernant used in activity assays as per Pollard et al., Arch. Biochem & Biphys. (1991) 281:306–312.

TABLE 1

| E. coli Lysate | Assay Substrate | Hydrolysis Activity (mean cpm in ether extract) |
|---|---|---|
| pET3a | 8:0-ACP | 370 |
| " | 10:0-ACP | 787 |
| " | 12:0-ACP | 1028 |
| " | 14:0-ACP | 1271 |
| " | 16:0-ACP | 2848 |
| " | 18:1-ACP | 2877 |
| pET3a-THIO | 8:0-ACP | 349 |
| " | 10:0-ACP | 621 |
| " | 12:0-ACP | 2127 |
| " | 14:0-ACP | 1035 |
| " | 16:0-ACP | 1900 |
| " | 18:1-ACP | 2025 |

The results demonstrate that a lysate of control E. coli cells contains hydrolytic activity towards all the acyl-ACP substrates that were tested, with preference for the long-chain substrates. Comparing the pET3a-THI0 results with the control results it is evident that the pattern of substrate preferences differs. The transformant lysate shows greatly increased activity with 12:0-ACP in relation to the other substrates, as compared with the control lysate. This increased 12:0-ACP activity demonstrates that this cDNA fragment comprises sufficient of the Bay 12:0-ACP thioesterase gene to produce active enzyme in E. coli cells.

In addition, the entire mature bay thioesterase protein is expressed as a lac fusion in E. coli cells. Sequence analysis of the full length bay thioesterase cDNA, pCGN3822, described in Example 1, reveals an XbaI site at base 394. Digestion at this XbaI site cleaves the coding region immediately 5' of the codon representing the leucine at amino acid position 72. This leucine has been identified as a candidate for the amino terminal residue as described in Example 1A.

An approximately 1200 bp fragment of pCGN3822 cDNA is generated by digestion with XbaI, which cuts at the postulated mature protein start site, as described above, and in the vector sequences flanking the 3' end of the cDNA. The XbaI fragment is cloned on XbaI digest of the minus version of a Bluescribe M13(±) (also called pBS±) cloning vector (Stratagene; San Diego, Calif.). The thioesterase gene clone is inserted such that the mature protein is in reading frame with a portion of the lacZ gene of the Bluescribe vector and under control of the lac promoter.

The resulting construct, pCGN3823, and a control Bluescribe construct having the bay thioesterase gene inserted in the opposite orientation are transformed into E. coli. The E. coli cells are grown at 37° C. in liquid medium and expression from the lac promoter is induced by addition of IPTG to a final concentration of 0.1 mM IPTG. Following one hour of induction, cells are harvested, lysed and assayed as described above for the truncated bay thioesterase.

TABLE 2

| Induced E. coli Lysate | Dilution | Assay Substrate | Hydrolysis Activity (mean cpm in ether extract) |
|---|---|---|---|
| pCGN3823 | 1/4000 | 8:0-ACP | 0 |
| " | " | 10:0-ACP | 0 |
| " | " | 12:0-ACP | 1840 |
| " | " | 14:0-ACP | 116 |
| " | " | 16:0-ACP | 20 |

TABLE 2-continued

| Induced E. coli Lysate | Dilution | Assay Substrate | Hydrolysis Activity (mean cpm in ether extract) |
|---|---|---|---|
| " | " | 18:1-ACP | 5 |
| control | 1/4000 | 8:0-ACP | 0 |
| " | " | 10:0-ACP | 0 |
| " | " | 12:0-ACP | 0 |
| " | " | 14:0-ACP | 0 |
| " | " | 16:0-ACP | 13 |
| " | " | 18:1-ACP | 6 |

The results demonstrate that a lysate from E. coli cells expressing the postulated mature bay thioesterase enzyme has significantly greater activity towards a 12:0-ACP substrate than towards other ACP substrates of varying carbon chain length. In addition, this activity is more than two orders of magnitude greater than that in a lysate of E. coli cells expressing the truncated bay thioesterase. Studies are being conducted to determine if expression of the bay thioesterase protein in E. coli cells has an effect on the fatty acid composition of these cells. Initial studies failed to identify a substantial change in the fatty acid composites of the E. coli cells containing the bay thioesterase. However, analysis of larger samples of either pelleted transformed cells or the growth media from which the transformed cells have been pelleted, as described below, indicates a change in the fatty acid profile of the transformed cells. C12 fatty acids are produced in higher amounts in the cells containing the bay thioesterase as compared to untransformed control cells.

Approximately 100 ml of E. coli control cells transformed with the plasmid vector Bluescribe (Stratagene; San Diego, Calif.) and cells transformed with the mature thioesterase construct are grown to an approximate O.D of 0.6 in ECLB (E. coli Luria broth) media, and pelleted by centrifugation. The cells and medium are extracted using an acidic method as follows. The pelleted cells are resuspended in 4 ml of 5% (v/v) $H_2SO_4$ in methanol. The medium is recovered following centrifugation and 10 ml of acetic acid is added. The sample is shaken vigorously with 50 ml ether. The phases are allowed to separate and the lower layer is discarded. The ether layer is allowed to evaporate overnight resulting in 1–2 ml of remaining solution. Four ml of 5% (v/v) $H_2SO_4$ in methanol is added to the remaining medium solution.

The following steps apply for fatty acid analysis of both the media solution and the pelleted cells described above. The cells or medium samples in $H_2SO_4$/methanol are transferred to screw-capped tubes and 2 ml of toluene containing 0.5 mg/ml of a C17 standard is added. The tubes are capped tightly, incubated at 90° C. for 2 hours, after which 4 ml of 0.9% (w/v) NaCl and 2 ml of hexane are added. The samples are vortexed to mix thoroughly and then centrifuged for 5 minutes at 1500 rpm. The upper (hexane) layer of each sample is then centrifuged for 5 minutes at 1000 rpm in a table top centrifuge to separate any extracted fatty acid methyl esters that could be trapped within the layer of E. coli cells.

The samples are analyzed by gas-liquid chromatography (GC) using a temperature program to enhance the separation of components having 10 or fewer carbons. The temperature program used provides for a temperature of 140° C. for 3 minutes, followed by a temperature increase of 5° C./minute until 230° C. is reached, and 230° C. is maintained for 11 minutes. Samples are analyzed on a Hewlett-Packard 5890 (Palo Alto, Calif.) gas chromatograph. Fatty acid content calculations are based on the internal C17 standard.

GC analysis indicates that approximately 70% of the fatty acids in the medium from the transformed cells are C12 fatty acids. This compares to levels of approximately 2% C12 fatty acids in the medium from the control cells. In addition, an approximately 2 fold increase in the C12 content of transformed cells over that of nontransformed cells is observed.

Substrate analysis of the bay thioesterase enzyme purified from developing seeds as described in Pollard, et al, Supra, is also conducted. Results are presented in Table 3 below.

TABLE 3

| Assay Substrate | Hydrolysis Activity (mean cpm in) Ether Extract |
|---|---|
| 8:0-ACP | 0 |
| 10:0-ACP | 0 |
| 12:0-ACP | 1261 |
| 14:0-ACP | 69 |
| 16:0-ACP | 12 |
| 18:1-ACP | 432 |

Comparison of the results of substrate analysis of the thioesterase in the E. coli extracts and as purified from developing bay seeds reveals that the activity profile of the enzyme from the two sources is essentially identical with respect to activity with C8, 10, 12, 14, and 16 ACP substrates. Although the enzyme purified from embryos is slightly more active with C18:1 substrates than is the E. coli-expressed thioesterase, this difference is believed due to activity of a long chain bay thioesterase which is not completely removed from the medium-chain thioesterase protein preparation.

1) Production of Laurate

For further studies, the bay thioesterase expression plasmid (pCGN3823) was established in an E. coli strain, fadD, which lacks the medium-chain specific acyl-CoA synthetase (Overath et al., Eur. J. Biochem (1969) 7:559–574) and is therefore unable to degrade laurate. Growth of fadD bay thioesterase transformants relative to the vector transformed control was studied at 25°, 30° and 37° C. In liquid culture bay thioesterase transformed fadD bacteria multiply, at all three temperatures, at nearly the same rate as the control during the exponential phase of growth. However, at 37° C., fadD cells harboring the bay thioesterase plasmid cannot be recovered from cultures nearing the stationary growth phase. In contrast the plasmids are stably contained at the lower temperatures for several days and these stationary cultures produce a significant amount of a precipitate which is soluble in methanol and ether.

Growth of fadd-bay thioesterase colonies on agar at is severely retarded 37° C., but only slightly so at the lower temperatures. The colonies formed on petri dishes at 25° C. deposit large quantities of crystals, especially at the surface, but also in and at the surface of the cell free agar matrix. These crystal deposits were identified as potassium laurate by (FAB) mass spectrometry. After separation and quantitation by gas chromatography, the laurate crystals are estimated to represent up to 30% of the total dry weight of the producing bacteria.

2) Thiosterase Activity on Unsaturated Fatty Acyl Groups

In addition several new methyl ester peaks are present in the fadD-bay thioesterase, but not in the control E. coli fadD cells. Analyses indicate that two of these peaks represent 12:1 and 14:1 fatty acids. Thus, the bay thioesterase is able to hydrolyze fatty acyl-ACPs from both the saturated and unsaturated fatty acid synthetase pathways that are present in *E. coli*. The saturated pathway is intercepted essentially to 100% in late log phase, and the unsaturated pathway to about 70%. This causes a reduction of saturates in the phospholipids of the cells, substituted mainly by 16:1 and 18:1. The ratio of 12:1 to 14:1 accumulated is approximately 0.9 to 1, whereas the ratio of 12:0 to 14:0 accumulation is approximately 9 to 1. This may indicate that the chain-length specificity of the thioesterase on unsaturated fatty acyl ACPs is different from that on saturated substrates, or alternatively that the 14:1-ACP pool is much larger than the 12:1-ACP pool. In addition, the near complete interception of the saturated pathway appears to result in continuous synthesis of saturated fatty acids during the stationary phase of growth.

The striking difference in laurate accumulation levels between the fadD+ and the fadD transformants is in agreement with studies of bay thioesterase substrates specificity (Pollard, et al., supra). Laurate generated by the introduced bay thioesterase in fadD+ *E. coli* can be esterified to CoA, a much less effective substrate for the bay thioesterase, and subsequently degraded by β-oxidation or recycled for fatty acid synthesis. Therefore, only a small portion can accumulate and escape into the medium. In the fadD strain, laurate is not esterified to CoA and cannot by recycled. The observed slight growth retardation may indicate that the accumulation of laurate to such high levels results in a toxic effect on the *E. coli* host cells.

At 37° C., the synthesis of laurate in the fadD strain is tolerated only during exponential growth. The rapid loss of bay thioesterase plasmid containing cell titer at the end of the log phase may reflect a temperature dependence of laurate toxicity, or a physiological shift to stationary phase metabolism, which causes the introduced bay thioesterase activity to become lethal. The fatty acid composition of *E. coli* changes in aging cultures, and a reduced demand for saturated fatty acids at lower temperatures may lower the negative impact of the bay thioesterase expression at these temperatures. The pathway for unsaturated fatty acids in *E. coli* diverges at the $C_{10}$ stage and is most likely not intercepted by the bay thioesterase.

The accumulation of laurate in the medium is accompanied by deposition of smaller amounts of caprate (10:0). This is in contract with the the thioesterase activity profile where 14:0-ACP hydrolysis is more significant than 10:0-ACP hydrolysis. The high amount of bay thioesterase in these cells may effectively reduce the in vivo pool sizes of acyl-ACP's $\geq$12:0, so that less 14:0 acyl ACP substrate is available. The caprate production by the bay thioesterase in *E. coli* may indicate that this enzyme is responsible for both 10:0 and 12:0 fatty acid deposition in bay seeds.

Example 2B

Expression of safflower thioesterase proteins in *E. coli* is described.

Safflower acyl-ACP thioesterase clones pCGN3264 and pCGN3265 are altered by site-directed mutagenesis to insert SalI and NcoI sites immediately at the start of the mature protein coding region of these clones. The mature coding region plus 3'-untranslated sequences in the cDNA clones are removed as a NcoI/SmaI fragment and inserted into pET8c (Studier et al., 1990) that has been digested with BamHI and treated with Klenow fragment of DNA polymerase to create a blunt end, and then cut with NcoI. The resulting expression constructs, pCGN3270 (2-1) and pCGN3271 (5-2) were designed to express the mature safflower acyl-ACP thioesterase cDNA sequences directly from the T7 promoter. For expression analysis, the constructs are transferred into *E. coli* strain BL21(DE3) containing the T7 RNA polymerase gene under control of the isopropyl β-D-thiogalactopyranoside (IPTG) -inducible lacUV5 promoter (Studier et al., *Methods Enzymol* (1990) 185:60–89).

For thioesterase activity assay, cells containing pCGN3270, pCGN3271, or pET8c as a control are grown at 37° C. to an $OD_{600}$ of ~0.5 in 2YT (16 g tryptone, 10 g yeast extract, 5 g NaCl per liter, pH 7.0) containing 0.4% glucose and 300 μ/ml penicillin. Induction is achieved by the addition of IPTG to 0.4 mM and 1.5 hours further growth. Ten-ml aliquots of culture are harvested by centrifugation and the pelleted cells stored at −70° C. Prior to assay, pellets are resuspended in 500 μl of thioesterase assay buffer and sonicated for three bursts of 20 seconds each. Protein concentrations are determined using the Bio-Rad Protein Assay.

Total protein profiles of *E. coli* containing pCGN3270 and pCGN3271 are analyzed by SDS-PAGE. In each case a new protein band is observed in the IPTG-induced cultures relative to the pET8c control. Although the computer-predicted molecular weight of the 2-1 and 5-2 encoded proteins are very similar, the mobility of these proteins as expressed from pCGN3270 and pCGN3271 is significantly different. The protein encoded by pCGN3270 has a mobility of approximately 40 kD, while the protein encoded by pCGN3271 is approximately 36 kD. The induced proteins were subjected to N-terminal sequencing to confirm their identity. In each case, the protein sequence matched that predicted by the cDNA. In addition, the nucleotide sequence of the 3' region of the 5-2 cDNA insert in pCGN3271 was resequenced to ensure that no premature stop codons had been introduced during the cloning steps.

Total extracts of cells expressing either pET8c (control), pCGN3270, or pCGN3271 are assayed for thioesterase activity using 18:1-ACP. The 18:1-ACP thioesterase activity in cells containing pCGN3270 and pCGN3271 is ~100- and 50-fold higher respectively, than the activity in control cells. To further characterize the safflower acyl-ACP thioesterase, the chain-length specificity of the thioesterase activities expressed from the cDNA clones is tested for a variety of acyl-ACP substrates, and compared to control thioesterase activities of *E. coli* and a crude safflower embryo extract. The pCGN3270 and pCGN3271 cultures contain thioesterase activity characteristic of safflower embryos, i.e. much higher preference for 18:1-ACP vs. 18:0-ACP as compared to control *E. coli*. Between the two safflower thioesterase clones, the activity expressed from pCGN3271 displays a slightly broader specificity for the saturated 18:0-ACP and 16:0-ACP substrates.

Example 3
Constructs & Methods for Plant Transformation

A. Constructs for expression of bay thioesterase in plant cells which utilize phaseolin, napin, CaMV35S and Bce4 promoter regions are prepared as follows.

Phaseolin/thioesterase

A 1.45 kb fragment of pCGN3822 (3A-17) is obtained by digestion with BalI and SalI. The BalI site is located at position 149 of the cDNA insert, and the SalI site is in the polylinker located 3' to the cDNA insert. Thus, this fragment contains the entire thioesterase coding region and the entire cDNA 3' region, including the polyadenylation signal, AAATAA, located at bases 1447–1452, and also contains the restriction digestion sites KpnI, SmaI, XbaI and SalI located directly 3' to the cDNA.

An 850 bp BglII fragment of the B-phaseolin 5' noncoding region was obtained from p8.8Bpro (Hoffman et al. (1987) *EMBO J.* 6:3213–3221) and cloned into pUC9 (Vieira and Messing, supra) at the BamHI site to yield pTV796. The phaseolin fragment in pTV796 is oriented such that SmaI site of pUC9 is located 3' to the phaseolin promoter. An ~850 bp fragment is generated by digestion of pTV796 with HindIII and SmaI and gel-purified.

The phaseolin promoter (HindIII/SmaI) and thioestetase coding region (BalI/SalI) are joined by three way ligation into a Bluescript (Stratagene) cloning vector that has been digested with HindIII and SalI. The resulting plasmid contains the phaseolin promoter/thioesterase construct on a HindIII/SalI fragment that is flanked by various restriction sites, including a 5' BamHI site and a 3' KpnI site. No additional plant 3' noncoding region is provided as the thioesterase fragment contains a polyadenylation signal. The phaseolin promoter/thioesterase fragment may be obtained by digestion with BamHI and KpnI, or alternatively by partial digestion with XbaI, and ligated into an appropriate binary vector, such as pCGN1557 or pCGN1578 (McBride and Summerfelt, (1990) *Plant Mol. Biol.* 14:269–276), for plant transformation. Ligation of the phaseolin promoter/thioesterase fragment, resulting from BamHI and KpnI digestion, into pCGN1578 results in pCGN3821.

35S/thioesterase/mas

An BalI/PstI fragment of the thioesterase CDNA 3A-17 containing approximately 1200 bp, and including the entire coding region, is obtained by partial digestion with restriction enzymes BalI and PstI and gel-purification- of the 1200 bp fragment. The fragment is ligated into a plasmid cloning vector, such as a Bluescript vector (Stratagene Cloning Systems; La Jolla, Calif.), that has been digested with PstI and BamHI, and the BamHI site filled in using the Klenow fragment of DNA Polymerase I. In this procedure, the BamHI site is restored by ligation to the BalI site of the thioesterase cDNA.

The resulting plasmid is partially digested with BamHI and EcoRI to obtain the approximately 1200 bp thioesterase fragment. This fragment is then cloned into an approximately 4.4 kb BamHI/EcoRI DNA fragment which contains approximately 0.94 kb of 5' noncoding sequence from a cauliflower mosaic (CaMV) 35S gene (immediately 5' to the BamHI site), approximately 0.77 kb of 3' noncoding sequence from an Agrobacterium tumefaciens manopine synthase (mas) gene (immediately 3' to the EcoRI site), and a pUCl9 (New England BioLabs, Beverly, Mass.) backbone. The BamHI/EcoRI DNA fragment is obtained by partial digestion of a larger plasmid vector and gel purification of the desired 4.4 kb fragment. The 35S 5' region is from bases 6492 to 7433 of strain CM1841 (Gardner, et al. (1981) *Nucl. Acids Res.* 9:2871–2887), which is from about −640 to about +2 in relation to the transcription start site. The mas 3' noncoding region is from about bases 19,239 to 18,474 of octopine Ti plasmid pTiA6 (numbering corresponds to that of closely related pTil5955 as reported by Barker et al. (*Plant Mol. Biol.* (1983) 2:335–350)).

The resulting 35S/thioesterase/mas plasmid is digested at flanking BglII sites and cloned into a BamHI digested binary vector, such as pCGN1557 or pCGN1578 (McBride and Summerfelt, supra).

Bce4/thioesterase

A 1.45 kb thioesterase cDNA BalI/SalI fragment is prepared as described above. A Bce4 expression cassette, pCGN1870, which provides for preferential expression in early seed development is described in U.S. Pat. No. 5,538,194 which is incorporated herein by reference.

An approximately 1 kb fragment of the Bce4 5' noncoding region whose 3' end is immediately 5' to the Bce4 start codon, is obtained by digestion of pCGN1870 with XbaI and XhoI and gel purification of the resulting 1 kb fragment.

The Bce4 promoter (XbaI/XhoI) and thioesterase coding region (BalI/SalI) are joined by three way ligation into a Bluescribe (Stratagene) cloning vector that has been digested with XbaI and SalI. The resulting plasmid contains the Bce4 promoter/thioesterase construct on a XbaI/SalI fragment that is flanked by various restriction sites, including a 5' BamHI site and a 3' KpnI site. No additional plant 3' noncoding region is provided as the thioesterase fragment contains a polyadenylation signal. The Bce4 promoter/thioesterase fragment may be obtained by digestion with BamHI and partial digestion with KpnI (or Asp718 which has the same recognition sequence), or alternatively by partial digestion with XbaI, and ligated into an appropriate binary vector, such as pCGN1557 or pCGN1578 (McBride and Summerfelt, supra), for plant transformation. Ligation of the Bce4 promoter/thioesterase fragment, resulting from BamHI and KpnI digestion, into pCGN1578 results in pCGN3820.

Napin/thioesterase/napin

The napin expression cassette, pCGN1808, is described in copending U.S. patent application Ser. No. 07/550,804, abandoned which is incorporated herein by reference. pCGN1808 is modified to contain flanking restriction sites to allow movement of only the expression sequences and not the antibiotic resistance marker to binary vectors such as pCGN1557 (McBride and Summerfelt, supra), Synthetic oligonucleotides containing KpnI, NotI and HindIII restriction sites are annealed and ligated at the unique HindIII site of pCGN1808, such that only one HindIII site is recovered. The resulting plasmid, pCGN3200 contains unique HindIII, NotI and KpnI restriction sites at the 3'-end of the napin 3'-regulatory sequences as confirmed by sequence analysis.

The majority of the napin expression cassette is subcloned from pCGN3200 by digestion with HindIII and SacI and ligation to HindIII and SacI digested pIC19R (Marsh, et al. (1984) *Gene* 32:481–485) to make pCGN3212. The extreme 5'-sequences of the napin promoter region are reconstructed by PCR using pCGN3200 as a template and two primers flanking the SacI site and the junction of the napin 5'-promoter and the pUC backbone of pCGN3200 from the pCGN1808 construct. The forward primer contains ClaI, HindIII, NotI, and KpnI restriction sites as well as nucleotides 408–423 of the napin 5'-sequence (from the EcoRV site) and the reverse primer contains the complement to napin sequences 718–739 which include the unique SacI site in the 5'-promoter. The PCR was performed using in a Perkin Elmer/Cetus thermocycler according to manufacturer's specifications. The PCR fragment is subcloned as a blunt-ended fragment into pUC8 (Vieira and Messing (1982) *Gene* 19:259–268) digested with HincII to give pCGN3217. Sequenced of pCGN3217 across the napin insert verifies that no improper nucleotides were introduced by PCR. The napin 5-sequences in pCGN3217 are ligated to the remainder of the napin expression cassette by digestion with ClaI and SacI and ligation to pCGN3212 digested with ClaI and SacI. The resulting expression cassette pCGN3221, is digested with HindIII and the napin expression sequences are gel purified away and ligated to pIC20H (Marsh, supra) digested with HindIII. The final expression cassette is pCGN3223, which contains in an ampicillin resistant background, essentially identical 1.725 napin 5' and 1.265 3' regulatory sequences as found in pCGN1808. The regulatory regions are flanked with HindIII, NotI and KpnI restriction sites and unique SalI, BglII, PstI, and XhoI cloning sites are located between the 5' and 3' noncoding regions.

The 1200 bp BalI/PstI thioesterase cDNA fragment described above is cloned into the napin expression cassette, pCGN3223, which has been digested with SalI, and the SalI site filled in using the Klenow fragment of DNA Polymerase I, followed by digestion with PstI. The SalI site is reconstituted in this ligation.

The napin/thioesterase/napin plasmid generated by these manipulations is digested with BamHI and partially digested with KpnI to generate an approximately 3.3 kb fragment. This fragment contains ~1.7 kb of napin 5' noncoding sequence, the ~1200 bp BalI/PstI thioesterase cDNA fragment and ~0.33 kb of 3' napin noncoding region, the rest of the 1.265 kb of the napin 3' having been deleted due to the BamHI site in this region. The ~3.3 kb fragment is ligated to KpnI/BamHI digested pCGN1557 or pCGN1578 (McBride and Summerfelt, supra) for plant transformation.

Insertion of the ~3.3 kb fragment into pCGN1578 results in pCGN3816.

Napin/thioesterase

An approximately 1.5 kb fragment of the full length thioesterase cDNA is obtained by partial digestion of pCGN3822 with BamHI and KpnI and subsequent gel-purification of the resulting 1.5 kb fragment. The BamHI site is at nucleotide 74 of the cDNA sequence and the KpnI site is in the vector polylinker located 3' to the cDNA insert. Thus, this fragment contains the entire thioesterase coding region, including the ATG codon at positions 145–147, and the entire CDNA 3' region, which contains a polyadenylation signal as described above.

An approximately 1.7 kb fragment of the napin 5' noncoding region is obtained by digestion of pCGN3223 (described above) with HindIII and BglII and subsequent gel-purification of the 1.7 kb fragment.

The napin promoter (HindIII/BglII) and the thioesterase coding region (BamHI/KpnI) are joined by a three fragment ligation into a binary vector, such as pCGN1557 or pCGN1578 (McBride and Summerfelt, supra) that is digested with HindIII and KpnI. In this reaction, the complementary overhanging ends of the BamHI and BglII sites allows fusion of the 3' end of the napin fragment to the 5' end of the thioesterase fragment. The resulting plasmid for plant transformation from ligation into pCGN1578, pCGN3824, contains the thioesterase cDNA positioned for expression under the regulatory control of the napin promoter. No additional plant 3' noncoding region is provided as the thioesterase fragment contains a polyadenylation signal.

Napin/thioesterase/napin

A construct for expression of thioesterase under the transcriptional and translational control of napin promoter and 3' transcriptional termination regions is made as follows. pCGN3822 (described above) is engineered using PCR techniques to insert a BamXI site immediately 5' to the thymine nucleotide at position 140 (5 bases upstream of the ATG start codon) of the bay thioesterase sequence shown in FIG. 1A (SEQ ID NO:41), resulting in pCGN3826. An approximately 1225 bp fragment containing the entire thioesterase encoding region is obtained from pCGN3826 as a BamHI to PstI fragment and ligated into BglII/PstI digested pCGN3223, the napin expression cassette described above, resulting in pCGN3827. A vector for plant transformation, pCGN3828, is constructed by partially digesting pCGN3827 with KpnI and BamHI, and cloning the approximately 3.2 kb fragment containing the napin 5'/thioesterase/napin 3' construct into KpnI/BamHI digested pCGN1578 (McBride and Summerfelt, supra).

A construct, pCGN3837, is prepared which is similar to pCGN3828, but has the bay transit peptide coding region replaced with a sequence encoding the safflower thioesterase transit peptide and 6 amino acids of the mature safflower thioesterase from clone 2-1. The safflower fragment for this construct may be prepared using PCR techniques to provide convenient restriction digestion sites. Another construct having napin 5' and 3' regulatory regions is prepared which replaces the region encoding the bay thioesterase transit peptide and the first 11 amino acids of the mature bay thioesterase protein with a sequence encoding the safflower thioesterase transit peptide and the first 31 amino acids of the mature safflower thioesterase protein.

An appropriate Agrobactezium strain is transformed with the binary constructs and used to generate transformed laurate producing plants. Seeds are collected and analyzed as described above to determine efficiency of plastid transport and oil composition.

B. A variety of methods have been developed to insert a DNA sequence of interest into the genome of a plant host to obtain the transcription or transcription and translation of the sequence to effect phenotypic changes.

Brassica Transformation

Seeds of *Brassica napus* cv. Westar are soaked in 95% ethanol for 2 min. surface sterilized in a 1.0% solution of sodium hypochlorite containing a drop of Tween 20 for 45 min., and rinsed three times in sterile, distilled water. Seeds are then plated in Magenta boxes with 1/10th concentration of Murashige minimal organics medium (Gibco; Grand Island, N.Y.) supplemented with pyriodoxine (50 $\mu$g/1), nicotinic acid (50 $\mu$g/1), glycine (200 $\mu$g/1), and 0.6% Phytagar (Gibco) pH 5.8. Seeds are germinated in a Percival chamber at 22° C. in a 16 h photoperiod with cool fluorescent and red light of intensity approximately 65$\mu$ Einsteins per square meter per second ($\mu$Em$^{-2}$S$^{-1}$).

Hypocotyls are excised from 5–7 day old seedlings, cut into pieces approximately 4 mm in length, and plated on feeder plates (Horsch et al., *Science* (1985) 227:1229–1231). Feeder plates are prepared one day before use by plating 1.0 ml of a tobacco suspension culture onto a petri plate (100×25 mm) containing about 30 ml MS salt base (Carolina Biological, Burlington, N.C.) 100 mg/l inositol, 1.3 mg/l thiamine-HCl, 200 mg KH$_2$PO$_4$ with 3% sucrose, 2,4-D (1.0 mg/l), 0.6% w/v Phytagar, and pH adjusted to 5.8 prior to autoclaving (MS 0/1/0 medium) . A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2 mg/l), Kinetin (0.1 mg/l). In experiments where feeder cells are not used hypocotyl explants are cut and placed onto a filter paper disc on top of MS0/1/0 medium. All hypocotyl explants are preincubated on feeder plates for 24 h. at 22° C. in continuous light of intensity 30 $\mu$Em$^{-2}$S$^{-1}$ to 65 $\mu$EM$^{-2}$S$^{-1}$.

Single colonies of *A. tumefaciens* strain EHA 101 containing a binary plasmid are transferred to 5 ml MG/L broth and grown overnight at 30° C. Hypocotyl explants are immersed in 7–12 ml MG/L broth with bacteria diluted to 1×10$^8$ bacteria/ml and after 10–25 min. are placed onto feeder plates. Per liter MG/L broth contains 5 g mannitol, 1 g L-Glutamic acid or 1.15 g sodium glutamate, 0.25 g kH$_2$PO$_4$, 0.10 g NaCl, 0.10 g MGSO$_4$·7H$_2$O, 1 mg biotin, 5 g tryptone, and 2.5 g yeast extract, and the broth is adjusted to pH 7.0. After 48 hours of co-incubation with Agrobacterium, the hypocotyl explants are transferred to B5 0/1/0 callus induction medium which contains filter sterilized carbenicillin (500 mg/l, added after autoclaving) and kanamycin sulfate (Boehringer Mannheim; Indianapolis, Ind.) at concentrations of 25 mg/l.

After 3–7 days in culture at 65 $\mu EM^{-2}S^{-1}$ continuous light, callus tissue is visible on the cut surface and the hypocotyl explants are transferred to shoot induction medium, B5BZ (B5 salts and vitamins supplemented with 3 mg/l benzylaminopurine, 1 mg/l zeatin, 1% sucrose, 0.6% Phytagar and pH adjusted to 5.8). This medium also contains carbenicillin (500 mg/l) and kanamycin sulfate (25 mg/l) Hypocotyl explants are subcultured onto fresh shoot induction medium every two weeks.

Shoots regenerate from the hypocotyl calli after one to three months. Green shoots at least 1 cm tall are excised from the calli and placed on medium containing B5 salts and vitamins, 1% sucrose, carbenicillin (300 mg/l), kanamycin sulfate (50 mg/l) and 0.6% w/v Phytagar). After 2–4 weeks shoots which remain green are cut at the base and transferred to Magenta boxes containing root induction medium (B5 salts and vitamins, 1% sucrose, 2 mg/l indolebutyric acid, 50 mg/l kanamycin sulfate and 0.6% Phytagar). Green rooted shoots are tested for thioesterase activity.

Arabidposis Transformation

Transgenic *Arabidopsis thaliana* plants may be obtained by Agrobacterium-mediated transformation as described by Valverkens et al., (*Proc. Nat. Acad. Sci.* (1988) 85:5536–5540). Construacts are transfromed in Agrobacterium cells, such as of strain EHA101 (Hood et al., *J. Bacteriol* (1986) 168:1291–1301), by the method of Holsters et al. (*Mol. Gen. Genet.* (1978) 163:181–187).

Peanut Transformation

DNA sequences of interest may be introduced as expression cassettes, comprising at least a promoter region, a gene of interest, and a termination region, into a plant genome via particle bombardment as described in European Patent Application 332 855 and in U.S. Pat. No. 5,665,346, filed Jul. 27, 1988.

Briefly, tungsten or gold particles of a size ranging from 0.5 $\mu$M–3 $\mu$M are coated with DNA of an expression cassette. This DNA may be in the form of an aqueous mixture or a dry DNA/particle precipitate.

Tissue used as the target for bombardment may be from cotyledonary explants, shoot meristems, immature leaflets, or anthers.

The bombardment of the tissue with the DNA-coated particles is carried out using a Biolistics™ particle gun (Dupont; Wilmington, Del.). The particles are placed in the barrel at variable distances ranging from 1 cm–14 cm from the barrel mouth. The tissue to be bombarded is placed beneath the stopping plate; testing is performed on the tissue at distances up to 20 cm. At the moment of discharge, the tissue is protected by a nylon net or a combination of nylon nets with mesh ranging from 10 $\mu$M to 300 $\mu$M.

Following bombardment, plants may be regenerated following the method of Atreya, et al., (*Plant Science Letters* (1984) 34:379–383). Briefly, embryo axis tissue or cotyledon segments are placed on MS medium (Murashige and Skoog, *Physio. Plant.* (1962) 15:473) (MS plus 2.0 mg/l 6-benzyladenine incubated in the dark for 1 week at 25°±2° C. and are subsequently transferred to continuous cool white fluorescent light (6.8 W/m$^2$). On the 10th day of culture, the plantlets are transferred to pots containing sterile soil, are kept in the shade for 3–5 days are and finally moved to greenhouse.

The putative transgenic shoots are rooted. Integration of exogenous DNA into the plant genome may be confirmed by various methods know to those skilled in the art.

C. Transgenic plants transformed with thioesterase constructs are analyzed for thioesterase activity and fatty acid and triglyceride compositions.

Arabidopsis seeds from selfed transgenic A. thaliana plants transformed with pCGN3816 and pCGN3821 are analyzed for 12:0 and 14:0 acyl-ACP thioesterase activities. Developing seeds are extracted with thioesterase assay buffer (Example 1) and the soluble fraction assayed. Transgenic seeds show significant increase of 12:0 thioesterase activity over the controls. Also, the 14:0-ACP hydrolysis increases, but at a smaller scale, in agreement with enzyme specificity data from transformed *E. coli*.

Figure 7:
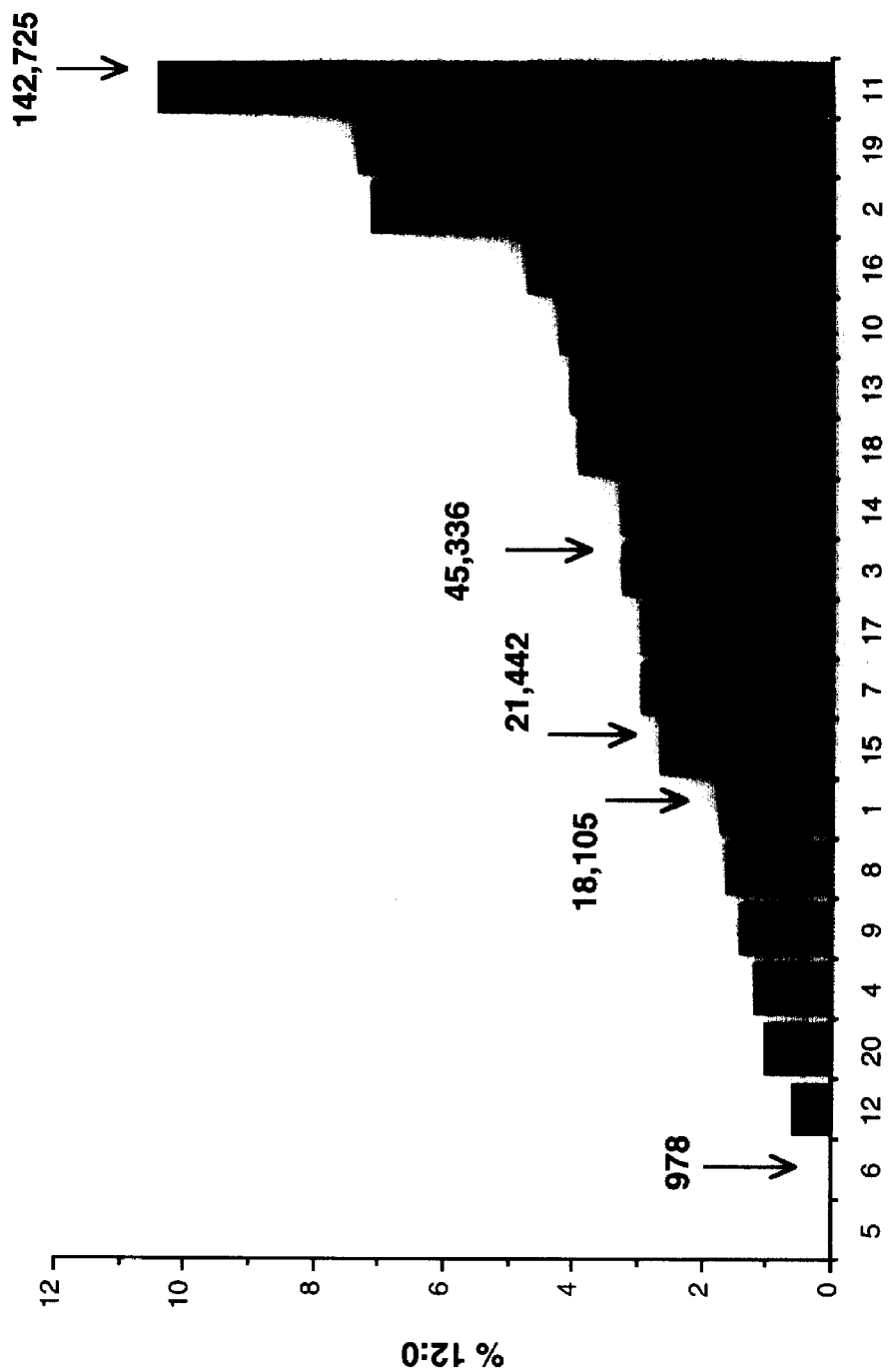
FIG. 7. Lauroyl levels and C12:0-ACP thioesterase activity for seeds from transgenic *B. napus* is presented.

Total fatty acid analysis of mature *A. thaliana* seeds reveals up to 5% laurate in plants transformed with the above described constructs, as compared to 0% laurate as measured in control plant seeds. FIG. 7 demonstrates that the percent laurate directly correlates with lauroyl thioesterase activity in transgenic seeds. Also, the myristate content in transgenic seeds increases from 0.1% (control) up to 0.7% in the highest expressers and also correlates with the myristoyl thioesterase activity. Triglyceride analysis by thin-layer chromatography shows that the laurate detected by total fatty acid analysis is present in the neutral lipids fraction, evidence that the laurate is incorporated (esterified) into triglycerides.

Mature seeds from *A. thaliana* plants transformed with pCGN3828 are analyzed for total fatty acids essentially as described by Browse et al. (*Anal. Biochem.* (1986) 152:141–145) as described in detail in Example 16. These studies reveal at least one plant, 3828-13, whose seeds contain up to approximately 17% by weight (23.5 mole percent) laurate. Mature seeds from this transformed plant are subjected to a pancreatic lipase digestion protocol (Brockerhoff (1975) *Meth. Enzymol.* 35:315–325) to distinguish acyl compositions of the sn-2 and sn-1+3 (combined) positions. Preliminary results from these analyses are as follows:

| sn – 1 + 2 + 3 | (methanolysis) | 17.8% C12 |
| sn – 2 | (lipase digestion) | 2.9% C12 |
| sn – 1 + 3 | (calculated from above) | 25.3% C12 |
| sn – 1 + 3 | (lipase digestion) | 21.9% C12. |

These preliminary results suggest that medium-chain fatty acids are efficiently incorporated into the sn-1 and/or sn-3 positions of the triglyceride molecule.

A total of 26 pCGN3828-transformed Arabidopsis plants were tested for 12:0-ACP thioesterase activity, with seven testing positive. The presence of "transformants" that are negative for laurate expression is not surprising as the Arabidopsis transformation method does not include selection at the rooting stage. Thus, the laurate negative plants would be expected to include non-transformed "escapes," as well as transformed plants which are not expressing the bay thioesterase gene. Analysis of mature seeds (100-seed pools) from these seven positive plants shows that the positive plants contain significant amounts of 12:0, which is absent from controls. The amounts of 12:0 ranged from 2.1 to 23.5 mole percent and approximately correlate with the thioesterase activity. The total fatty acid contents of the seeds are within the range typically seen in Arabidopsis, suggesting that the 12:0 deposition does not adversely affect oil yield. No obvious effects on seed development or morphology are observed. Lipid class analysis (TLC) demonstrates that the triglyceride fraction contains the same proportion of laurate as the total extractable fatty acids, i.e. at these levels the 12:0 is readily incorporated into triglyceride.

A small amount of 14:0 also accumulates in transgenic Arabidopsis seeds. The ratio of 12:0 to 14:0 fatty acids in the seeds (6–8) is similar to the ratio of in vitro thioesterase activities on 12:0-ACP and 14:0-ACP. The near-constant ratio between the 12:0 and 14:0 products presumably reflects the specificity of the bay thioesterase towards 12:0-ACP and 14:0-ACP, and suggests that the enzyme function in vivo in the transgenic seeds by direct action on similarly sized pools of 12:0-ACP and 14:0-ACP. The bay thioesterase appears to have no significant action on 10:0-ACP in vitro and only a minor trace of 10:0 is detected in the transgenic seeds.

Figure 9:
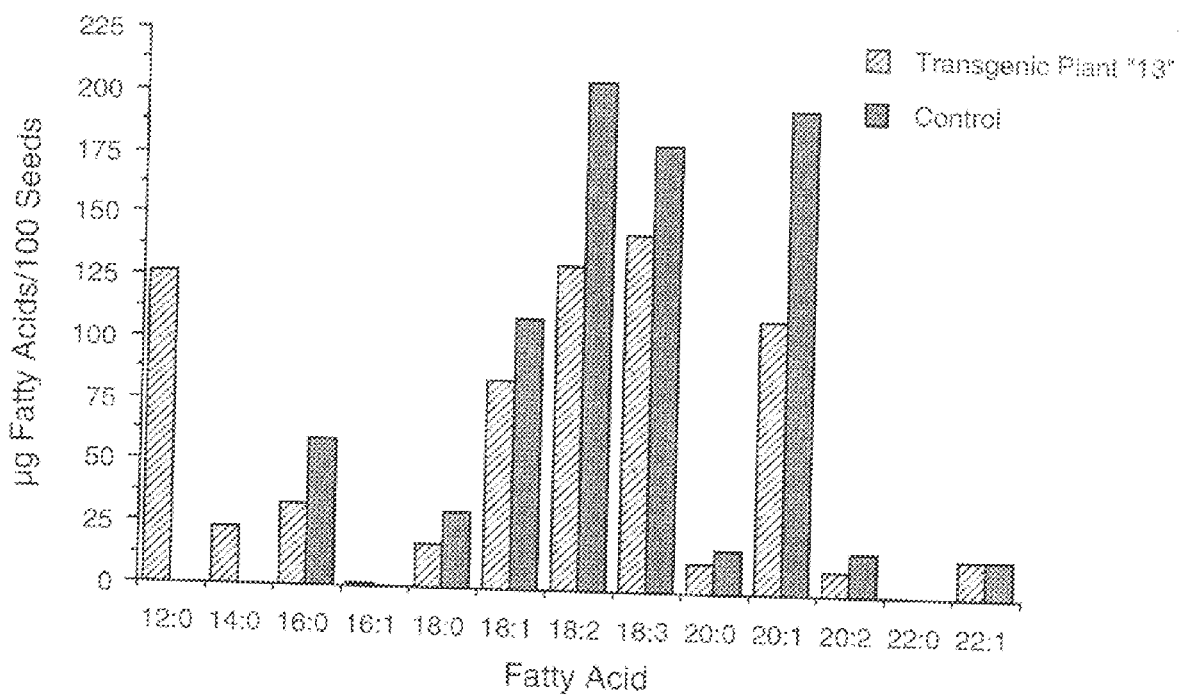
FIG. 9. Fatty acid composition of 100 seeds from transgenic Arabidopsis plant 3828-13 is compared to the fatty acid composition of seeds from a control Arabidopsis plant.

Additional studies were conducted to determine if the medium-chains were synthesized at the expense of all, or only some, of the "native" Arabidopsis fatty acids. The average fatty acid composition of 100 mature seeds from a control Arabidopsis plant were compared with that from transgenic plant 3828-13. The results of these studies are shown in FIG. 9. The differences in 12:0 and 14:0 contents of the two plants are clear, but differences in the contents of other fatty acids as a result of medium-chain production are more difficult to identify. The total fatty acid contents varied considerably between Arabidopsis plants, making comparisons of absolute fatty acid levels very difficult. Expression of the data in percentage terms (total fatty acids=100) to eliminate these differences created further difficulties with interpretation.

Figure 10A:
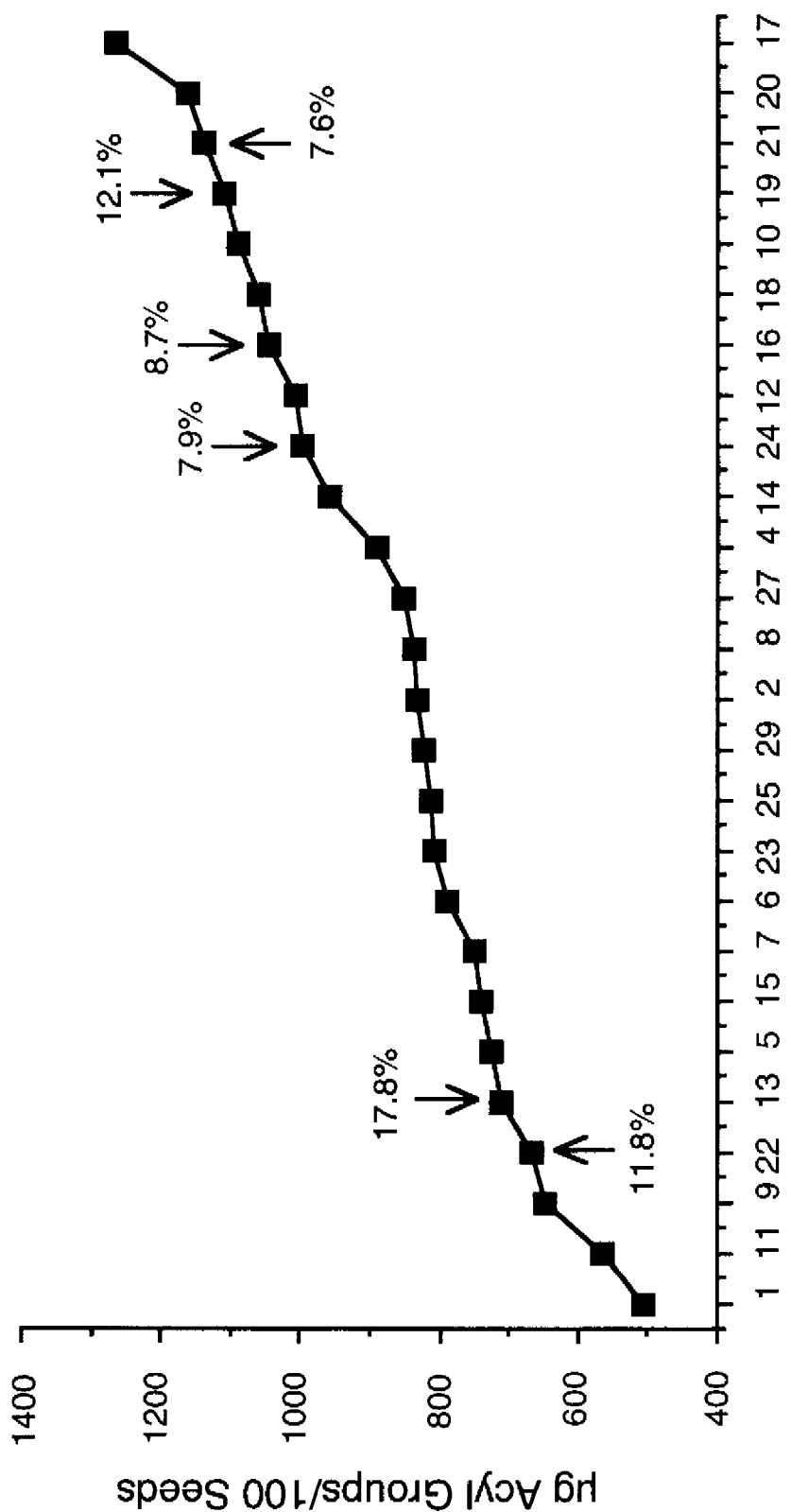
FIGS. 10A–10B. Fatty acid content of 26 transgenic Arabidopsis plants is provided in FIG. 10A in order of increasing fatty acid content. The transformants producing detectable levels of laurate are indicated.
Figure 10B:
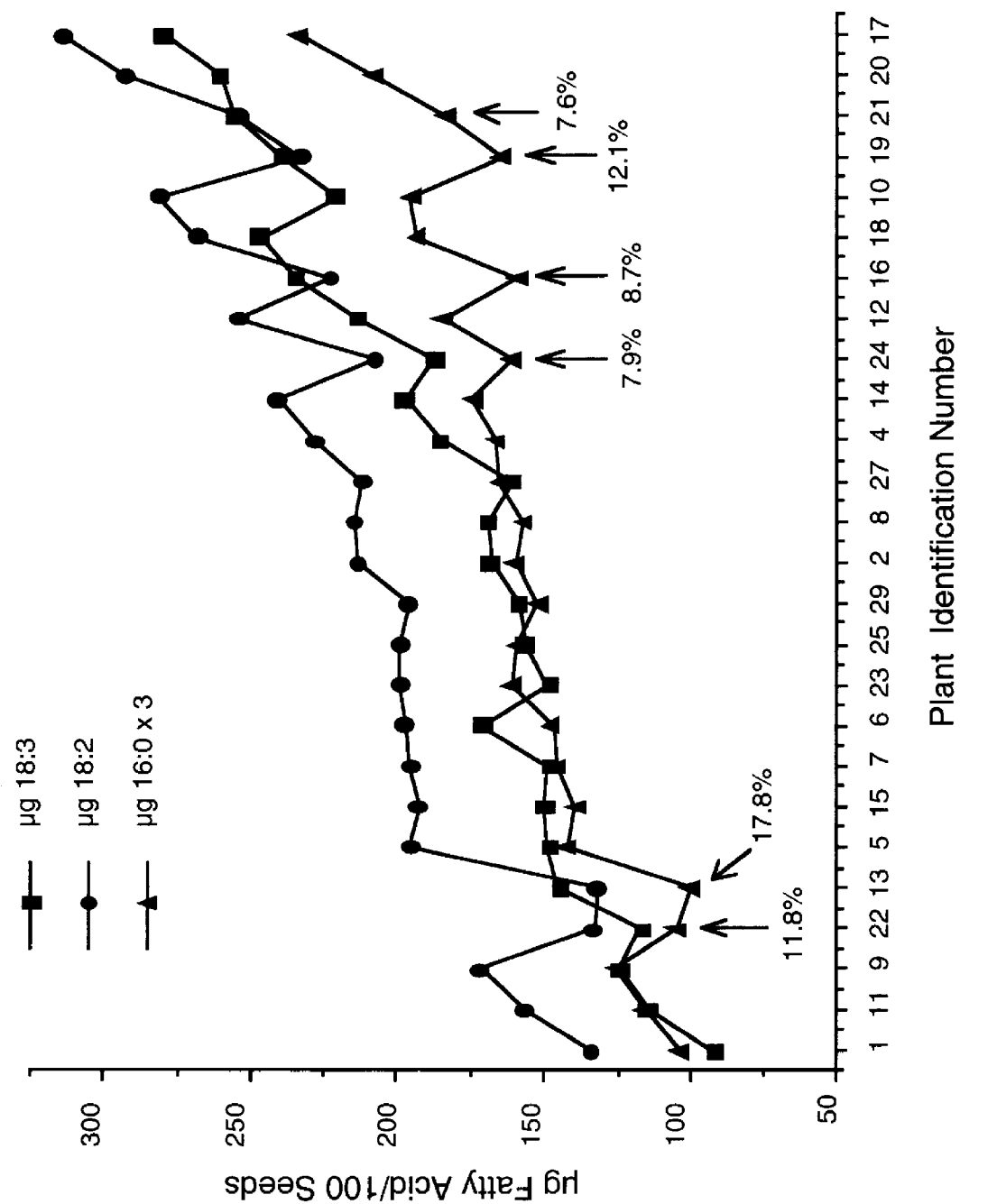

Thus, a way to distinguish unique fatty acid compositions from typical inter-plant variation was devised as follows. The total fatty acid contents of mature (T2) seeds from the 26 T1 Arabidopsis plants were arranged in increasing order, and produced a smooth spread of values as shown in FIG. 10A. The six highest laurate producers are indicated by arrows, along with the corresponding weight % 12:0 data. There appears to be no relationship between the levels of 12:0 production and total fatty acid content. In FIG. 10B the data are shown ordered in the same way, but for three fatty acids individually. The data for 18:2 and 16:0 also formed a smooth line, except for the positive events in which laurate accumulated. In those instances the contents of 18:2 and 16:0 were noticeably below the overall trend, showing that 12:0 was produced in those seeds at the expense of 18:2 and 16:0. This was also true for 18:1, 20:1, and 20:2. The only major fatty acid constituent to be relatively unaffected by 12:0 production was 18:3, as shown in FIG. 10B, although low-18:3 controls can be found, for example in plant 10.

Seeds from *Brassica napus* plants transformed with pCGN3816 are also analyzed for total fatty acids as described above. Analysis of single segregating seeds from T2 transformed plants reveals levels of C12:0 ranging from zero to 14.5%, as compared to zero percent in seeds from untransformed control plants. C12:0 levels correlate to C12:0-ACP thioesterase activities in corresponding immature seeds, as demonstrated in FIG. 7. In addition, C14:0 is also detected in these seeds at levels correlating with those of the C12:0, although C14:0 levels are lower.

Figure 11A:
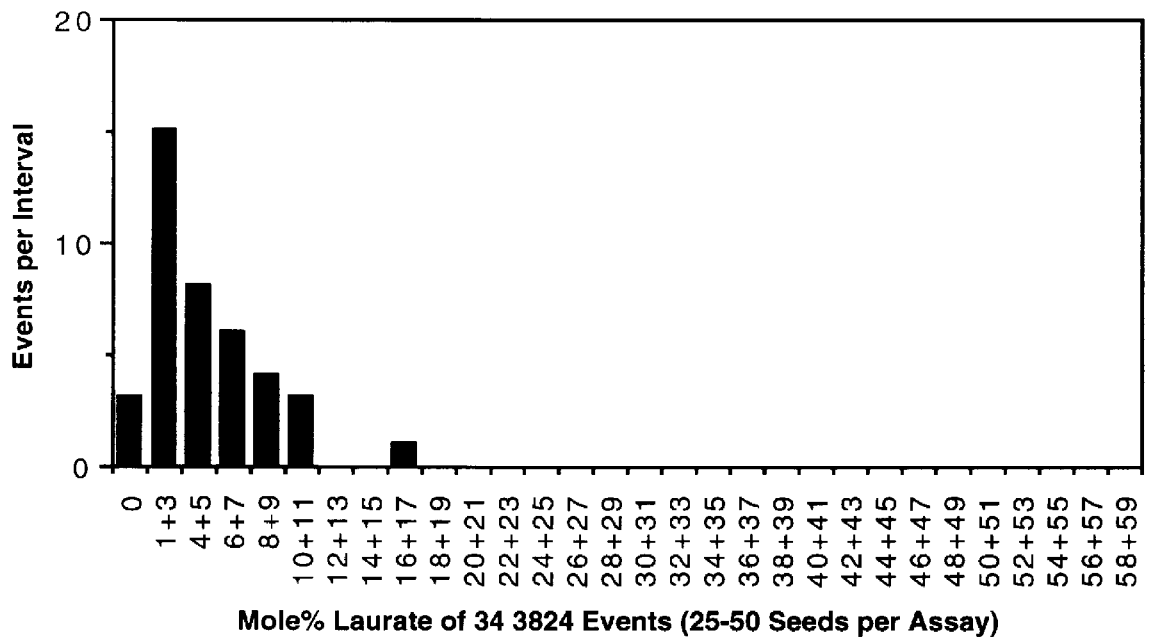
FIG. 11A–11B. Mole percent laurate contents in developing seeds of transgenic *Brassica napus* are presented as the number of transgenic events yielding the indicated laurate levels. Results from pCGN3824 transformants are shown in FIG. 11A and results from pCGN3828 transformants are shown in FIG. 11B.
Figure 11B:
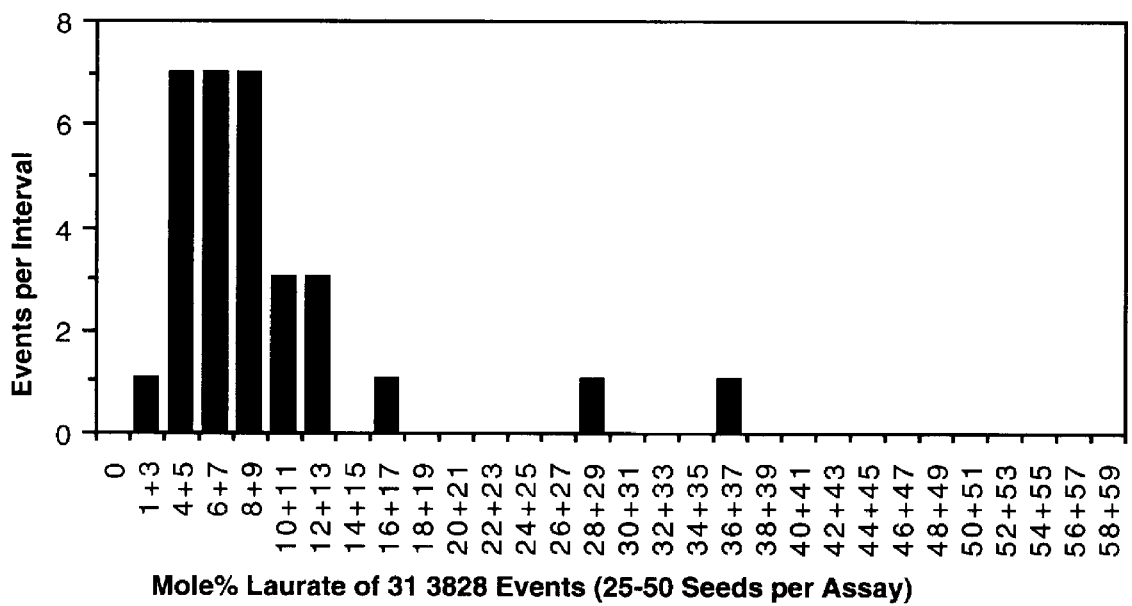

Transformed *Brassica napus* plants containing the pCGN3824 (napin/thioesterase) and pCGN3828 (napin/thioesterase/napin) constructs were analyzed to determine seed fatty acid composition. Pooled seeds from 34 plants transformed with pCGN3824 and 31 plants transformed with pCGN3828 were analyzed (25–50 seeds per assay) to determine the ranges of laurate levels in the seeds. The results of these analyses, presented as the number of transgenic events having a given percentage of laurate, are presented in FIG. 11A and 11B. The pCGN3824-transformants had laurate contents ranging from 0–11 mole percent, with the exception of a single plant whose seeds contained 17 mole percent laurate. The pCGN3828 construct plants had laurate contents ranging from 1–17 mole percent, with two representatives outside this range having 37 mole percent laurate (plant 3828-23) and 27 mole percent laurate (plant 3828–35). In addition, the seed oils of these plants also have smaller amounts of C14:0 fatty acids, corresponding to approximately 16% of the laurate levels. Trace levels of C10:0 are also observed, typically at 1% of the laurate level. Additional pCGN3828-transformants are also being analyzed to identify plants having even higher laurate contents.

Half-seed analysis is also used to determine laurate levels in mature seeds from transformed plants. For half-seed analysis, seeds are placed on a moistened (2–3 ml water) filter paper disc in a Petri dish which is sealed and left in the dark for 20 to 48 hours at room temperature or 30° C. Germinated seeds have 2–5 mm radicles protruding from the seed coats. Fine forceps are used to remove each seedling from its coat and tease away the outer cotyledon. Dissected cotyledons are placed in 4 ml vials and dried for 2–12 hours in a 110° C. oven prior to fatty acid analysis. The dissected seedlings are planted directly into potting soil in 12-pack containers, misted, covered with transparent plastic lids, placed in a growth chamber at 22° C. in 150–200 microEinsteins m$^{-2}$s$^{-1}$ light intensity with a 16 h/8 h photoperiod, and allowed to grow to produce T2 (second generation transformants) plants. Alternatively, half-seed analysis may be conducted using a chipped portion of a mature seed. Seeds are held under a dissecting scope and a chip of approximately 30% of the seed is removed, avoiding the embryonic axis. The seed chip is used for fatty acid analysis by GC, and the remaining seed portion is germinated in water for 5–7 days in a microtiter dish, transferred to soil, and grown to produce T2 seed.

The laurate content of 144 assayed pCGN3828–35 half seeds ranged from 4 to 42 mole percent. The laurate content of 214 assayed pCGN3828–23 half seeds ranged from 12 to 50 mole percent. No seeds that were analyzed from either the pCGN3828-23 or pCGN3828-35 plants had zero laurate, indicating that these transformants have three or more thioesterase inserts in their genome. In addition, analyses using approximately 60 half-seeds of the pCGN3828-transformants having 10–20 mole % laurate in their seeds indicates that these plants have 1–2 insertions of the bay thioesterase gene.

To examine the fate of the laurate in transgenic *Brassica napus* seeds, the fatty acid compositions of different lipid classes extracted from mature transgenic seeds of two transgenic plants, pCGN3828-23 and pCGN3828-7, were examined. TLC analysis of the phospholipids indicates that nearly 100% of the laurate is in the TAG fraction. Analyses of the acyl compositions of the sn-2 and sn-1+3 positions of the TAG are conducted using the pancreatic lipase protocol (Brockerhoff (1975), supra). Ideally with this protocol, the lipase cleaves fatty acids from the sn-1 and sn-3 positions, and not from the sn-2 position. Thus, the fatty acids in the resulting mono-glyceride are presumed to be those in the sn-2 position. Initial studies of TAG in the laurate transformants with this method indicate that C12:0 fatty acids are not incorporated into the sn-2 position. However, it is noted that those previously attempting to study TAG having shorter-chain fatty acids by this method (Entressangles et al. (1964) *Biochem. Biophys. Acta* 84:140–148), reported that shorter-chain fatty acids located at the sn-2 position were quickly hydrolyzed during such a digestion, which the authors reported to be the result of a spontaneous migration of internal shorter-chain fatty acids towards outer positions in diglycerides and monoglycerides.

Additional analyses of transformed plants containing the pCGN3828 construct are conducted to further characterize the expression of bay thioesterase in these plants. The extractable C12:0 thioesterase activity in developing seeds of pCGN3828-23 transformants is measured and is determined to be considerably higher than the endogenous 18:1 thioesterase activity. In view of the high bay thioesterase activity in transgenic plants, additional factors are being investigated for optimization of laurate production.

The presence of the processed (34 kD) bay thioesterase in transformed 3828-23 plants is investigated by Western analysis of a developmental time course of seeds from this plant. Experiments are conducted using polyclonal antibody to bay thioesterase and a biotin labeled second antibody. These studies indicate that a major seed storage protein in Brassica migrates with the same mobility as the bay thioesterase, causing non-specific background staining. However, a band of approximately 42 kD apparent molecular weight which reacts with the bay Ab is detected in transformed laurate producing plants. This apparent molecular weight is consistent with that of the unprocessed bay thioesterase.

Alternate Western detection methods are under study to reduce the non-specific background staining. For example, a second antibody method where the second antibody is coupled to alkaline phosphatase, results in reduced background staining. Accumulation of bay thioesterase is detectable at low levels at day 24 after pollination, with strong signals observed in seeds from days 30–40 after pollination. Initial results suggest that most of the signal is the 42 kD unprocessed preprotein, with only 10–20% of the thioesterase antigen migrating at 34 kD. These studies suggest that the unusual transit peptide of the bay thioesterase may result in non-optimal plastid targeting in Brassica.

RNA analysis of the above developmental time course seed samples shows that the napin-driven bay thioesterase mRNA accumulates with the same kinetics as the total endogenous napin message, with peak transcription in the 27–50 day range. Thus, the bay thioesterase activity lags behind the onset of storage oil synthesis by about 5–7 days, and earlier expression of the bay thioesterase may make a significant impact on total laurate levels in mature seeds. Northern analysis of ACP and stearoyl-ACP desaturase transcripts in the above seed sample indicates that the native transcripts of these genes accumulate 3–5 days earlier than the bay thioesterase transcript produced by the napin promoter. These data suggest that the ACP and stearoyl-ACP desaturase gene promoters may be useful for earlier expression of the bay thioesterase gene. Cloning of a cDNA for a Brassica rapa stearoyl-ACP desaturase and a promoter region for B. rapa ACP have been described (Knutzon et al. (1992) Proc. Nat. Acad. Sci. 89:2624–2628; Scherer et al. (1992) Plant Mol. Biol. 18:591–594).

Transformed Arabidopsis plants which contain a construct (pCGN3836) having the 1.2 kb bay thioesterase gene fragment positioned for expression from an approximately 1.5 kb region of the B. rapa ACP promoter, and approximately 0.3 kb of a napin 3' regulatory region, have been obtained. Initial analysis of the seeds from the pCGN3836-transformed plants for laurate content, indicates that laurate does not accumulate to detectable levels in these seeds. However, it is possible that when expression timing and targeting of bay thioesterase are optimized in transgenic Brassica seeds a small amount of thioesterase will make a great deal of laurate, as appears to occur in bay, and a lower level of expression of bay thioesterase may be sufficient.

Example 4

Transgenic Plants

Plants transformed with thioesterase constructs are analyzed for thioesterase activity and fatty acid and triglyceride compositions.

A. Arabidopsis

Arabidopsis seeds from selfed transgenic A. thaliana plants transformed with pCGN3816 and pCGN3821 are analyzed for 12:0 and 14:0 acyl-ACP thioesterase activities. Developing seeds are extracted with thioesterase assay buffer (Pollard, et al, supra) and the soluble fraction assayed. Transgenic seeds show significant increase of 12:0 thioesterase activity over the controls. Also, the 14:0-ACP hydrolysis increases, but at a smaller scale, in agreement with enzyme specificity data from transformed E. coli.

Total fatty acid analysis of mature A. thaliana seeds reveals up to 5% laurate in plants transformed with the above described constructs, as compared to 0% laurate as measured in control plant seeds. FIG. 2 demonstrates that the percent laurate directly correlates with lauroyl thioesterase activity in transgenic seeds. Also, the myristate content in transgenic seeds increases from 0.1% (control) up to 0.7% in the highest expressers and also correlates with the myristoyl thioesterase activity. Triglyceride analysis by thin-layer chromatography (TLC) shows that the laurate detected by total fatty acid analysis is present in the neutral lipids fraction, evidence that the laurate is incorporated (esterified) into triglycerides.

Mature seeds from A. thaliana plants transformed with pCGN3828 are analyzed for total fatty acids by GC essentially as described by Browse et al. (Anal. Biochem. (1986) 152:141–145) as described in detail in Example 2. These studies reveal at least one plant, 3828–13, whose seeds contain up to approximately 17% by weight (23.5 mole percent) laurate. Mature seeds from this transformed plant are subjected to a pancreatic lipase digestion protocol (Brockerhoff (1975) Meth. Enzymol. 35:315–325) to distinguish acyl compositions of the sn-2 and sn-1+3 (combined) positions. Preliminary results from these analyses are as follows:

| sn − 1 + 2 + 3 | (methanolysis) | 17.8% C12 |
| sn − 2 | (lipase digestion) | 2.9% C12 |
| sn − 1 + 3 | (calculated from above) | 25.3% C12 |
| sn − 1 + 3 | (lipase digestion) | 21.9% C12. |

These preliminary results suggest that medium-chain fatty acids are efficiently incorporated into the sn-1 and/or sn-3 positions of the triglyceride molecule. (Further discussion of this technique is provided below.)

In a different experiment, out of 26 pCGN3828-transformed Arabidopsis plants tested for 12:0-ACP thioesterase activity, seven tested positive. The presence of "transformants" that are negative for laurate expression is not surprising as the Arabidopsis transformation method does not include selection at the rooting stage. Thus, the laurate negative plants would be expected to include non-transformed "escapes," as well as transformed plants which are not expressing the bay thioesterase gene. Analysis of mature seeds (100-seed pools) from these seven positive plants shows that the positive plants contain significant amounts of 12:0, which is absent from controls. The amounts of 12:0 ranged from 2.1 to 23.5 mole percent and approximately correlate with the thioesterase activity.

The total fatty acid contents of the seeds are within the range typically seen in Arabidopsis, suggesting that the 12:0 deposition does not adversely affect oil yield. No obvious effects on seed development or morphology are observed. Lipid class analysis (TLC) demonstrates that the triglyceride fraction contains the same proportion of laurate as the total extractable fatty acids, i.e. at these levels the 12:0 is readily incorporated into triglyceride.

A small amount of 14:0 also accumulates in transgenic Arabidopsis seeds. The ratio of 12:0 to 14:0 fatty acids in the seeds is similar to the ratio of in vitro thioesterase activities on 12:0-ACP and 14:0-ACP. The near-constant ratio between the 12:0 and 14:0 products presumably reflects the specificity of the bay thioesterase towards 12:0-ACP and 14:0-ACP, and suggests that the enzyme function in vivo in the transgenic seeds by direct action on similarly sized pools of 12:0-ACP and 14:0-ACP. The bay thioesterase appears to have no significant action on 10:0-ACP in vitro and only a minor trace of 10:0 is detected in the transgenic seeds.

Additional studies were conducted to determine if the medium-chains were synthesized at the expense of all, or only some, of the "native" Arabidopsis fatty acids. The average fatty acid composition of 100 mature seeds from a control Arabidopsis plant were compared with that from transgenic plant 3828-13. The results of these studies are shown in FIG. 9. The differences in 12:0 and 14:0 contents of the two plants are clear, but differences in the contents of other fatty acids as a result of medium-chain production are more difficult to identify. The total fatty acid contents varied considerably between Arabidopsis plants, making comparisons of absolute fatty acid levels very difficult. Expression of the data in percentage terms (total fatty acids=100) to eliminate these differences created further difficulties with interpretation.

Thus, a way to distinguish unique fatty acid compositions from typical inter-plant variation was devised as follows. The total fatty acid contents of mature (T2) seeds from the 26 T1 Arabidopsis plants were arranged in increasing order, and produced a smooth spread of values as shown in FIG. 10A. The six highest laurate producers are indicated by arrows, along with the corresponding weight percent 12:0 data. There appears to be no relationship between the levels of 12:0 production and total fatty acid content. In FIG. 10B the data are shown ordered in the same way, but for three fatty acids individually. The data for 18:2 and 16:0 also formed a smooth line, except for the positive events in which laurate accumulated. In those a instances the contents of 18:2 and 16:0 were noticeably below the overall trend, showing that 12:0 was produced in those seeds at the expense of 18:2 and 16:0. This was also true for 18:1, 20:1, and 20:2. The only major fatty acid constituent to be relatively unaffected by 12:0 production was 18:3, as shown in Figure 10B, although low-18:3 controls can be found, for example in plant 10.

B. Brassica

Seeds from Brassica napus plants transformed with pCGN3816 are also analyzed for total fatty acids by GC as described above. Analysis of single segregating seeds (T2 seeds) from transformed plants (T1 plants) reveals levels of C12:0 ranging from zero to 14.5%, as compared to zero percent in seeds from untransformed control plants. C12:0 levels correlate to C12:0-ACP thioesterase activities in corresponding immature seeds, as demonstrated in FIG. 7. In addition, C14:0 is also detected in these seeds at levels correlating with those of the C12:0, although C14:0 levels are lower.

Minor modifications may be made to the GC temperature program used for analysis of laurate-containing TAG. An additional useful temperature cycle is as follows: 160° C. for 3 minutes, followed by a 5 degrees per minute temperature ramp to final temperature of 240° C., which is held for 6 minutes; this results in a total run time of 26 minutes.

Transformed Brassica napus plants containing the pCGN3824 (napin/thioesterase) and pCGN3828 (napin/thioesterase/napin) constructs were analyzed to determine seed fatty acid composition. Pooled seeds from 34 plants transformed with pCGN3824 and 31 plants transformed with pCGN3828 were analyzed (25–50 seeds per assay) to determine the ranges of laurate levels in the seeds. The results of these analyses, presented as the number of transgenic events having a given percentage of laurate, are presented in FIG. 11. The pCGN3824-transformants had laurate contents ranging from 0–11 mole percent, with the exception of a single plant whose seeds contained 17 mole percent laurate. The pCGN3828 construct plants had laurate contents ranging from 1–17 mole percent, with two representatives outside this range having 37 mole percent laurate (plant 3828-23) and 27 mole percent laurate (plant 3828-35). It is noted that in addition to containing laurate, the seed oils of these plants also have smaller amounts of C14:0 fatty acids, corresponding to approximately 16% of the laurate levels.

Half-seed analysis is also used to determine laurate levels in mature seeds from transformed plants. For half-seed analysis, seeds are placed on a moistened (2–3 ml water) filter paper disc in a Petri dish which is sealed and left in the dark for 20 to 48 hours at room temperature or 30° C. Germinated seeds have 2–5 mm radicles protruding from the seed coats. Fine forceps are used to remove each seedling from its coat and tease away the outer cotyledon. Dissected cotyledons are placed in 4 ml vials and dried for 2–12 hours in a 110° C. oven prior to fatty acid analysis. The dissected seedlings are planted directly into potting soil in 12-pack containers, misted, covered with transparent plastic lids, placed in a growth chamber at 22° C. in 150–200 microEinsteins $m^{-2}s^{-1}$ light intensity with a 16 h/8 h photoperiod, and allowed to grow to produce T2 (second generation transformants) plants. Alternatively, half-seed analysis may be conducted using a chipped portion of a mature seed. Seeds are held under a dissecting scope and a chip of approximately 30% of the seed is removed, avoiding the embryonic axis. The seed chip is used for fatty acid analysis by gas chromatography, and the remaining seed portion is germinated in water for 5–7 days in a microtiter dish, transferred to soil, and grown to produce T2 plants. A chart providing fatty acid composition as mole percent of total fatty acids of 15 representative pCGN3828-23 half-seeds is shown in Table 4A. Similar data from single seeds collected from non-transformed regenerated control plants are shown in Table 4B. Data are from GC half-seed analysis as described above.

TABLE 4A

|  | 12:0 | 14:0 | 16:0 | 18:0 | 18:1 | 18:2 | 18:3 |
|---|---|---|---|---|---|---|---|
| 3828-23# 112 | 12.00 | 1.43 | 4.51 | 1.42 | 47.70 | 16.73 | 13.90 |
| 3828-23# 45 | 20.50 | 2.04 | 4.45 | 0.88 | 47.29 | 11.39 | 10.89 |
| 3828-23# 121 | 21.43 | 2.34 | 4.19 | 1.11 | 45.16 | 13.34 | 9.75 |
| 3828-23# 122 | 24.11 | 2.67 | 4.18 | 1.08 | 40.75 | 12.43 | 12.29 |
| 3828-23# 133 | 28.54 | 3.33 | 4.01 | 0.86 | 42.71 | 10.21 | 7.62 |
| 3828-23# 197 | 32.14 | 3.21 | 3.71 | 1.05 | 38.15 | 8.85 | 10.29 |
| 3828-23# 209 | 35.89 | 3.77 | 3.39 | 1.07 | 35.20 | 9.78 | 8.70 |
| 3828-23# 3 | 40.74 | 3.63 | 3.19 | 0.98 | 32.81 | 10.19 | 6.43 |
| 3828-23# 205 | 43.56 | 4.22 | 3.13 | 0.79 | 27.30 | 9.16 | 9.71 |
| 3828-23# 199 | 45.87 | 4.43 | 3.21 | 0.99 | 25.32 | 7.98 | 9.95 |
| 3828-23# 132 | 47.52 | 4.20 | 2.87 | 1.70 | 23.91 | 9.88 | 7.54 |
| 3828-23# 56 | 47.93 | 4.18 | 3.03 | 0.62 | 24.62 | 12.43 | 5.51 |
| 3828-23# 65 | 49.54 | 4.71 | 3.18 | 0.80 | 19.60 | 11.49 | 8.65 |
| 3828-23# 12 | 50.69 | 4.35 | 2.94 | 0.70 | 20.03 | 12.28 | 7.81 |

TABLE 4B

|     | 12:0 | 14:0 | 16:0 | 18:0 | 18:1 | 18:2 | 18:3 |
|-----|------|------|------|------|------|------|------|
| R-1 | 0.0  | 0.0  | 5.9  | 1.8  | 56.9 | 19.5 | 12.7 |
| R-1 | 0.0  | 0.0  | 6.0  | 1.5  | 57.8 | 21.7 | 10.3 |
| R-2 | 0.0  | 0.0  | 5.9  | 1.9  | 56.2 | 20.0 | 12.7 |
| R-2 | 0.0  | 0.0  | 5.4  | 1.1  | 59.8 | 18.8 | 12.3 |
| R-3 | 0.0  | 0.0  | 4.8  | 1.3  | 60.2 | 20.4 | 11.1 |
| R-3 | 0.0  | 0.0  | 4.6  | 1.2  | 58.2 | 22.1 | 11.7 |
| R-4 | 0.0  | 0.0  | 5.4  | 1.3  | 57.7 | 20.5 | 12.6 |

The laurate content of 144 assayed pCGN3828-35 half seeds (T2 seed obtained from a T2 plant) ranged from 4 to 42 mole percent. The laurate content of 214 assayed pCGN3828-23 half seeds ranged from 12 to 50 mole percent. No seeds that were analyzed from either the pCGN3828-23 or pCGN3828-35 plants had zero laurate which statistically indicates that these transformants have three or more thioesterase inserts in their genome. Analysis of seed produced from the T2 generation will further confirm this result. In addition, analyses using approximately 60 half-seeds of the pCGN3828-transformants having 10–20 mole percent laurate in their seeds indicates that these plants have 1–2 insertions of the bay thioesterase gene.

To examine the fate of the laurate in transgenic *Brassica napus* seeds, the fatty acid compositions of different lipid classes extracted from mature transgenic seeds of two transgenic plants, pCGN3828-23 and pCGN3828-7, were examined. TLC analysis of the phospholipids indicates that nearly 100% of the laurate is in the triacylglyceride (TAG) fraction. Analyses of the acyl compositions of the sn-2 and sn-1+3 positions of the TAG are conducted using the pancreatic lipase protocol (Brockerhoff (1975), supra). Ideally with this protocol, the lipase cleaves fatty acids from the sn-1 and sn-3 positions, and not from the sn-2 position. Thus, the fatty acids in the resulting mono-glyceride are presumed to be those in the sn-2 position. Initial studies of TAG in the laurate transformants with this method indicate that C12:0 fatty acids are not incorporated into the sn-2 position. However, it is noted that those previously attempting to study TAG having shorter-chain fatty acids by this method (Entressangles et al. (1964) *Biochim. Biophys. Acta* 84:140–148), reported that shorter-chain fatty acids located at the sn-2 position were quickly hydrolyzed during such a digestion, which the authors reported to be the result of a spontaneous migration of internal shorter-chain fatty acids towards outer positions in diglycerides and monoglycerides.

Additional analyses of transformed plants containing the pCGN3828 construct are conducted to further characterize the expression of bay thioesterase in these plants. The extractable C12:0 thioesterase activity in developing seeds of pCGN3828-23 transformants is measured and is determined to be considerably higher than the endogenous 18:1 thioesterase activity. In view of the high bay thioesterase activity in transgenic plants, additional factors are being investigated for optimization of laurate production.

The presence of the processed (34 kD) bay thioesterase in transformed 3828-23 plants is investigated by Western analysis of a developmental time course of seeds from this plant. Experiments are conducted using polyclonal antibody to bay thioesterase and a biotin labeled second antibody. These studies indicate that a major seed storage protein in Brassica migrates with the same mobility as the bay thioesterase, causing non-specific background staining. However, a band of approximately 42 kD apparent molecular weight which reacts with the bay antibody is detected in transformed laurate producing plants. This apparent molecular weight is consistent with that of the unprocessed bay thioesterase.

Alternate Western detection methods are under study to reduce the non-specific background staining. For example, a second antibody method where the second antibody is coupled to alkaline phosphatase, results in reduced background staining. Accumulation of bay thioesterase is detectable at low levels at day 24 after pollination, with strong signals observed in seeds from days 30–40 after pollination. Initial results suggest that most of the signal is the 42 kD unprocessed preprotein, with only 10–20% of the thioesterase antigen migrating at 34 kD. These studies suggest that the unusual transit peptide of the bay thioesterase may result in non-optimal plastid targeting in Brassica.

RNA analysis of the above developmental time course seed samples shows that the napin-driven bay thioesterase mRNA accumulates with the same kinetics as the total endogenous napin message, with peak transcription in the 27–50 day range. Thus, the bay thioesterase activity lags behind the onset of storage oil synthesis by about 5–7 days, and earlier expression of the bay thioesterase may make a significant impact on total laurate levels in mature seeds. Northern analysis of ACP and stearoyl-ACP desaturase transcripts in the above seed samples indicates that the native transcripts of these genes accumulate 3–5 days earlier than the bay thioesterase transcript produced by the napin promoter. These data suggest that the ACP and stearoyl-ACP desaturase gene promoters may be useful for earlier expression of the bay thioesterase gene. Cloning of a cDNA for a Brassica rapa stearoyl-ACP desaturase and a promoter region for B. rapa ACP have been described (Knutzon et al. (1992) *Proc. Nat. Acad. Sci.* 89:2624–2628; Scherer et al. (1992) *Plant Mol. Biol.* 18:591–594).

Transformed Arabidopsis plants which contain a construct (pCGN3836) having the 1.2 kb bay thioesterase gene fragment positioned for expression from an approximately 1.5 kb region of the B. rapa ACP promoter, and approximately 0.3 kb of a napin 3' regulatory region, have been obtained. Initial analysis of the seeds from the pCGN3836-transformed plants for laurate content, indicates that laurate does not accumulate to detectable levels in these seeds. However, it is possible that when expression timing and targeting of bay thioesterase are optimized in transgenic Brassica seeds a small amount of thioesterase will make a great deal of laurate, as appears to occur in bay, and a lower level of expression of bay thioesterase may be sufficient.

Example 5

Obtaining Other Plant Thioesterases

A. Additional Sources of Plant Thioesterases

In addition to the Bay and safflower thioesterases identified in previous Examples, other plants are sources of desirable thioesterases which have varying specificities with respect to fatty acyl chain length and/or degree of saturation. Such additional plant thioesterases may be identified by analyzing the triacylglyceride composition of various plant oils and the presence of a specific thioesterase confirmed by assays using the appropriate acyl-ACP substrate.

Other plants which may have desirable thioesterase enzymes include elm (Ulmaceae) and camphor (*Cinnamomum camphora*). A significant percentage of 10:0 fatty acids are detected in elm seeds, and both 10:0 and 12:0 fatty acids are prominent in seeds from camphor. Results of biochemical assays to test for thioesterase activity in developing embryos from camphor and elm are presented below in Table 5.

TABLE 5

| | Activity (mean cpm in ether extract) | |
|---|---|---|
| Substrate | elm | camphor |
| 8:0-ACP | 84 | 0 |
| 10:0-ACP | 2199 | 465 |
| 12:0-ACP | 383 | 1529 |
| 14:0-ACP | 1774 | 645 |
| 16:0-ACP | 3460 | 940 |
| 18:1-ACP | 3931 | 3649 |

With elm, a peak of thioesterase activity is seen with the C10:0-ACP substrate, in addition to significant activity with longer-chain substrates. This evidence suggests that a thioesterase with specific activity towards C10:0-ACP substrate is present in elm embryos. Significant activity towards C12:0-ACP substrate is detected in camphor extracts. In addition, camphor extracts demonstrate greater activity towards C10:0-ACP substrates than do similar extracts from bay embryos. This evidence suggests that a medium-chain acyl-ACP thioesterase having specificity towards C10:0-ACP and C12:0-ACP substrates is present in camphor embryos.

In a like fashion, longer chain fatty acyl thioesterase (C16 or C18) can also be obtained. For example, a significant percentage (45%) of 16:0 fatty acids is found in the tallow layer of the seeds of the Chinese tallow tree (*Sapium sebiferum*) and in the seed oil of cotton (*Gossypium hirsutum*) (Gunstone, Harwood and Padley eds. *The Lipid Handbook*, (1986) Chapman and Hall, Ltd., The University Press, Cambridge).

Approximately 250 mg each of developing Chinese tallow tissue, cotton embryos (var. Stoneville 506, day 21 post-anthesis) or *Brassica napus* embryos (cv. Delta, day 28 post-anthesis) are ground to a fine powder in a mortar and pestle under liquid nitrogen and extracted by homogenization in 1 ml 50 mM sodium phosphate pH 7.5, 2 M dithiothreitol, 2 mM sodium ascorbate, 20% v/v glycerol, 1% w/v PVP-10 and 5 mM diethyldithiocarbamate in a glass homogenizer with a motor driven pestle. The homogenate is centrifuged in a microcentrifuge tube for 15 min and aliquots of the supernatant fraction are assayed for thioesterase activity as follows.

Twenty-five μl of a 1/20 dilution of the supernatant in assay buffer (7 mM potassium phosphate, pH 8.0, 20% v/v glycerol, 0.02% w/v Triton X-100, 1 mM dithiothreitol) is added to 70 μl of assay buffer in a glass screw top vial. Fifty pmoles of [$^{14}$C]-radiolabeled acyl-substrate are added to start the reaction. The substrates are myristoyl-ACP (14:0-ACP), palmitoyl-ACP (16:0-ACP), stearoyl-ACP (18:0-ACP) or oleoyl-ACP (18:1-ACP) synthesized as described for lauroyl-AC? in Pollard, et al., supra. Vials are incubated 30 min, 30 C. The reactions are stopped with acetic acid and free fatty acids are extracted with ether by adding 0.5 ml 10% (v/v) cold (4°) acetic acid and placing the reaction mixture on ice for a few minutes. The fatty acid product of the hydrolytic enzyme action is extracted away from the unhydrolyzed substrate by adding 2 ml diethyl ether and mixing vigorously. The ether is transferred to 5 ml scintillation fluid for scintillation counting. Additional ether extracts may be performed to recover remaining traces of product for more accurate quantitation of the activity if desired.

Substrate specificity analysis results for cotton, Chinese tallow and Brassica are shown in Table 6.

TABLE 6

| | Activity (mean cpm in ether extract) | | |
|---|---|---|---|
| Substrate | tallow | cotton | Brassica |
| 14:0-ACP | 254 | 944 | 180 |
| 16:0-ACP | 1038 | 1542 | 506 |
| 18:0-ACP | 733 | 860 | 500 |
| 18:1-ACP | 2586 | 3667 | 4389 |

A peak of activity is seen with the 16:0-ACP substrate as well as the 18:1-ACP substrate in both cotton and Chinese tallow whereas the Brassica seed profile only shows significant activity with the 18:1-ACP. It appears that an acyl-ACP thioesterase with specificity for 16:0 fatty-acyl ACP accounts for the triacylglyceride composition of Chinese tallow and cotton.

Two peaks of thioesterase activity are observed in extracts of cotton embryos chromatographed on heparin-agarose. This chromatography has been shown to separate two different thioesterases, a 12:0-ACP thioesterase and an 18:1 thioesterase from Bay extracts (Pollard, et al., *Arch. Biochem. Biophys.* (1991) 284:306–312). Of the two peaks of activity observed from the chromatography of cotton extracts the first has higher 18:1 activity than 16:0 activity and the second peak has higher 16:0 activity than 18:1 activity. The data suggests the presence of two enzymes with distinct specificities in cotton.

In addition, kernel oil of mango (*Mangiffera indica*) contains 24–49% stearic acid and 6–18% palmitic acid in triacydglycerols and the oil has been suggested for use as a cocoa butter substitute (Osman, S. M., "Mango Fat", in *New Sources of Fats and Oils*, (1981) eds. Pryde, E. H., Princen, L. H., and Mukherjee, K. D., American Oil Chemists Society) . Similarly to the examples described above, a thioesterase with 18:0-ACP specificity can be demonstrated by biochemical assay of embryo extracts.

B. Isolating Thioesterase genes

Having obtained sequence (amino acid and DNA) for Bay and safflower thioesterase, similar genes from other plant sources such as those identified above can be readily isolated. In this example, two methods are described to isolate other thioesterase genes: (1) by DNA hybridization techniques using sequences or peptide sequence information from the Bay and safflower thioesterase gene and (2) by immunological cross-reactivity using antibodies to the Bay protein as a probe.

In either of these techniques, cDNA or genomic libraries from the desired plants are required. Many methods of constructing CDNA or genomic libraries are provided for example in Chapter 8 and 9 of Maniatis, et al. (*Molecular Cloning: A Laboratory Manual*, Second Edition (1989) Cold Spring Harbor Laboratory, Cold Spring Harbor, N.Y.).

Probes for use in DNA hybridizations to isolate other plant thioesterase genes can be obtained from the Bay and safflower thioesterase gene sequences provided or alternatively by PCR using oligonucleotides from thioesterase peptide sequences.

In this example, a PCR-generated DNA fragment is used as a probe. Northern analysis of embryo RNA from the desired plant species is conducted to determine appropriate hybridization conditions. RNA is electrophoresed in a formaldehyde/agarose gel and transferred to a nylon membrane filter as described by Fourney, et al. (Focus (1988) Bethesda Research Laboratories/Life Technologies, Inc., 10:5–7. A $^{32}$P-labeled probe (Random Primed DNA labeling kit, Boehringer Mannheim, Indianapolis, Ind.) is added to a hybridization solution containing 50% formamide, 6×SSC (or 6× SSPE), 5× Denhardt's reagent, 0.5% SDS, and 100 µg/ml denatured salmon sperm DNA fragments.

The hybridization solution containing the labeled probe is incubated with the Northern filter at approximately 40° C. for 18 hours or longer to allow hybridization of the probe to homologous (50–80%) sequences. The filter is then washed at low stringency (room temperature to 42° C. in about 1× SSC). Hybridization and washing temperatures may be adjusted based on the estimated melting temperature of the probe as discussed in Beltz, et al. (*Methods in Enzymology* (1983) 100:266–285). In further testing the temperature is raised either in the hybridization or washing steps, and/or salt content is lowered to improve detection of the specific hybridizing sequence.

A useful probe and appropriate hybridization and washing conditions having been identified as described above, cDNA libraries are screened using the $^{32}$P-labeled fragment and optimized conditions.

For example, an ~600 bp BamHI/XhoI fragment of thioesterase clone pCGN3263 is radio-labeled and used as a heterologous probe to isolate a thioesterase clone from a *B. campestris* embryo cDNA library. DNA sequence of a Brassica thioesterase cDNA clone is presented in FIG. 6. Along with the translated amino acid sequence from the proposed ATG start codon. Additional Brassica clones which show some variations in DNA sequence are also being analyzed.

In addition to direct hybridization techniques using heterologous thioesterase genes as probes, PCR techniques may also be used to create probes for hybridization or to generate thioesterase encoding sequences from mRNA or DNA from the desired plant source. For example, a camphor (*Cinnamomum camphora*) thioesterase clone may be isolated using nucleic acid and amino acid sequence information from the bay and safflower thioesterase clones. Homology of the bay thioesterase cDNA clone to RNA isolated from developing camphor embryos is observed by Northern analysis as follows. Total RNA is isolated from 1 g of developing camphor embryos by adaptation of the SDS/phenol extraction method described in *Current Protocols in Molecular Biology*, pages 4.3.1–4.3.4 (Ausubel et al., eds. (1987); John Wiley & Sons). The grinding buffer for this extraction contains 100 mM LiCl, 100 mM Tris pH9, 10 mM EDTA, 1% SDS and 0.5% β-mercaptoethanol. For extraction from 1 g of embryos, 10 ml of grinding buffer plus 3 ml of phenol equilibrated to pH8 are added to powdered embryos. The homogenization step may be conducted in a mortar instead of with a polytron, as described in the published method, and the heating step which follows homogenization in that method is omitted. Centrifugation, phenol/chloroform extractions of the sample and LiCl precipitation of RNA are as described.

Total RNA (10–20 µg) is electrophoresed in a formaldehyde/agarose gel and transferred to a nylon membrane filter as described by Fourney et al. (supra). A probe for hybridization of the Northern filter is prepared from a SalI digest of pCGN3822, the full length bay thioesterase cDNA by PCR using oligonucleotides to the safflower thioesterase cDNA sequence to generate an approximately 1300 bp fragment. The forward primer contains nucleotides 212 to 228 of the safflower thioesterase cDNA sequence (SEQ ID NO:4) and the reverse primer is the complement to nucleotides 1510–1526 of the cDNA sequence. The fragment is gel purified using a Prep-A-Gene DNA purification kit (BioRad; Richmond, Calif.) and radiolabeled using a Boehringer Mannheim (Indianapolis, Ind.) random priming labeling kit. The Northern filter is hybridized overnight in 50% formamide, 5× SSC, 50 mM sodium phosphate (pH7), 5× Denhardt's solution, 0.1% SDS, 5 mM EDTA and 0.1 mg/ml denatured DNA at 30° C. The filter is washed twice (15 minutes each wash) in 0.1× SSC, 0.1% SDS. Autoradiography of the hybridized filter reveals a strong hybridization signal to an approximately 1300 bp RNA band in the camphor embryo sample. This band is approximately the same size as the bay thioesterase mRNA.

To obtain a fragment of the camphor thioesterase gene, PCR is conducted using oligonucleotides to peptides conserved between the bay and safflower thioesterases. A comparison of the safflower and bay thioesterase translated amino acid sequence is presented in FIG. 8.

Polymerase chain reactions are conducted using reverse transcribed camphor RNA as template. The reactions are conducted in a Biosycler Oven (Bios Corp.; New Haven, Conn.) programmed for the following cycles:

| N | 95° C. for 2 min. | P | 95° C. for 15 sec. |
|---|---|---|---|
|   | 1 sec. drop to 65° C. |   | 1 sec. drop to 65° C. |
|   | hold 65° C. for 1 sec. |   | hold 65° C. for 1 sec. |
|   | 2 min. drop to 45° C. |   | 2 min. drop to 55° C. |
|   | hold 45° C. for 30 sec. |   | hold 55° C. for 15 sec. |
|   | 1 sec. rise to 72° C. |   | 1 sec. rise to 72° C. |
|   | hold 72° C. for 30 sec. |   | hold 72° C. for 15 sec. |
|   | 1 sec. rise to 95° C. |   | 1 sec. rise to 95° C. |

Cycle N is run and repeated 6 times after which cycle P is run and repeated 37 times.

An approximately 500–600 bp band is identified by agarose gel electrophoresis of the PCR products. This is the approximate fragment size predicted from analysis of the distance between the peptides in the bay thioesterase sequence. The PCR fragment is subcloned into an appropriate cloning vector and its DNA sequence determined to verify thioesterase sequence. DNA sequence of the camphor PCR fragment is presented in FIG. 5A. The fragment can then be utilized to screen a camphor cDNA or genomic library to isolate a camphor thioesterase clone.

Alternative to screening gene libraries, additional PCR techniques may be used to recover entire thioesterase encoding sequences. For example, the camphor thioesterase PCR fragment sequence is used to generate additional camphor thioesterase encoding sequence. For sequences 3' to the PCR fragment, the RACE procedure of Frohman et al. (*Proc. Nat. Acad. Sci.* (1988) 85:8998–9002) is utilized. Briefly, cDNA is generated from camphor endosperm poly(A)+ RNA using 200 ng of RNA, a poly(T) oligonucleotide (with 5' restriction recognition sites for EcoRI, XhoI and SalI) and reverse transcriptase. The product of this reaction is used in a PCR 3' RACE with an oligonucleotide encoding EcoRI, XhoI and SalI recognition sites and an oligonucleotide representing nucleotides 443–463 of the camphor gene fragment of FIG. 5A. The reaction is run in a Biosycler oven with the following program:

| 1 cycle at: | 94° C. for 40 sec. |
|---|---|
|   | 50° C. for 2 min. |
|   | 72° C. for 40 min. |
| 40 cycles at: | 94° C. for 40 sec. |
|   | 50° C. for 2 min. |
|   | 72° C. for 3 min. |

In this manner, an approximately 700 bp fragment representing the 3' portion of the camphor thioesterase gene sequence is obtained.

In addition, 5' sequence of the camphor thioesterase encoding sequence may also be obtained using PCR. For this reaction, cDNA to camphor endosperm poly(A)+ RNA is generated using random hexamer oligonucleotide primers in a reverse transcription reaction essentially as described by Frohman et al. (supra) The cDNA product of this reaction is A-tailed using terminal deoxynucleotide transferase and used in PCR. Oligonucleotide primers for this reaction are MET-1-2898, which contains nucleotides 140–155 of the bay thioesterase sequence in FIG. 1A and a 5' BamHI recognition site, and 2356, a degenerate oligonucleotide containing a sequence complementary to nucleotides 115–126 of the camphor thioesterase gene fragment of FIG. 5A. The reaction is run in a Biosycler oven with the following program:

| 35 cycles at: | 94° C. for 1 min. |
|---|---|
| | 55° C. for 1.5 min. |
| | 72° C. for 2.5 min. |

In this manner, an approximately 450 bp fragment representing the 5' portion of the camphor thioesterase gene sequence is obtained.

The various camphor thioesterase gene fragments are combined in a convenient cloning vector using restriction sites as inserted from the PCR procedures. Preliminary nucleic acid sequence and translated amino acid sequences of the camphor thioesterase gene generated in this manner is presented in FIG. 5B.

DNA sequences corresponding to *Cuphea thioesterase* may also be obtained using PCR methods. Degenerate oligonucleotides for use as primers may be designed from peptide fragments that are conserved between the bay, safflower and camphor thioesterase cDNA clones. The forward primer, TECU3, contains 18 nucleotides corresponding to all possible coding sequences for amino acids 283–288 of the bay (FIG. 1B) and camphor (FIG. 5B) thioesterase proteins, and amino acids 282–287 of the safflower thioesterase of FIG. 4A. The reverse primer, TECU4A, contains 17 nucleotides corresponding to all possible coding sequences for amino acids 315–320 of the bay (FIG. 1B) and camphor (FIG. 5B) thioesterase proteins, and amino acids 314–319 of the safflower thioesterase of FIG. 4A. In addition, the forward and reverse primers contain BamHI or XhoI restriction sites, respectively, at the 5' end, and an inosine nucleotide at the 3' end. Inosine residues at the 3' terminus have been reported to enhance amplification from degenerate oligonucleotide primers (Batzer et al. (1991) *Nucl. Acids Res.* 19:5081). The safflower peptides differ from the bay and camphor sequences in one amino acid in each of the designated peptide regions, and thus the oligonucleotide primers degeneracy is such that they encode both the safflower and bay/camphor sequences.

Polymerase chain reaction samples (100 µl) are prepared using reverse transcribed *Cuphea hookeriana* RNA as template and 1 µM of each of the oligonucleotide primers. Samples are boiled for 5 minutes and cooled to 75° C. prior to addition of Taq enzyme. PCR is conducted in a Perkin-Elmer thermocycler programmed for the following temperature cycle:

94° C. for 1 min.

65° C. for 1 sec.

2 min. drop to 40° C.

hold 40° C. for 30 sec.

1 min. rise to 72° C.

1 sec. rise to 94° C.

repeat cycle 40 times.

A termination cycle of 2 minutes at 72° C. is then run.

PCR products are analyzed by agarose gel electrophoresis, and an approximately 120 bp DNA fragment, the predicted size from the thioesterase peptide sequences, is observed. The DNA fragment is isolated and cloned into a convenient plasmid vector using the PCR-inserted BamHI and XhoI restriction digest sites. The cloned fragments are sequenced, and three clones are identified which match 21 out of 38 amino acids of the corresponding bay (FIG. 1B) thioesterase sequence (including the 12 amino acids encoded by the primers). Further comparison of one clone, CUPHEA-14-2, indicates that the translated peptide sequence matches 25 amino acids in the corresponding bay D (FIG. 3) region, 22 in the camphor thioesterase, and 22 and 23, respectively in the safflower 2-1 and 5-2 encoded thioesterase sequences. The DNA sequence of the CUPHEA-14-2 clone and amino acid translation of the thioesterase coding region are presented in FIG. 12. The thioesterase encoding fragment is labeled and used to screen a *Cuphea hookeriana* CDNA library to isolate the corresponding thioesterase cDNA.

Analysis of Thioesterase Sequences

Clones identified using DNA hybridization or immunological screening techniques are then purified and the DNA isolated using techniques as provided in Maniatis, et al. (supra). DNA sequence of the genes is determined to verify that the clones encode a related thioesterase. Alternatively, the protein is expressed in *E. coli* to show that it has the desired activity. The newly isolated plant thioesterase sequences can also be used to isolate genes for thioesterases from other plant species using the techniques described above.

For example, comparison of amino acid and nucleic acid sequences of the Bay, camphor and safflower thioesterases reveals homology that is useful for isolation of additional thioesterase genes. The bay and camphor clones demonstrate extensive homology, especially at the amino acid level, and may be useful for isolation of other thioesterases having similar short or medium-chain acyl-ACP substrate specificities, such as Cuphea, elm, nutmeg, etc. Similarly, the long chain thioesterase genes of safflower or Brassica, which have significant homology, may be useful for isolation of plant thioesterases having specificities for longer chain acyl-ACP substrates, such as those identified from Chinese tallow or cotton which have specificity for 16:0 fatty-acyl ACP and mango (18:0).

In addition, regions of the long chain thioesterase proteins and the short or medium-chain specific thioesterase proteins also demonstrate homology. These homologous regions may be useful for designing degenerate oligonucleotides for use in PCR to isolate additional plant thioesterases. For example, as described above, oligonucleotides to bay and safflower thioesterase regions were used to obtain camphor thioesterase encoding sequence. This conserved region corresponds to amino acids 113–119 of the bay and camphor amino acid sequences in FIGS. 1B and 5B, respectively and amino acids 108–114 of the safflower amino acid sequence in FIG. 4A. Similarly, other conserved regions are found in the bay, camphor and safflower amino acid sequences (as shown in FIGS. 1B, 5B and 4B, respectively), such as in 174–188 of bay and camphor and 169–183 of safflower; 219–229 of bay and camphor and 214–224 of safflower; and 138–145 of bay and camphor and 133–140 of safflower.

The above described plant acyl-ACP thioesterases are more highly conserved towards the center of the proteins than at either the carboxy- or amino-termini. The conserved regions may represent areas related to the catalytic site of the enzyme, and the observed substrate specificity differences may be related to the amino acid sequence differences in the regions at either end of the polypeptide chain. The plant acyl-ACP thioesterase protein sequences do not contain an active site consensus sequence (GHSxG) that is found in animal and yeast thioesterases and other fatty acid synthesis enzymes, or the active site motif of the cysteine-based hydrolases (Aitken (1990) in *Identification of Protein Consensus Sequences*, Ellis Horwood, London, pp. 81–91). As inhibitor studies indicate that the plant thioesterase enzymes are sensitive to sulfhydryl-specific reagents such as N-ethylmaleimide (Pollard, et al., supra), a cysteine residue may be involved at the active site.

Thus, other plant thioesterase genes may be isolated by the above described methods and used for expression of plant thioesterases. In particular, expression in *E. coli* will be useful for verifying the acyl chain length specificity of these thioesterases, and expression in plant seeds will be useful for producing modified oils.

Example 6
Plant Thioesterases and Dehydrases in Plants

The enzyme 3-hydroxydecanoyl-[acyl-carrier-protein] dehydratase (EC 4.2.1.60), also referred to herein as dehydrase, catalyzes the dehydration of 3-hydroxydecanoyl-ACP (C10:0-ACP) to 2-decenoyl-ACP (C10:1-ACP), a key step in the production of unsaturated fatty acids in bacteria. Expression of this enzyme in plant seeds is useful for production of unsaturated medium-chain acyl-ACPs in plants which also contain the bay medium-chain acyl-ACP thioesterase gene. In this manner, medium-chain unsaturated free fatty acids are formed as the result of hydrolysis activity of the bay thioesterase on C12:1 and C14:1 substrates.

A useful construct for expression of dehydrase in plant seeds provides for expression of the enzyme in plant seed tissue under control of a napin promoter region. In addition, a transit peptide region is provided for translocation of the dehydrase enzyme into plastids.

A dehydrase nucleic acid sequence from the *E. coli* dehydrase gene (Cronan et al. (1988) *J. Biol. Chem.* 263:4641–4646) is constructed, which encodes all but the initial Met amino acid of the dehydrase enzyme. A PCR DNA fragment which encodes the safflower thioesterase transit peptide and 6 amino acids of the mature safflower thioesterase (from clone 2-1) is inserted immediately 5' to the dehydrase such that the transit peptide and dehydrase sequences are in the same reading frame. The safflower thioesterase transit/dehydrase sequence is inserted into the napin expression cassette, pCGN3223, between the 5' and 3' napin regulatory sequences.

The dehydrase expression construct is transformed into a binary construct for plant transformation. A vector which encodes a selectable marker other than kanamycin is preferred. In this manner, transgenic Brassica plants which produce medium-chain acyl-ACP fatty acids as the result of an inserted bay thioesterase construct (such as those described in Example 4), may be re-transformed with the dehydrase expression construct. For example, the dehydrase expression construct may be inserted into a binary vector, pCGN2769 (described below), which encodes resistance to the antibiotic hygromycin B. Agrobacterium cells containing the resulting construct are obtained and used in Brassica transformation methods as described in Example 3.

The binary vector, pCGN2769, contains the right and left borders of Agrobacterium T-DNA, and between these borders, a 35S/hygromycin/tr7 construct for selection of transformed plant cells. The vector was constructed to be directly analogous to the binary vectors described by McBride and Summerfelt (supra), except for the use of an alternate selectable marker. The hph gene encoding hygromycin B phosphotransferase is described by Gritz and Davies (*Gene* (1983) 25:179–188). A DNA XhoI fragment containing the following hph and plant regulatory sequences was constructed using polymerase chain reaction techniques: −289 to +114 (relative to the transcriptional start site) of a CaMV35S promoter; hph coding region nucleotides 211–1236 (Gritz and Davies; supra), with the ATG initiation codon contained in the sequence ATCATGAAA, to provide a plant concensus translation initiation sequence (Kozak (1989) *J. Cell. Biol.* 108:229–241); an Agrobacterium transcript 7 (tr7) transcription termination region, from nucleotides 2921–2402 of T-DNA as numbered by Barker et al. (*Plant Mol. Biol.* (1983) 2:335–350). The XhoI hph expression fragment was ligated into pCGN1541 to create pCGN2768 which has a BglII fragment containing the left border of pTiA6 T-DNA, the hph expression construct, a HaeII fragment containing the 425 bp *E. coli* lac alpha encoding region, and the right border of pTiA6 T-DNA (T-DNA border and lac-α(regions are described in McBride et al. (supra). The above described BglII fragment is cloned into the unique BamHI fragment of pCGN1532 McBride et al. (supra) resulting in pCGN2769.

Alternatively, the dehydrase expression construct and a bay thioesterase expression construct (such as pCGN3828) may both be inserted into a single binary vector, such as the McBride et al. (supra) vectors which contain a marker for selection of kanamycin resistant plants. In either of these methods, plants which are able to produce medium-chain unsaturated and saturated fatty acids are produced.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

SEQUENCE LISTING ( 1 ) GENERAL INFORMATION:

( i i i ) NUMBER OF SEQUENCES: 11

( 2 ) INFORMATION FOR SEQ ID NO: 1:

(i) SEQUENCE CHARACTERISTICS:
    (A) LENGTH: 1561 base pairs
    (B) TYPE: nucleic acid
    (C) STRANDEDNESS: single
    (D) TOPOLOGY: linear (ii) MOLECULE TYPE: cDNA to mRNA (xi) SEQUENCE DESCRIPTION: SEQ ID NO: 1:

```
AGAGAGAGAG AGAGAGAGAG AGCTAAATTA AAAAAAAAAC CCAGAAGTGG GAAATCTTCC      60
CCATGAAATA ACGGATCCTC TTGCTACTGC TACTACTACT ACTACAAACT GTAGCCATTT     120
ATATAATTCT ATATAATTTT CAACATGGCC ACCACCTCTT TAGCTTCCGC TTTCTGCTCG     180
ATGAAAGCTG TAATGTTGGC TCGTGATGGC CGGGGCATGA AACCCAGGAG CAGTGATTTG     240
CAGCTGAGGG CGGGAAATGC GCCAACCTCT TTGAAGATGA TCAATGGGAC CAAGTTCAGT     300
TACACGGAGA GCTTGAAAAG GTTGCCTGAC TGGAGCATGC TCTTTGCAGT GATCACAACC     360
ATCTTTTCGG CTGCTGAGAA GCAGTGGACC AATCTAGAGT GGAAGCCGAA GCCGAAGCTA     420
CCCCAGTTGC TTGATGACCA TTTTGGACTG CATGGGTTAG TTTTCAGGCG CACCTTTGCC     480
ATCAGATCTT ATGAGGTGGG ACCTGACCGC TCCACATCTA TACTGGCTGT TATGAATCAC     540
ATGCAGGAGG CTACACTTAA TCATGCGAAG AGTGTGGGAA TTCTAGGAGA TGGATTCGGG     600
ACGACGCTAG AGATGAGTAA GAGAGATCTG ATGTGGGTTG TGAGACGCAC GCATGTTGCT     660
GTGGAACGGT ACCCTACTTG GGGTGATACT GTAGAAGTAG AGTGCTGGAT TGGTGCATCT     720
GGAAATAATG GCATGCGACG TGATTTCCTT GTCCGGGACT GCAAAACAGG CGAAATTCTT     780
ACAAGATGTA CCAGCCTTTC GGTGCTGATG AATACAAGGA CAAGGAGGTT GTCCACAATC     840
CCTGACGAAG TTAGAGGGGA GATAGGGCCT GCATTCATTG ATAATGTGGC TGTCAAGGAC     900
GATGAAATTA AGAAACTACA GAAGCTCAAT GACAGCACTG CAGATTACAT CCAAGGAGGT     960
TTGACTCCTC GATGGAATGA TTTGGATGTC AATCAGCATG TGAACAACCT CAAATACGTT    1020
GCCTGGGTTT TTGAGACCGT CCCAGACTCC ATCTTTGAGA GTCATCATAT TTCCAGCTTC    1080
ACTCTTGAAT ACAGGAGAGA GTGCACGAGG GATAGCGTGC TGCGGTCCCT GACCACTGTC    1140
TCTGGTGGCT CGTCGGAGGC TGGGTTAGTG TGCGATCACT TGCTCCAGCT TGAAGGTGGG    1200
TCTGAGGTAT TGAGGGCAAG AACAGAGTGG AGGCCTAAGC TTACCGATAG TTTCAGAGGG    1260
ATTAGTGTGA TACCCGCAGA ACCGAGGGTG TAACTAATGA AGAAGCATC TGTTGAAGTT     1320
TCTCCCATGC TGTTCGTGAG GATACTTTTT AGAAGCTGCA GTTTGCATTG CTTGTGCAGA    1380
ATCATGGTCT GTGGTTTTAG ATGTATATAA AAAATAGTCC TGTAGTCATG AAACTTAATA    1440
TCAGAAAAAT AACTCAATGG GTCAAGGTTA TCGAAGTAGT CATTTAAGCT TTGAAATATG    1500
TTTTGTATTC CTCGGCTTAA TCTGTAAGCT CTTTCTCTTG CAATAAAGTT CGCCTTTCAA    1560
T                                                                    1561
```

(2) INFORMATION FOR SEQ ID NO:2:

(i) SEQUENCE CHARACTERISTICS:
        (A) LENGTH: 382 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Thr Thr Ser Leu Ala Ser Ala Phe Cys Ser Met Lys Ala Val
 1               5                  10                  15

Met Leu Ala Arg Asp Gly Arg Gly Met Lys Pro Arg Ser Ser Asp Leu
```

```
                        20                          25                           30
Gln  Leu  Arg  Ala  Gly  Asn  Ala  Pro  Thr  Ser  Leu  Lys  Met  Ile  Asn  Gly
               35                       40                     45

Thr  Lys  Phe  Ser  Tyr  Thr  Glu  Ser  Leu  Lys  Arg  Leu  Pro  Asp  Trp  Ser
50                            55                      60

Met  Leu  Phe  Ala  Val  Ile  Thr  Thr  Ile  Phe  Ser  Ala  Ala  Glu  Lys  Gln
65                       70                      75                           80

Trp  Thr  Asn  Leu  Glu  Trp  Lys  Pro  Lys  Pro  Lys  Leu  Pro  Gln  Leu  Leu
                    85                      90                            95

Asp  Asp  His  Phe  Gly  Leu  His  Gly  Leu  Val  Phe  Arg  Arg  Thr  Phe  Ala
               100                 105                          110

Ile  Arg  Ser  Tyr  Glu  Val  Gly  Pro  Asp  Arg  Ser  Thr  Ser  Ile  Leu  Ala
          115                      120                      125

Val  Met  Asn  His  Met  Gln  Glu  Ala  Thr  Leu  Asn  His  Ala  Lys  Ser  Val
     130                      135                     140

Gly  Ile  Leu  Gly  Asp  Gly  Phe  Gly  Thr  Thr  Leu  Glu  Met  Ser  Lys  Arg
145                      150                     155                          160

Asp  Leu  Met  Trp  Val  Val  Arg  Arg  Thr  His  Val  Ala  Val  Glu  Arg  Tyr
                    165                      170                     175

Pro  Thr  Trp  Gly  Asp  Thr  Val  Glu  Val  Glu  Cys  Trp  Ile  Gly  Ala  Ser
               180                      185                     190

Gly  Asn  Asn  Gly  Met  Arg  Arg  Asp  Phe  Leu  Val  Arg  Asp  Cys  Lys  Thr
          195                      200                     205

Gly  Glu  Ile  Leu  Thr  Arg  Cys  Thr  Ser  Leu  Ser  Val  Leu  Met  Asn  Thr
     210                      215                     220

Arg  Thr  Arg  Arg  Leu  Ser  Thr  Ile  Pro  Asp  Glu  Val  Arg  Gly  Glu  Ile
225                           230                     235                     240

Gly  Pro  Ala  Phe  Ile  Asp  Asn  Val  Ala  Val  Lys  Asp  Asp  Glu  Ile  Lys
                    245                      250                     255

Lys  Leu  Gln  Lys  Leu  Asn  Asp  Ser  Thr  Ala  Asp  Tyr  Ile  Gln  Gly  Gly
               260                      265                     270

Leu  Thr  Pro  Arg  Trp  Asn  Asp  Leu  Asp  Val  Asn  Gln  His  Val  Asn  Asn
          275                      280                     285

Leu  Lys  Tyr  Val  Ala  Trp  Val  Phe  Glu  Thr  Val  Pro  Asp  Ser  Ile  Phe
     290                      295                     300

Glu  Ser  His  His  Ile  Ser  Ser  Phe  Thr  Leu  Glu  Tyr  Arg  Arg  Glu  Cys
305                           310                     315                     320

Thr  Arg  Asp  Ser  Val  Leu  Arg  Ser  Leu  Thr  Val  Ser  Gly  Gly  Ser
                    325                      330                     335

Ser  Glu  Ala  Gly  Leu  Val  Cys  Asp  His  Leu  Leu  Gln  Leu  Glu  Gly  Gly
               340                      345                     350

Ser  Glu  Val  Leu  Arg  Ala  Arg  Thr  Glu  Trp  Arg  Pro  Lys  Leu  Thr  Asp
          355                      360                     365

Ser  Phe  Arg  Gly  Ile  Ser  Val  Ile  Pro  Ala  Glu  Pro  Arg  Val
     370                      375                     380
```

(2) INFORMATION FOR SEQ ID NO:3:

(i) SEQUENCE CHARACTERISTICS:
(A) LENGTH: 1435 base pairs
(B) TYPE: nucleic acid
(C) STRANDEDNESS: single
(D) TOPOLOGY: linear (ii) MOLECULE TYPE: cDNA to mRNA (xi) SEQUENCE DESCRIPTION: SEQ ID NO: 3:

```
AAAAAAGTAC  AAACTGTATG  GTAGCCATTT  ACATATAACT  ACTCTATAAT  TTTCAAC ATG           60
                                                                    Met
                                                                     1

GTC ACC ACC TCT TTA GCT TCC GCT TTC TTC TCG ATG AAA GCT GTA ATG                  108
Val Thr Thr Ser Leu Ala Ser Ala Phe Phe Ser Met Lys Ala Val Met
            5               10              15

TTG GCT CCT GAT GGC AGT GGC ATA AAA CCC AGG AGC AGT GGT TTG CAG                  156
Leu Ala Pro Asp Gly Ser Gly Ile Lys Pro Arg Ser Ser Gly Leu Gln
        20              25              30

GTG AGG GCG GGA AAG GAA CAA AAC TCT TGC AAG ATG ATC AAT GGG ACC                  204
Val Arg Ala Gly Lys Glu Gln Asn Ser Cys Lys Met Ile Asn Gly Thr
    35              40              45

AAG GTC AAA GAC ACG GAG GGC TTG AAA GGG CGC AGC ACA TTG CAT GGC                  252
Lys Val Lys Asp Thr Glu Gly Leu Lys Gly Arg Ser Thr Leu His Gly
50              55              60              65

TGG AGC ATG CCC CTT GAA TTG ATC ACA ACC ATC TTT TCG GCT GCT GAG                  300
Trp Ser Met Pro Leu Glu Leu Ile Thr Thr Ile Phe Ser Ala Ala Glu
                70              75              80

AAG CAG TGG ACC AAT CTA GTT AGT AAG CCA CCG CAG TTG CTT GAT GAC                  348
Lys Gln Trp Thr Asn Leu Val Ser Lys Pro Pro Gln Leu Leu Asp Asp
            85              90              95

CAT TTA GGT CTG CAT GGG CTA GTT TTC AGG CGC ACC TTT GCA ATC AGA                  396
His Leu Gly Leu His Gly Leu Val Phe Arg Arg Thr Phe Ala Ile Arg
        100             105             110

TGC AGT GAG GTT GGA CCT GAC CGC TCC ACA TCC ATA GTG GCT GTT ATG                  444
Cys Ser Glu Val Gly Pro Asp Arg Ser Thr Ser Ile Val Ala Val Met
    115             120             125

AAT TAC TTG CAG GAA GCT GCA TGT AAT CAT GCG GAG AGT CTG GGA CTT                  492
Asn Tyr Leu Gln Glu Ala Ala Cys Asn His Ala Glu Ser Leu Gly Leu
130             135             140             145

CTA GGA GAT GGA TTC GGT GAG ACA CTA GAG ATG AGT AGG AGA GAT CTG                  540
Leu Gly Asp Gly Phe Gly Glu Thr Leu Glu Met Ser Arg Arg Asp Leu
                150             155             160

ATA TGG GTT GTG AGA CGC ACG CAT GTT GTT GTG GGA ACG TAC CCT GCT                  588
Ile Trp Val Val Arg Arg Thr His Val Val Val Gly Thr Tyr Pro Ala
            165             170             175

TGG GGC GAT ACT GTT GAA GTC GAG GCC TGG ATC GGT GCA GCT GGA AAC                  636
Trp Gly Asp Thr Val Glu Val Glu Ala Trp Ile Gly Ala Ala Gly Asn
        180             185             190

ATT GGC ATG CGC CGC CAT TTT CTT GTC CGC GAC TGC AAA ACT GGC CAC                  684
Ile Gly Met Arg Arg His Phe Leu Val Arg Asp Cys Lys Thr Gly His
    195             200             205

ATT CTT GCA AGA TGT ACC AGT GTT TCA GTG ATG ATG AAT ATG AGG ACA                  732
Ile Leu Ala Arg Cys Thr Ser Val Ser Val Met Met Asn Met Arg Thr
210             215             220             225

AGG AGA TTG TCC AAA ATT CCC CAA GAA GTT AGA GGG GAG ATT GAC CCT                  780
Arg Arg Leu Ser Lys Ile Pro Gln Glu Val Arg Gly Glu Ile Asp Pro
                230             235             240

CTT TTC ATC GAA AAG TTT GCT GTC AAG GAA GGG GAA ATT AAG AAA TTA                  828
Leu Phe Ile Glu Lys Phe Ala Val Lys Glu Gly Glu Ile Lys Lys Leu
            245             250             255

CAG AAG TTC AAT GAT AGC ACT GCA GAT TAC ATT CAA GGG GGT TGG ACT                  876
Gln Lys Phe Asn Asp Ser Thr Ala Asp Tyr Ile Gln Gly Gly Trp Thr
        260             265             270

CCG CGA TGG AAT GAT TTG GAT GTC AAT CAG CAC GTG AAC AAT ATC AAA                  924
Pro Arg Trp Asn Asp Leu Asp Val Asn Gln His Val Asn Asn Ile Lys
    275             280             285

TAC GTT GGC TGG ATT TTT AAG AGC GTC CCA GAC TCT ATC TAT GAG AAT                  972
Tyr Val Gly Trp Ile Phe Lys Ser Val Pro Asp Ser Ile Tyr Glu Asn
290             295             300             305
```

| | | | | | | | | | | | | | | | | |
|---|---|---|---|---|---|---|---|---|---|---|---|---|---|---|---|---|
| CAT | CAT | CTT | TCT | AGC | ATC | ACT | CTC | GAA | TAC | AGG | AGA | GAG | TGC | ACA | AGG | 1020 |
| His | His | Leu | Ser | Ser | Ile | Thr | Leu | Glu | Tyr | Arg | Arg | Glu | Cys | Thr | Arg | |
| | | | 310 | | | | | 315 | | | | | 320 | | | |
| GGC | AGA | GCA | CTG | CAG | TCC | CTG | ACC | ACT | GTT | TGT | GGT | GGC | TCG | TCC | GAA | 1068 |
| Gly | Arg | Ala | Leu | Gln | Ser | Leu | Thr | Thr | Val | Cys | Gly | Gly | Ser | Ser | Glu | |
| | | | 325 | | | | | 330 | | | | | 335 | | | |
| GCT | GGG | ATC | ATA | TGT | GAG | CAC | CTA | CTC | CAG | CTT | GAG | GAT | GGG | TCT | GAG | 1116 |
| Ala | Gly | Ile | Ile | Cys | Glu | His | Leu | Leu | Gln | Leu | Glu | Asp | Gly | Ser | Glu | |
| | | | 340 | | | | | 345 | | | | | 350 | | | |
| GTT | TTG | AGG | GGA | AGA | ACA | GAT | TGG | AGG | CCC | AAG | CGC | ACC | GAT | AGT | TTC | 1164 |
| Val | Leu | Arg | Gly | Arg | Thr | Asp | Trp | Arg | Pro | Lys | Arg | Thr | Asp | Ser | Phe | |
| | | | 355 | | | | | 360 | | | | | 365 | | | |
| GAA | GGC | ATT | AGT | GAG | AGA | TTC | CCG | CAG | CAA | GAA | CCG | CAT | AAT | TAAT | | 1210 |
| Glu | Gly | Ile | Ser | Glu | Arg | Phe | Pro | Gln | Gln | Glu | Pro | His | Asn | | | |
| 370 | | | | | 375 | | | | | 380 | | | | | | |

| | | | | |
|---|---|---|---|---|
| GACAGAAGCA | TCAGATATAG | TTTCTCCTGT | GCTGTTCCTG | AGAATGCATC | TTACAAGTCG | 1270 |
| TGGTTTGGAT | TGCTTGTGCA | GAATCATGGT | TTGTGCTTTC | AGAAGTATAT | CTAAATTAGT | 1330 |
| CCAAGTTATA | TGACTCCATA | TTGGAAAATA | ACTCAATGAG | TCGTGCTCTT | GAAATGGTCT | 1390 |
| TTTAAGCTTT | GAAATAAAGT | TCCACTTAAT | CCATGTAAAA | AAAAA | | 1435 |

( 2 ) INFORMATION FOR SEQ ID NO:4:

( i ) SEQUENCE CHARACTERISTICS:
        ( A ) LENGTH: 1561 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO: 4:

| | | | | |
|---|---|---|---|---|
| GGGTAACATG | GCATAAACGT | GAATAACTGC | AACTCCAGTG | TCACTTTCCC | TTTCCTTTCC | 60 |
| ACCACCATCT | CCTCCCTCGG | TCCCATCGAC | GGCAAACTCC | ATAAACCAC | CACCACCTCT | 120 |
| TCAAATCAAC | ACCTCTTCCG | AACCACCACC | ACCACCACCG | CCGCCGGCAA | CT ATG CTA | 178 |
| | | | | | Met Leu | |
| | | | | | 1 | |

| | | | | | | | | | | | | | | | | |
|---|---|---|---|---|---|---|---|---|---|---|---|---|---|---|---|---|
| TCA | CGA | CCT | CTT | CCG | ACC | ACC | GCC | GCG | GCG | GCG | ACC | ACG | ACG | ACG | AAT | 226 |
| Ser | Arg | Pro | Leu | Pro | Thr | Thr | Ala | Ala | Ala | Ala | Thr | Thr | Thr | Thr | Asn | |
| | | 5 | | | | | 10 | | | | | 15 | | | | |
| AAT | TGC | AAT | GGC | GTC | AAC | TCC | CGC | GGC | GCC | TTA | CCT | CAT | TCC | CGA | TCC | 274 |
| Asn | Cys | Asn | Gly | Val | Asn | Ser | Arg | Gly | Ala | Leu | Pro | His | Ser | Arg | Ser | |
| | 20 | | | | 25 | | | | | 30 | | | | | | |
| GTT | GGA | TTC | GCC | TCG | ATT | CGG | AAA | CGA | AGC | ACC | GGT | TCC | TTA | TGC | AAT | 322 |
| Val | Gly | Phe | Ala | Ser | Ile | Arg | Lys | Arg | Ser | Thr | Gly | Ser | Leu | Cys | Asn | |
| 35 | | | | | 40 | | | | | 45 | | | | | 50 | |
| TCG | CCG | CCG | CGG | ACG | GTG | GCG | CCG | GTG | ATG | GCG | GTG | AGG | ACC | GGT | GAG | 370 |
| Ser | Pro | Pro | Arg | Thr | Val | Ala | Pro | Val | Met | Ala | Val | Arg | Thr | Gly | Glu | |
| | | | 55 | | | | | 60 | | | | | 65 | | | |
| CAA | CCG | ACC | GGC | GTT | GCC | GTC | GGA | TTG | AAG | GAG | GCG | GAG | GCG | GAG | GTG | 418 |
| Gln | Pro | Thr | Gly | Val | Ala | Val | Gly | Leu | Lys | Glu | Ala | Glu | Ala | Glu | Val | |
| | | | 70 | | | | | 75 | | | | | 80 | | | |
| GAG | AAG | AGC | CTG | GCG | GAT | CGG | CTT | CGG | ATG | GGG | AGC | TTG | ACG | GAA | GAT | 466 |
| Glu | Lys | Ser | Leu | Ala | Asp | Arg | Leu | Arg | Met | Gly | Ser | Leu | Thr | Glu | Asp | |
| | | 85 | | | | | 90 | | | | | 95 | | | | |
| GGA | TTG | TCG | TAT | AAG | GAG | AGG | TTC | ATC | ATA | AGG | TGT | TAT | GAA | GTC | GGG | 514 |
| Gly | Leu | Ser | Tyr | Lys | Glu | Arg | Phe | Ile | Ile | Arg | Cys | Tyr | Glu | Val | Gly | |
| | | 100 | | | | | 105 | | | | | 110 | | | | |
| ATT | AAT | AAG | ACT | GCA | ACT | GTT | GAA | ACC | ATT | GCT | AAT | CTA | TTG | CAG | GAG | 562 |
| Ile | Asn | Lys | Thr | Ala | Thr | Val | Glu | Thr | Ile | Ala | Asn | Leu | Leu | Gln | Glu | |

-continued

```
 115                        120                        125                        130
GTT  GGA  GGT  AAT  CAT  GCT  CAG  AGT  GTT  GGA  TTT  TCA  ACA  GAC  GGA  TTT        610
Val  Gly  Gly  Asn  His  Ala  Gln  Ser  Val  Gly  Phe  Ser  Thr  Asp  Gly  Phe
               135                        140                        145

GCC  ACC  ACG  ACC  ACT  ATG  CGA  AAA  TTG  CAT  CTC  ATA  TGG  GTG  ACT  TCG        658
Ala  Thr  Thr  Thr  Thr  Met  Arg  Lys  Leu  His  Leu  Ile  Trp  Val  Thr  Ser
               150                        155                        160

CGA  ATG  CAC  ATT  GAA  ATT  TAC  AGA  TAC  CCC  GCT  TGG  AGT  GAT  GTG  GTT        706
Arg  Met  His  Ile  Glu  Ile  Tyr  Arg  Tyr  Pro  Ala  Trp  Ser  Asp  Val  Val
               165                        170                        175

GAA  ATC  GAG  ACT  TGG  TGT  CAA  AGT  GAA  GGA  AGG  ATT  GGG  ACT  AGA  CGT        754
Glu  Ile  Glu  Thr  Trp  Cys  Gln  Ser  Glu  Gly  Arg  Ile  Gly  Thr  Arg  Arg
          180                        185                        190

GAT  TGG  ATT  ATG  AAA  GAC  CAT  GCG  AGT  GGT  GAA  GTC  ATT  GGA  AGG  GCT        802
Asp  Trp  Ile  Met  Lys  Asp  His  Ala  Ser  Gly  Glu  Val  Ile  Gly  Arg  Ala
195                        200                        205                        210

ACA  AGC  AAA  TGG  GTG  ATG  ATG  AAC  GAG  GAT  ACT  AGA  AGA  CTC  CAG  AAA        850
Thr  Ser  Lys  Trp  Val  Met  Met  Asn  Glu  Asp  Thr  Arg  Arg  Leu  Gln  Lys
               215                        220                        225

GTC  AAC  GAT  GAC  GTC  AGA  GAC  GAA  TAT  CTC  GTT  TTT  TGT  CCC  AAG  ACA        898
Val  Asn  Asp  Asp  Val  Arg  Asp  Glu  Tyr  Leu  Val  Phe  Cys  Pro  Lys  Thr
               230                        235                        240

CCA  AGA  TTA  GCA  TTT  CCT  GAA  AAG  AAC  ACT  AGC  AGC  CTG  AAG  AAA  ATA        946
Pro  Arg  Leu  Ala  Phe  Pro  Glu  Lys  Asn  Thr  Ser  Ser  Leu  Lys  Lys  Ile
          245                        250                        255

GCA  AAA  CTA  GAA  GAC  CCC  GCC  GAA  TAT  TCG  ACG  CTA  GGG  CTT  GTG  CCA        994
Ala  Lys  Leu  Glu  Asp  Pro  Ala  Glu  Tyr  Ser  Thr  Leu  Gly  Leu  Val  Pro
260                        265                        270

AGA  AGA  GCC  GAT  CTC  GAT  ATG  AAC  AAG  CAT  GTT  AAC  AAT  GTT  ACC  TAC       1042
Arg  Arg  Ala  Asp  Leu  Asp  Met  Asn  Lys  His  Val  Asn  Asn  Val  Thr  Tyr
275                        280                        285                        290

ATT  GGA  TGG  GTT  CTT  GAG  AGC  ATC  CCA  CAA  GAA  GTC  ATC  GAC  ACT  CAT       1090
Ile  Gly  Trp  Val  Leu  Glu  Ser  Ile  Pro  Gln  Glu  Val  Ile  Asp  Thr  His
               295                        300                        305

GAA  CTA  CAA  ACG  ATT  ACC  CTA  GAC  TAC  CGG  CGG  GAA  TGC  CAG  CAT  GAC       1138
Glu  Leu  Gln  Thr  Ile  Thr  Leu  Asp  Tyr  Arg  Arg  Glu  Cys  Gln  His  Asp
          310                        315                        320

GAC  ATA  GTC  GAT  TCC  CTC  ACG  AGT  TCC  GAG  TCA  CTA  CTC  GAC  GAT  GCC       1186
Asp  Ile  Val  Asp  Ser  Leu  Thr  Ser  Ser  Glu  Ser  Leu  Leu  Asp  Asp  Ala
          325                        330                        335

GCC  ATC  TCG  AAA  CTC  GAA  GGA  ACC  AAC  GGA  TCT  TCT  GTT  CCC  AAA  AAA       1234
Ala  Ile  Ser  Lys  Leu  Glu  Gly  Thr  Asn  Gly  Ser  Ser  Val  Pro  Lys  Lys
          340                        345                        350

GAC  GAA  ACG  GAT  TTG  AGC  CGG  TTT  TTG  CAT  TTA  CTA  CGA  TCA  TCG  GGC       1282
Asp  Glu  Thr  Asp  Leu  Ser  Arg  Phe  Leu  His  Leu  Leu  Arg  Ser  Ser  Gly
355                        360                        365                        370

GAT  GGT  CTC  GAA  CTA  AAT  AGG  GGT  CGC  ACC  GAG  TGG  AGA  AAG  AAA  CCC       1330
Asp  Gly  Leu  Glu  Leu  Asn  Arg  Gly  Arg  Thr  Glu  Trp  Arg  Lys  Lys  Pro
               375                        380                        385

GCG  AAA  AAA  TGAGCAACAC  CCTTCGGTTT  GTTTAGCGTA  CCCTTTTTTG                         1379
Ala  Lys  Lys

CGTGTTTTCA  ATCCATTTTT  CATAATTCGC  CTTTTAGGGN  NNNGCCGTTT  TTATGTAGCG               1439

TATTTGTTGT  AGATGGACTA  GGTTTTCGGA  TTCTCGAACC  GGATAGGTGC  TATCTTTATC               1499

TTCCTATGTT  TTGCTTGTAG  AATGGTATGA  ATAAACTAGT  TTCGAAGTAA  TGTTTTTGGT               1559

AG                                                                                   1561
```

( 2 ) INFORMATION FOR SEQ ID NO:5:

5,807,893

47

48

-continued ( i ) SEQUENCE CHARACTERISTICS:
    ( A ) LENGTH: 1312 base pairs
    ( B ) TYPE: nucleic acid
    ( C ) STRANDEDNESS: single
    ( D ) TOPOLOGY: linear ( i i ) MOLECULE TYPE: cDNA to mRNA ( x i ) SEQUENCE DESCRIPTION: SEQ ID NO: 5:

```
GCACAAACCA GGAAAAAAAA AACCCTCTCT CCCTAACCTA ACTCGCCATC GGAGAAATCT                    60

CTGTCGACGG TGACGTTCGA GATCGTAACA ATC ATG CTA TCG AAA GGT GCT CCG                   114
                                     Met Leu Ser Lys Gly Ala Pro
                                      1               5

GCG GCA CCG GCG GTG GCG GCG ATG TAC AAT GCC TCC GCC AAA GAC ACT                    162
Ala Ala Pro Ala Val Ala Ala Met Tyr Asn Ala Ser Ala Lys Asp Thr
         10              15                  20

ACT TTT GCC CTA ACT CAC TCC CGA TCG ATT GGT TCC GTC TCA ATT CGC                    210
Thr Phe Ala Leu Thr His Ser Arg Ser Ile Gly Ser Val Ser Ile Arg
     25              30              35

AGA CGA TAC AAC GTG TTT TTG TGC AAT TCT TCG TCG TCG TCG AGA AAG                    258
Arg Arg Tyr Asn Val Phe Leu Cys Asn Ser Ser Ser Ser Ser Arg Lys
 40              45              50                  55

GTT TCT CCG TTG CTA GCG GTG GCG ACC GGA GAG CAG CCG AGC GGT GTT                    306
Val Ser Pro Leu Leu Ala Val Ala Thr Gly Glu Gln Pro Ser Gly Val
             60              65                  70

GCT AGT TTA CGT GAG GCG GAT AAG GAG AAG AGC TTG GGG AAC CGG CTA                    354
Ala Ser Leu Arg Glu Ala Asp Lys Glu Lys Ser Leu Gly Asn Arg Leu
             75              80              85

CGG TTG GGG AGC TTG ACG GAG GAT GGA TTA TCG TAT AAG GAG AAG TTC                    402
Arg Leu Gly Ser Leu Thr Glu Asp Gly Leu Ser Tyr Lys Glu Lys Phe
         90              95              100

GTT ATA AGG TGT TAT GAA GTC GGA ATT AAC AAA ACT GCT ACG ATT GAA                    450
Val Ile Arg Cys Tyr Glu Val Gly Ile Asn Lys Thr Ala Thr Ile Glu
     105             110             115

ACG ATT GCA AAT CTG TTG CAG GAG GTT GGA GGT AAT CAT GCT CAG GGT                    498
Thr Ile Ala Asn Leu Leu Gln Glu Val Gly Gly Asn His Ala Gln Gly
120             125             130             135

GTT GGA TTT TCT ACT GAT GGG TTT GCC ACA ACG ACC ACT ATG AGG AAA                    546
Val Gly Phe Ser Thr Asp Gly Phe Ala Thr Thr Thr Thr Met Arg Lys
             140             145             150

TTG CAT CTC ATA TGG GTT ACT GCA CGA ATG CAT ATT GAA ATA TAT AGA                    594
Leu His Leu Ile Trp Val Thr Ala Arg Met His Ile Glu Ile Tyr Arg
             155             160             165

TAC CCT GCT TGG AGT GAT GTG ATT GAA ATT GAG ACT TGG GTT CAG GGT                    642
Tyr Pro Ala Trp Ser Asp Val Ile Glu Ile Glu Thr Trp Val Gln Gly
         170             175             180

GAG GGG AAG GTC GGG ACC AGG CGT GAT TGG ATC CTC AAA GAC TAT GCC                    690
Glu Gly Lys Val Gly Thr Arg Arg Asp Trp Ile Leu Lys Asp Tyr Ala
     185             190             195

AAT GGT GAG GTT ATT GGA AGG GCC ACA AGC AAA TGG GTG ATG ATG AAC                    738
Asn Gly Glu Val Ile Gly Arg Ala Thr Ser Lys Trp Val Met Met Asn
200             205             210             215

GAG GAT ACT AGA AGA TTG CAG AAA GTC AGT GAT GAT GTC AGA GAG GAG                    786
Glu Asp Thr Arg Arg Leu Gln Lys Val Ser Asp Asp Val Arg Glu Glu
             220             225             230

TAT TTA GTG TTT TGC CCC AGG ACA TTG AGA TTA GCA TTT CCT GAA GAG                    834
Tyr Leu Val Phe Cys Pro Arg Thr Leu Arg Leu Ala Phe Pro Glu Glu
             235             240             245

AAC AAC AAT AGC ATG AAG AAA ATA CCA AAA CTG GAA GAT CCA GCT GAA                    882
Asn Asn Asn Ser Met Lys Lys Ile Pro Lys Leu Glu Asp Pro Ala Glu
             250             255             260
```

| | | | | | | | | | | | | | | | | |
|---|---|---|---|---|---|---|---|---|---|---|---|---|---|---|---|---|
| TAT | TCC | AGG | CTT | GGA | CTT | GTG | CCA | AGG | AGA | TCC | GAT | TTG | GAT | ATG | AAC | 930 |
| Tyr | Ser | Arg | Leu | Gly | Leu | Val | Pro | Arg | Arg | Ser | Asp | Leu | Asp | Met | Asn | |
| | 265 | | | | 270 | | | | | 275 | | | | | | |
| AAA | CAC | GTT | AAC | AAT | GTT | ACC | TAC | ATC | GGG | TGG | GCT | CTA | GAG | AGC | ATC | 978 |
| Lys | His | Val | Asn | Asn | Val | Thr | Tyr | Ile | Gly | Trp | Ala | Leu | Glu | Ser | Ile | |
| 280 | | | | | 285 | | | | | 290 | | | | | 295 | |
| CCA | CCA | GAA | ATC | ATC | GAC | ACC | CAT | GAA | CTG | CAA | GCT | ATT | ACC | TTA | GAC | 1026 |
| Pro | Pro | Glu | Ile | Ile | Asp | Thr | His | Glu | Leu | Gln | Ala | Ile | Thr | Leu | Asp | |
| | | | | 300 | | | | 305 | | | | | 310 | | | |
| TAC | AGA | CGT | GAA | TGC | CAA | CGG | GAT | GAC | ATA | GTT | GAT | TCA | CTC | ACT | AGC | 1074 |
| Tyr | Arg | Arg | Glu | Cys | Gln | Arg | Asp | Asp | Ile | Val | Asp | Ser | Leu | Thr | Ser | |
| | | | 315 | | | | | 320 | | | | | 325 | | | |
| CGT | GAA | CCA | CTC | GGA | AAT | GCT | GCA | GGT | GTC | AAG | TTT | AAA | GAA | ATC | AAT | 1122 |
| Arg | Glu | Pro | Leu | Gly | Asn | Ala | Ala | Gly | Val | Lys | Phe | Lys | Glu | Ile | Asn | |
| | | 330 | | | | | 335 | | | | | 340 | | | | |
| GGA | TCT | GTT | TCC | CCC | AAA | AAG | GAC | GAA | CAA | GAT | CTA | AGC | CGA | TTT | ATG | 1170 |
| Gly | Ser | Val | Ser | Pro | Lys | Lys | Asp | Glu | Gln | Asp | Leu | Ser | Arg | Phe | Met | |
| | 345 | | | | | 350 | | | | | 355 | | | | | |
| CAT | CTA | CTG | AGA | TCA | GCT | GGC | AGT | GGT | CTT | GAA | ATC | AAC | AGG | TGT | CGC | 1218 |
| His | Leu | Leu | Arg | Ser | Ala | Gly | Ser | Gly | Leu | Glu | Ile | Asn | Arg | Cys | Arg | |
| 360 | | | | | 365 | | | | | 370 | | | | | 375 | |
| ACC | GAA | TGG | AGA | AAG | AAG | CCA | GCA | AAA | AGA | TAAGCATATC | | TGATCCCTCG | | | | 1268 |
| Thr | Glu | Trp | Arg | Lys | Lys | Pro | Ala | Lys | Arg | | | | | | | |
| | | | 380 | | | | | 385 | | | | | | | | |

ATTGTACCGT TTTACCGTTC CTGTTCAAAG TCTAGTTTCT TTTT    1312

( 2 ) INFORMATION FOR SEQ ID NO:6:

( i ) SEQUENCE CHARACTERISTICS:
        ( A ) LENGTH: 540 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO: 6:

GGATCCATTA GCAGGTAGGA GGTCGGACCT GACCGCTCCA CATCTATAGT GGCTGTTATG    60

AATCACTTGC AGGAGGCTGC ACTTAATCAT GCGAAGAGTG TGGGAATTCT AGGAGATGGA    120

TTCGGTACGA CGCTAGAGAT GAGTAAGAGA GATCTGATAT GGGTTGTGAA ACGCACGCAT    180

GTTGCTGTGG AACGGTACCC TGCTTGGGGT GATACTGTTG AAGTAGAGTG CTGGGTTGGT    240

GCATCGGGAA ATAATGGCAG GCGCCATGAT TTCCTTGTCC GGGACTGCAA AACAGGCGAA    300

ATTCTTACAA GATGTACCAG TCTTTCGGTG ATGATGAATA CAAGGACAAG GAGGTTGTCC    360

AAAATCCCTG AAGAAGTTAG AGGGGAGATA GGGCCTGCAT TCATTGATAA TGTGGCTGTC    420

AAGGACGAGG AAATTAAGAA ACCACAGAAG CTCAATGACA GCACTGCAGA TTACATCCAA    480

GGAGGATTGA CTCCTCGATG GAATGATTTG GATATCAATA AGCATGTCAA CAACCTCGAG    540

( 2 ) INFORMATION FOR SEQ ID NO:7:

( i ) SEQUENCE CHARACTERISTICS:
        ( A ) LENGTH: 1461 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO: 7:

| | | | | | | | | | | | | | | | | |
|---|---|---|---|---|---|---|---|---|---|---|---|---|---|---|---|---|
| TCAAC | ATG | GCC | ACC | ACC | TCT | TTA | GCT | TCT | GCT | TTC | TGC | TCG | ATG | AAA | GCT | 50 |
| | Met | Ala | Thr | Thr | Ser | Leu | Ala | Ser | Ala | Phe | Cys | Ser | Met | Lys | Ala | |

-continued

```
                1                   5                           10                              15

GTA  ATG  TTG  GCT  CGT  GAT  GGC  AGG  GGC  ATG  AAA  CCC  AGG  AGC  AGT  GAT                98
Val  Met  Leu  Ala  Arg  Asp  Gly  Arg  Gly  Met  Lys  Pro  Arg  Ser  Ser  Asp
                    20                        25                        30

TTG  CAG  CTG  AGG  GCG  GGA  AAT  GCA  CAA  ACC  TCT  TTG  AAG  ATG  ATC  AAT              146
Leu  Gln  Leu  Arg  Ala  Gly  Asn  Ala  Gln  Thr  Ser  Leu  Lys  Met  Ile  Asn
              35                        40                        45

GGG  ACC  AAG  TTC  AGT  TAC  ACA  GAG  AGC  TTG  AAA  AAG  TTG  CCT  GAC  TGG              194
Gly  Thr  Lys  Phe  Ser  Tyr  Thr  Glu  Ser  Leu  Lys  Lys  Leu  Pro  Asp  Trp
              50                        55                        60

AGC  ATG  CTC  TTT  GCA  GTG  ATC  ACG  ACC  ATC  TTT  TCG  GCT  GCT  GAG  AAG              242
Ser  Met  Leu  Phe  Ala  Val  Ile  Thr  Thr  Ile  Phe  Ser  Ala  Ala  Glu  Lys
         65                        70                        75

CAG  TGG  ACC  AAT  CTA  GAG  TGG  AAG  CCG  AAG  CCG  AAT  CCA  CCC  CAG  TTG              290
Gln  Trp  Thr  Asn  Leu  Glu  Trp  Lys  Pro  Lys  Pro  Asn  Pro  Pro  Gln  Leu
80                       85                        90                        95

CTT  GAT  GAC  CAT  TTT  GGG  CCG  CAT  GGG  TTA  GTT  TTC  AGG  CGC  ACC  TTT              338
Leu  Asp  Asp  His  Phe  Gly  Pro  His  Gly  Leu  Val  Phe  Arg  Arg  Thr  Phe
                        100                       105                       110

GCC  ATC  AGA  TCG  TAT  GAG  GTG  GGA  CCT  GAC  CGC  TCC  ACA  TCT  ATA  GTG              386
Ala  Ile  Arg  Ser  Tyr  Glu  Val  Gly  Pro  Asp  Arg  Ser  Thr  Ser  Ile  Val
                   115                       120                       125

GCT  GTT  ATG  AAT  CAC  TTG  CAG  GAG  GCT  GCA  CTT  AAT  CAT  GCG  AAG  AGT              434
Ala  Val  Met  Asn  His  Leu  Gln  Glu  Ala  Ala  Leu  Asn  His  Ala  Lys  Ser
              130                       135                       140

GTG  GGA  ATT  CTA  GGA  GAT  GGA  TTC  GGT  ACG  ACG  CTA  GAG  ATG  AGT  AAG              482
Val  Gly  Ile  Leu  Gly  Asp  Gly  Phe  Gly  Thr  Thr  Leu  Glu  Met  Ser  Lys
              145                       150                       155

AGA  GAT  CTG  ATA  TGG  GTT  GTG  AAA  CGC  ACG  CAT  GTT  GCT  GTG  GAA  CGG              530
Arg  Asp  Leu  Ile  Trp  Val  Val  Lys  Arg  Thr  His  Val  Ala  Val  Glu  Arg
160                       165                       170                       175

TAC  CCT  GCT  TGG  GGT  GAT  ACT  GTT  GAA  GTA  GAG  TGC  TGG  GTT  GGT  GCA              578
Tyr  Pro  Ala  Trp  Gly  Asp  Thr  Val  Glu  Val  Glu  Cys  Trp  Val  Gly  Ala
                        180                       185                       190

TCG  GGA  AAT  AAT  GGC  AGG  CGC  CAT  GAT  TTC  CTT  GTC  CGG  GAC  TGC  AAA              626
Ser  Gly  Asn  Asn  Gly  Arg  Arg  His  Asp  Phe  Leu  Val  Arg  Asp  Cys  Lys
                   195                       200                       205

ACA  GGC  GAA  ATT  CTT  ACA  AGA  TGT  ACC  AGT  CTT  TCG  GTG  ATG  ATG  AAT              674
Thr  Gly  Glu  Ile  Leu  Thr  Arg  Cys  Thr  Ser  Leu  Ser  Val  Met  Met  Asn
              210                       215                       220

ACA  AGG  ACA  AGG  AGG  TTG  TCC  AAA  ATC  CCT  GAA  GAA  GTT  AGA  GGG  GAG              722
Thr  Arg  Thr  Arg  Arg  Leu  Ser  Lys  Ile  Pro  Glu  Glu  Val  Arg  Gly  Glu
         225                       230                       235

ATA  GGG  CCT  GCA  TTC  ATT  GAT  AAT  GTG  GCT  GTC  AAG  GAC  GAG  GAA  ATT              770
Ile  Gly  Pro  Ala  Phe  Ile  Asp  Asn  Val  Ala  Val  Lys  Asp  Glu  Glu  Ile
240                       245                       250                       255

AAG  AAA  CCA  CAG  AAG  CTC  AAT  GAC  AGC  ACT  GCA  GAT  TAC  ATC  CAA  GGA              818
Lys  Lys  Pro  Gln  Lys  Leu  Asn  Asp  Ser  Thr  Ala  Asp  Tyr  Ile  Gln  Gly
                        260                       265                       270

GGA  TTG  ACT  CCT  CGA  TGG  AAT  GAT  TTG  GAT  ATC  AAT  CAG  CAC  GTT  AAC              866
Gly  Leu  Thr  Pro  Arg  Trp  Asn  Asp  Leu  Asp  Ile  Asn  Gln  His  Val  Asn
                   275                       280                       285

AAC  ATC  AAA  TAC  GTT  GAC  TGG  ATT  CTT  GAG  ACT  GTC  CCA  GAC  TCA  ATC              914
Asn  Ile  Lys  Tyr  Val  Asp  Trp  Ile  Leu  Glu  Thr  Val  Pro  Asp  Ser  Ile
              290                       295                       300

TTT  GAG  AGT  CAT  CAT  ATT  TCC  AGC  TTC  ACT  ATT  GAA  TAC  AGG  AGA  GAG              962
Phe  Glu  Ser  His  His  Ile  Ser  Ser  Phe  Thr  Ile  Glu  Tyr  Arg  Arg  Glu
         305                       310                       315

TGC  ACG  ATG  GAT  AGC  GTG  CTG  CAG  TCC  CTG  ACC  ACT  GTC  TCC  GGT  GGC             1010
Cys  Thr  Met  Asp  Ser  Val  Leu  Gln  Ser  Leu  Thr  Thr  Val  Ser  Gly  Gly
```

```
                 320                           325                           330                           335
TCG  TCG  GAA  GCT  GGG  TTA  GTG  TGC  GAG  CAC  TTG  CTC  CAG  CTT  GAA  GGT                        1058
Ser  Ser  Glu  Ala  Gly  Leu  Val  Cys  Glu  His  Leu  Leu  Gln  Leu  Glu  Gly
                    340                      345                           350

GGG  TCT  GAG  GTA  TTG  AGG  GCA  AAA  ACA  GAG  TGG  AGG  CCT  AAG  CTT  ACC                        1106
Gly  Ser  Glu  Val  Leu  Arg  Ala  Lys  Thr  Glu  Trp  Arg  Pro  Lys  Leu  Thr
                    355                      360                           365

GAT  AGT  TTC  AGA  GGG  ATT  AGT  GTG  ATA  CCC  GCA  GAA  TCG  AGT  GTC                             1151
Asp  Ser  Phe  Arg  Gly  Ile  Ser  Val  Ile  Pro  Ala  Glu  Ser  Ser  Val
                    370                      375                           380

TAACTAACGA  AAGAAGCATC  TGATGAAGTT  TCTCCTGTGC  TGTTGTTCGT  GAGGATGCTT                                 1211

TTTAGAAGCT  GCAGTTTGCA  TTGCTTGTGC  AGAATCATGG  CCTGTGGTTT  TAGATATATA                                 1271

TCCAAAATTG  TCCTATAGTC  AAGAAACTTA  ATATCAGAAA  ATAACTCAA   TGAGTCAAGG                                 1331

TTATCGAAGT  AGTCATGTAA  GCTTTGAAAT  ATGTTGTGTA  TTCCTCGGCT  TTATGTAATC                                 1391

TGTAAGCTCT  TTCTCTTGCA  ATAAATTTCG  CCTTTCAATA  ATAAAAAAAA  AAAAAAAAGG                                 1451

TCGACTCGAG                                                                                              1461

( 2 ) INFORMATION FOR SEQ ID NO:8:

( i ) SEQUENCE CHARACTERISTICS:
            ( A ) LENGTH: 1307 base pairs
            ( B ) TYPE: nucleic acid
            ( C ) STRANDEDNESS: single
            ( D ) TOPOLOGY: linear ( i i ) MOLECULE TYPE: cDNA to mRNA ( x i ) SEQUENCE DESCRIPTION: SEQ ID NO: 8:

GCTCGCCTCC  CACATTTTCT  TCTTCGATCC  CGAAAAG  ATG  TTG  AAG  CTC  TCG  TGT                              55
                                             Met  Leu  Lys  Leu  Ser  Cys
                                              1                        5

AAT  GCG  ACT  GAT  AAG  TTA  CAG  ACC  CTC  TTC  TCG  CAT  TCT  CAT  CAA  CCG                        103
Asn  Ala  Thr  Asp  Lys  Leu  Gln  Thr  Leu  Phe  Ser  His  Ser  His  Gln  Pro
                    10                       15                           20

GAT  CCG  GCA  CAC  CGG  AGA  ACC  GTC  TCC  TCC  GTG  TCG  TGC  TCT  CAT  CTG                        151
Asp  Pro  Ala  His  Arg  Arg  Thr  Val  Ser  Ser  Val  Ser  Cys  Ser  His  Leu
                    25                       30                           35

AGG  AAA  CCG  GTT  CTC  GAT  CCT  TTG  CGA  GCG  ATC  GTA  TCT  GCT  GAT  CAA                        199
Arg  Lys  Pro  Val  Leu  Asp  Pro  Leu  Arg  Ala  Ile  Val  Ser  Ala  Asp  Gln
                    40                       45                           50

GGA  AGT  GTG  ATT  CGA  GCA  GAA  CAA  GGT  TTG  GGC  TCA  CTC  GCG  GAT  CAG                        247
Gly  Ser  Val  Ile  Arg  Ala  Glu  Gln  Gly  Leu  Gly  Ser  Leu  Ala  Asp  Gln
55                       60                       65                       70

CTC  CGA  TTG  GGT  AGC  TTG  ACG  GAG  GAT  GGT  TTG  TCG  TAT  AAG  GAG  AAG                        295
Leu  Arg  Leu  Gly  Ser  Leu  Thr  Glu  Asp  Gly  Leu  Ser  Tyr  Lys  Glu  Lys
                    75                       80                           85

TTC  ATC  GTC  AGA  TCC  TAC  GAA  GTG  GGG  AGT  AAC  AAG  ACC  GCC  ACT  GTC                        343
Phe  Ile  Val  Arg  Ser  Tyr  Glu  Val  Gly  Ser  Asn  Lys  Thr  Ala  Thr  Val
                    90                       95                           100

GAA  ACC  GTC  GCT  AAT  CTT  TTG  CAG  GAG  GTG  GGA  TGT  AAT  CAT  GCG  CAG                        391
Glu  Thr  Val  Ala  Asn  Leu  Leu  Gln  Glu  Val  Gly  Cys  Asn  His  Ala  Gln
                    105                      110                          115

AGC  GTT  GGA  TTC  TCG  ACT  GAT  GGG  TTT  GCG  ACA  ACA  CCG  ACC  ATG  AGG                        439
Ser  Val  Gly  Phe  Ser  Thr  Asp  Gly  Phe  Ala  Thr  Thr  Pro  Thr  Met  Arg
                    120                      125                          130

AAA  CTG  CAT  CTC  ATT  TGG  GTC  ACT  GCG  AGA  ATG  CAT  ATA  GAG  ATC  TAC                        487
Lys  Leu  His  Leu  Ile  Trp  Val  Thr  Ala  Arg  Met  His  Ile  Glu  Ile  Tyr
135                      140                      145                      150

AAG  TAC  CCT  GCT  TGG  GGT  GAT  GTG  GTT  GAG  ATA  GAG  ACA  TGG  TGT  CAG                        535
```

| | | | | | | | | | | | | | | | | |
|---|---|---|---|---|---|---|---|---|---|---|---|---|---|---|---|---|
| Lys | Tyr | Pro | Ala | Trp<br>155 | Gly | Asp | Val | Val | Glu<br>160 | Ile | Glu | Thr | Trp | Cys<br>165 | Gln | |
| AGT | GAA | GGA | AGG | ATC | GGG | ACT | AGG | CGT | GAT | TGG | ATT | CTT | AAG | GAT | GTT | 583 |
| Ser | Glu | Gly | Arg<br>170 | Ile | Gly | Thr | Arg | Arg<br>175 | Asp | Trp | Ile | Leu | Lys<br>180 | Asp | Val | |
| GCT | ACG | GGT | GAA | GTC | ACT | GGC | CGT | GCT | ACA | AGC | AAG | TGG | GTG | ATG | ATG | 631 |
| Ala | Thr | Gly<br>185 | Glu | Val | Thr | Gly | Arg<br>190 | Ala | Thr | Ser | Lys | Trp<br>195 | Val | Met | Met | |
| AAC | CAA | GAC | ACA | AGA | CGG | CTT | CAG | AAA | GTT | TCT | GAT | GAT | GTT | CGG | GAC | 679 |
| Asn | Gln<br>200 | Asp | Thr | Arg | Arg | Leu<br>205 | Gln | Lys | Val | Ser | Asp<br>210 | Asp | Val | Arg | Asp | |
| GAG | TAC | TTG | GTC | TTC | TGT | CCT | AAA | GAA | CTC | AGA | TTA | GCA | TTT | CCT | GAG | 727 |
| Glu<br>215 | Tyr | Leu | Val | Phe | Cys<br>220 | Pro | Lys | Glu | Leu | Arg<br>225 | Leu | Ala | Phe | Pro | Glu<br>230 | |
| GAG | AAT | AAC | AGA | AGC | TTG | AAG | AAA | ATT | CCG | AAA | CTC | GAA | GAT | CCA | GCT | 775 |
| Glu | Asn | Asn | Arg | Ser<br>235 | Leu | Lys | Lys | Ile | Pro<br>240 | Lys | Leu | Glu | Asp | Pro<br>245 | Ala | |
| CAG | TAT | TCG | ATG | ATT | GGG | CTT | AAG | CCT | AGA | CGA | GCT | GAT | CTC | GAC | ATG | 823 |
| Gln | Tyr | Ser | Met<br>250 | Ile | Gly | Leu | Lys | Pro<br>255 | Arg | Arg | Ala | Asp | Leu<br>260 | Asp | Met | |
| AAC | CAG | CAT | GTC | AAT | AAT | GTC | ACC | TAT | ATT | GGA | TGG | GTT | CTT | GAG | AGC | 871 |
| Asn | Gln | His<br>265 | Val | Asn | Asn | Val | Thr<br>270 | Tyr | Ile | Gly | Trp | Val<br>275 | Leu | Glu | Ser | |
| ATA | CCT | CAA | GAG | ATT | GTA | GAC | ACG | CAC | GAA | CTT | CAG | GTC | ATA | ACT | CTG | 919 |
| Ile | Pro<br>280 | Gln | Glu | Ile | Val | Asp<br>285 | Thr | His | Glu | Leu | Gln<br>290 | Val | Ile | Thr | Leu | |
| GAT | TAC | AGA | AGA | GAA | TGT | CAA | CAA | GAC | GAT | GTG | GTG | GAT | TCA | CTC | ACC | 967 |
| Asp | Tyr | Arg | Arg<br>295 | Glu | Cys | Gln<br>300 | Gln | Asp | Asp | Val<br>305 | Val | Asp | Ser | Leu | Thr<br>310 | |
| ACT | ACC | ACC | TCA | GAG | ATT | GGT | GGG | ACC | AAT | GGC | TCT | GCA | TCA | TCA | GGC | 1015 |
| Thr | Thr | Thr | Ser<br>315 | Glu | Ile | Gly | Gly | Thr<br>320 | Asn | Gly | Ser | Ala | Ser<br>325 | Ser | Gly | |
| ACA | CAG | GGG | CAA | AAC | GAT | AGC | CAG | TTC | TTA | CAT | CTC | TTA | AGG | CTG | TCT | 1063 |
| Thr | Gln | Gly<br>330 | Gln | Asn | Asp | Ser | Gln<br>335 | Phe | Leu | His | Leu | Leu<br>340 | Arg | Leu | Ser | |
| GGA | GAC | GGT | CAG | GAG | ATC | AAC | CGC | GGG | ACA | ACC | CTG | TGG | AGA | AAG | AAG | 1111 |
| Gly | Asp | Gly<br>345 | Gln | Glu | Ile | Asn | Arg<br>350 | Gly | Thr | Thr | Leu | Trp<br>355 | Arg | Lys | Lys | |
| CCC | TCC | AAT | CTC | TAAGCCATTT | | CGTTCTTAAG | | TTTCCTCTAT | | CTGTGTCGCT | | | | | | 1163 |
| Pro | Ser | Asn<br>360 | Leu | | | | | | | | | | | | | |

CGATGCTTCA CGAGTCTAGT CAGGTCTCAT TTTTTTCAAT CTAAATTTGG GTTAGACTAG 1223

AGAACTGGAA TTATTGGAAT TTATGAGTTT TCGTTCTTGT TTCTGTACAA ATCTTGAGGA 1283

TTGAAGCCAA ACCCATTTCA TCTT 1307

( 2 ) INFORMATION FOR SEQ ID NO:9:

( i ) SEQUENCE CHARACTERISTICS:
        ( A ) LENGTH: 325 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 9:

| | | | | | | | | | |
|---|---|---|---|---|---|---|---|---|---|
| Ala<br>1 | Val | Ala | Thr | Gly<br>5 | Glu | Gln | Pro | Ser | Val<br>10 |
| Ala | Ser | Leu | Arg<br>15 | Glu | Ala | Asp | Lys | Glu<br>20 | Lys |
| Ser | Leu | Gly | Asn<br>25 | Arg | Leu | | | | |

```
Arg  Leu  Gly  Ser  Leu  Thr  Glu  Asp  Gly  Leu  Ser  Tyr  Lys  Glu  Lys  Phe
          30                  35                  40

Val  Ile  Arg  Cys  Tyr  Glu  Val  Gly  Ile  Asn  Lys  Thr  Ala  Thr  Ile  Glu
          45                  50                  55

Thr  Ile  Ala  Asn  Leu  Leu  Gln  Glu  Val  Gly  Gly  Asn  His  Ala  Gln  Gly
60                       65                  70                           75

Val  Gly  Phe  Ser  Thr  Asp  Gly  Phe  Ala  Thr  Thr  Thr  Met  Arg  Lys
                    80                  85                       90

Leu  His  Leu  Ile  Trp  Val  Thr  Ala  Arg  Met  His  Ile  Glu  Ile  Tyr  Arg
                    95                  100                      105

Tyr  Pro  Ala  Trp  Ser  Asp  Val  Ile  Glu  Ile  Glu  Thr  Trp  Val  Gln  Gly
          110                      115                      120

Glu  Gly  Lys  Val  Gly  Thr  Arg  Arg  Asp  Trp  Ile  Leu  Lys  Asp  Tyr  Ala
          125                      130                      135

Asn  Gly  Glu  Val  Ile  Gly  Arg  Ala  Thr  Ser  Lys  Trp  Val  Met  Met  Asn
140                      145                      150                      155

Glu  Asp  Thr  Arg  Arg  Leu  Gln  Lys  Val  Ser  Asp  Asp  Val  Arg  Glu  Glu
                    160                      165                      170

Tyr  Leu  Val  Phe  Cys  Pro  Arg  Thr  Leu  Arg  Leu  Ala  Phe  Pro  Glu  Glu
                    175                      180                      185

Asn  Asn  Asn  Ser  Met  Lys  Lys  Ile  Pro  Lys  Leu  Glu  Asp  Pro  Ala  Glu
                    190                      195                      200

Tyr  Ser  Arg  Leu  Gly  Leu  Val  Pro  Arg  Arg  Ser  Asp  Leu  Asp  Met  Asn
          205                      210                      215

Lys  His  Val  Asn  Asn  Val  Thr  Tyr  Ile  Gly  Trp  Ala  Leu  Glu  Ser  Ile
220                      225                      230                      235

Pro  Pro  Glu  Ile  Ile  Asp  Thr  His  Glu  Leu  Gln  Ala  Ile  Thr  Leu  Asp
                    240                      245                      250

Tyr  Arg  Arg  Glu  Cys  Gln  Arg  Asp  Asp  Ile  Val  Asp  Ser  Leu  Thr  Ser
                    255                      260                      265

Arg  Glu  Pro  Leu  Gly  Asn  Ala  Ala  Gly  Val  Lys  Phe  Lys  Glu  Ile  Asn
          270                      275                      280

Gly  Ser  Val  Ser  Pro  Lys  Lys  Asp  Glu  Gln  Asp  Leu  Ser  Arg  Phe  Met
     285                      290                      295

His  Leu  Leu  Arg  Ser  Ala  Gly  Ser  Gly  Leu  Glu  Ile  Asn  Arg  Cys  Arg
300                 305                      310                           315

Thr  Glu  Trp  Arg  Lys  Lys  Pro  Ala  Lys  Arg
                    320                      325
```

( 2 ) INFORMATION FOR SEQ ID NO:10:

( i ) SEQUENCE CHARACTERISTICS:
        ( A ) LENGTH: 299 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 10:

```
               Leu  Glu  Trp  Lys  Pro  Lys  Pro  Lys  Leu  Pro  Gln  Leu  Leu
               1                   5                        10

Asp  Asp  His  Phe  Gly  Leu  His  Gly  Leu  Val  Phe  Arg  Arg  Thr  Phe  Ala
          15                  20                  25

Ile  Arg  Ser  Tyr  Glu  Val  Gly  Pro  Asp  Arg  Ser  Thr  Ser  Ile  Leu  Ala
30                  35                  40                            45

Val  Met  Asn  His  Met  Gln  Glu  Ala  Thr  Leu  Asn  His  Ala  Lys  Ser  Val
                    50                  55                            60
```

| | | | | | | | | | | | | | | |
|---|---|---|---|---|---|---|---|---|---|---|---|---|---|---|
| Gly | Ile | Leu | Gly | Asp | Gly | Phe | Gly | Thr | Thr | Leu | Glu | Met | Ser | Lys | Arg |
| | | | 65 | | | | | 70 | | | | | 75 | | |
| Asp | Leu | Met | Trp | Val | Val | Arg | Arg | Thr | His | Val | Ala | Val | Glu | Arg | Tyr |
| | | 80 | | | | | 85 | | | | | 90 | | | |
| Pro | Thr | Trp | Gly | Asp | Thr | Val | Glu | Val | Glu | Cys | Trp | Ile | Gly | Ala | Ser |
| | 95 | | | | | 100 | | | | | 105 | | | | |
| Gly | Asn | Asn | Gly | Met | Arg | Arg | Asp | Phe | Leu | Val | Arg | Asp | Cys | Lys | Thr |
| 110 | | | | | 115 | | | | | 120 | | | | | 125 |
| Gly | Glu | Ile | Leu | Thr | Arg | Cys | Thr | Ser | Leu | Ser | Val | Leu | Met | Asn | Thr |
| | | | | 130 | | | | | 135 | | | | | 140 | |
| Arg | Thr | Arg | Arg | Leu | Ser | Thr | Ile | Pro | Asp | Glu | Val | Arg | Gly | Glu | Ile |
| | | | 145 | | | | | 150 | | | | | 155 | | |
| Gly | Pro | Ala | Phe | Ile | Asp | Asn | Val | Ala | Val | Lys | Asp | Asp | Glu | Ile | Lys |
| | | 160 | | | | | 165 | | | | | 170 | | | |
| Lys | Leu | Gln | Lys | Leu | Asn | Asp | Ser | Thr | Ala | Asp | Tyr | Ile | Gln | Gly | Gly |
| | 175 | | | | | 180 | | | | | 185 | | | | |
| Leu | Thr | Pro | Arg | Trp | Asn | Asp | Leu | Asp | Val | Asn | Gln | His | Val | Asn | Asn |
| 190 | | | | | 195 | | | | | 200 | | | | | 205 |
| Leu | Lys | Tyr | Val | Ala | Trp | Val | Phe | Glu | Thr | Val | Pro | Asp | Ser | Ile | Phe |
| | | | | 210 | | | | | 215 | | | | 220 | | |
| Glu | Ser | His | His | Ile | Ser | Ser | Phe | Thr | Leu | Glu | Tyr | Arg | Arg | Glu | Cys |
| | | | 225 | | | | | 230 | | | | | 235 | | |
| Thr | Arg | Asp | Ser | Val | Leu | Arg | Ser | Leu | Thr | Thr | Val | Ser | Gly | Gly | Ser |
| | | 240 | | | | | 245 | | | | | 250 | | | |
| Ser | Glu | Ala | Gly | Leu | Val | Cys | Asp | His | Leu | Leu | Gln | Leu | Glu | Gly | Gly |
| | 255 | | | | | 260 | | | | | 265 | | | | |
| Ser | Glu | Val | Leu | Arg | Ala | Arg | Thr | Glu | Trp | Arg | Pro | Lys | Leu | Thr | Asp |
| 270 | | | | | 275 | | | | | 280 | | | | | 285 |
| Ser | Phe | Arg | Gly | Ile | Ser | Val | Ile | Pro | Ala | Glu | Pro | Arg | Val | | |
| | | | | 290 | | | | | 295 | | | | 299 | | |

(2) INFORMATION FOR SEQ ID NO:11:

(i) SEQUENCE CHARACTERISTICS:
      (A) LENGTH: 126 base pairs
      (B) TYPE: nucleic acid
      (C) STRANDEDNESS: single
      (D) TOPOLOGY: linear (ii) MOLECULE TYPE: cDNA to mRNA (xi) SEQUENCE DESCRIPTION: SEQ ID NO: 11:

```
TGGATCC AAT CAA CAT GTC AAC AAT GTG AAA TAC ATT GGG TGG ATT CTC        49
        Asn Gln His Val Asn Asn Val Lys Tyr Ile Gly Trp Ile Leu
        1               5                   10

AAG AGT GTT CCA ACA AAA GTT TTC GAG ACC CAG GAG TTA TGT GGC GTC        97
Lys Ser Val Pro Thr Lys Val Phe Glu Thr Gln Glu Leu Cys Gly Val
15              20                  25                  30

ACC CTC GAG TAC CGG CGG GAA TGC TCGAG                                  126
Thr Leu Glu Tyr Arg Arg Glu Cys
                35
```

What is claimed is:

1. A plant seed oil separated from a plant seed having a modified level of fatty acids as compared to a seed of said plant having a native level of fatty acids produced according to a method comprising
   growing a plant, having integrated into the genome of embryo cells a recombinant DNA sequence encoding a plant acyl-ACP thioesterase under the control of regulatory elements functional in seed during lipid accumulation, to produce seed under conditions which will promote the activity of said regulatory elements, and harvesting said seed.

2. The oil of claim 1 wherein said plant is *Brassica napus*.

3. The oil of claim 2 comprising a minimum of 15.0 mole percent laurate in fatty acids incorporated into at least one position of a triglyceride molecule.

4. The oil of claim 3 comprising a minimum of 50 mole percent laurate in fatty acids.

5. The oil of claim 1 wherein said seed is an oilseed.

6. The oil of claim 1 wherein said plant acyl-ACP thioesterase encoding sequence is a long-chain preferring acyl-ACP thioesterase sequence.

7. The oil of claim 6 wherein said long-chain preferring acyl-ACP thioesterase is from *C. tinctorius* or Brassica.

8. The oil of claim 1 wherein said plant acyl-ACP thioesterase encoding sequence is a medium-chain preferring acyl-ACP thioesterase sequence.

9. The oil of claim 8 wherein said medium-chain preferring acyl-ACP thioesterase is from *Umbellularia californica* or *Cuphea hookeriana*.

10. The oil of claim 8 wherein the percentage of long chain fatty acids is decreased and the percentage of medium-chain free fatty acids is increased.

11. The oil of claim 8 wherein the percentage of long chain fatty acids is increased and the percentage of medium-chain free fatty acids is decreased.

12. The oil of claim 1 wherein said construct further comprises a translational regulatory region functional in said plant cell immediately 5' to said plant acyl-ACP thioesterase encoding sequence and a transcriptional/translational termination regulatory region 3' to said sequence and wherein said plant acyl-ACP thioesterase encoding sequence is a sense sequence.

13. The oil of claim 12 wherein said transcriptional regulatory region is from a gene preferentially expressed in plant seed tissue.

14. The oil of claim 1 comprising a minimum of 1.0 mole percent laurate in total fatty acids, wherein said laurate is incorporated into at least one position of a triglyceride molecule and wherein wild-type seed of said plant contains less than 1.0 mole percent laurate in fatty acids.

15. A triglyceride oil from a plant selected from the group consisting of rapeseed, sunflower, cotton, cuphea, soybean, peanut, coconut, oil palm and corn wherein the fatty acid chain length composition of the oil has been modified by a method comprising:

growing a plant cell have integrated in its genome a DNA construct, said construct comprising in the 5' to 3' direction of transcription, a transcriptional regulatory region functional in said plant cell and a plant acyl-ACP thioesterase encoding sequence, under consoditions which will permit the transcription of said plant acyl-ACP thioesterase.

* * * * *